United States Patent
Fedorov et al.

(10) Patent No.: US 11,267,901 B2
(45) Date of Patent: Mar. 8, 2022

(54) COMPOSITIONS AND METHODS FOR IMMUNOTHERAPY

(71) Applicant: MEMORIAL SLOAN-KETTERING CANCER CENTER, New York, NY (US)

(72) Inventors: Victor D. Fedorov, New York, NY (US); Michel Sadelain, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 198 days.

(21) Appl. No.: 14/851,983

(22) Filed: Sep. 11, 2015

(65) Prior Publication Data
US 2015/0376296 A1    Dec. 31, 2015

Related U.S. Application Data

(63) Continuation of application No. PCT/US2014/030671, filed on Mar. 17, 2014.

(60) Provisional application No. 61/802,118, filed on Mar. 15, 2013.

(51) Int. Cl.
| | |
|---|---|
| *C07K 16/40* | (2006.01) |
| *A61K 39/00* | (2006.01) |
| *A61K 35/17* | (2015.01) |
| *C07K 14/725* | (2006.01) |
| *C07K 14/73* | (2006.01) |
| *C07K 14/705* | (2006.01) |

(52) U.S. Cl.
CPC .............. *C07K 16/40* (2013.01); *A61K 35/17* (2013.01); *A61K 39/0011* (2013.01); *A61K 39/00117* (2018.08); *A61K 39/00118* (2018.08); *A61K 39/001102* (2018.08); *A61K 39/001106* (2018.08); *A61K 39/001109* (2018.08); *A61K 39/001112* (2018.08); *A61K 39/001113* (2018.08); *A61K 39/001114* (2018.08); *A61K 39/001117* (2018.08); *A61K 39/001119* (2018.08); *A61K 39/001124* (2018.08); *A61K 39/001126* (2018.08); *A61K 39/001128* (2018.08); *A61K 39/001129* (2018.08); *A61K 39/001153* (2018.08); *A61K 39/001157* (2018.08); *A61K 39/001166* (2018.08); *A61K 39/001168* (2018.08); *A61K 39/001171* (2018.08); *A61K 39/001182* (2018.08); *A61K 39/001186* (2018.08); *A61K 39/001188* (2018.08); *A61K 39/001193* (2018.08); *A61K 39/001195* (2018.08); *C07K 14/7051* (2013.01); *C07K 14/70514* (2013.01); *C07K 14/70517* (2013.01); *A61K 2039/5156* (2013.01); *A61K 2039/5158* (2013.01); *C07K 2317/622* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,712,149 A | 1/1998 | Roberts | |
| 2014/0099309 A1* | 4/2014 | Powell, Jr | A61K 35/17 |
| | | | 424/135.1 |

FOREIGN PATENT DOCUMENTS

| | | |
|---|---|---|
| WO | WO 2008/038587 A1 | 4/2008 |
| WO | WO 2008/095141 A2 | 8/2008 |
| WO | WO 2008/121420 A1 | 10/2008 |
| WO | WO 2012/079000 A1 | 6/2012 |
| WO | WO 2013/019615 A2 | 2/2013 |
| WO | WO 2014/124143 A1 | 8/2014 |
| WO | WO 2014/145252 A2 | 9/2014 |

OTHER PUBLICATIONS

Francisco et al., 2009, J. Exp. Med. vol. 206: 3015-3029.*
Cartellieri et al., 2010, J. Biomed. Biotech, pp. 1-13.*
Hammer, Jul. 2012, Mabs vol. 4: 571-577.*
Katchi et al., 2017, Biomarker Res. vol. 5: 1-5.*
Heider et al., 2004, Canc. Immunol. Immunother. vol. 53: 567-579.*
Nakase et al., 1996, Am. J. Path. vol. 105: 761-768.*
Parry et al., 2005, Mol. Cel. Biol. vol. 25: 9543-9553.*
Akpek et al., "A High-Dose Pulse Steroid Regimen for Controlling Active Chronic Graft-Versus-Host Disease," Biol. Blood Marrow Transplant. 7:495-502 (2001).
Amarnath et al., "The PDL1-PD1 Axis Converts Human THI Cells into Regulatory T Cells," Sci. Transl. Med. 3:111ra120 (2011).
Blattman, et al., "Cancer Immunotherapy: A Treatment for the Masses," Science 305:200-205 (2004).
Blazar et al., "Advances in graft-versus-host disease biology and therapy," Nat. Rev. Immunol. 12:443-458 (2012).
Brentjens et al., "CD19-Targeted T Cells Rapidly Induce Molecular Remissions in Adults with Chemotherapy-Refractory Acute Lymphoblastic Leukemia," Sci. Transl. Med. 5:177ra38 (2013).

(Continued)

*Primary Examiner* — Amy E Juedes
(74) *Attorney, Agent, or Firm* — Baker Botts L.L.P.

(57) ABSTRACT

The present invention provides immunoresponsive cells, including T cells, cytotoxic T cells, regulatory T cells, and Natural Killer (NK) cells, expressing an antigen recognizing receptor and an inhibitory chimeric antigen receptor (iCAR). Methods of using the immunoresponsive cell include those for the treatment of neoplasia and other pathologies where an increase in an antigen-specific immune response is desired.

18 Claims, 48 Drawing Sheets
Specification includes a Sequence Listing.

(56) References Cited

OTHER PUBLICATIONS

Brentjens et al., "Genetically Targeted T cells Eradicate Systemic Acute Lymphoblastic Leukemia Xenografts," Clin. Cancer Res. 13(18):5426-5435 (2007).
Brentjens et al., "Safety and persistence of adoptively transferred autologous CD 19-targeted T cells in patients with relapsed or chemotherapy refractory B-cell leukemias," Blood 118(18):4817-4828 (2011).
Brusko et al., "Human regulatory T cells: role in autoimmune disease and therapeutic opportunities," Immunol. Rev. 223:371-390 (2008).
Bryceson, "Line of attack: NK cell specificity and integration of signals," Curr. Opin. Immunol. 20:344-352 (2008).
Burshtyn et al., "Natural Killer Cell Conjugate Assay Using Two-Color Flow Cytometry," Methods Mol. Biol. 612:89-96 (2010).
Cameron et al., "Identification of a Titin-Derived HLA-A1-Presented Peptide as a Cross-Reactive Target for Engineered MAGE A3-Directed T Cells," Sci. Transl. Med. 5:197ra103(2013).
Campoli et al., "HLA antigen changes in malignant cells: Epigenetic mechanisms and biologic significance," Oncogene 27:5869-5885 (2008).
Chaffer et al., "A Perspective on Cancer Cell Metastasis," Science 331:1559-1564 (2011).
Chemnitz et al., "SHP-1 and SHP-2 Associate with Immunoreceptor Tyrosine-Based Switch Motif of Programmed Death I upon Primary Human T Cell Stimulation, but Only Receptor Ligation Prevents T Cell Activation," J. Immunol. 173:945-954 (2004).
Cui et al., "OPCML Is a Broad Tumor Suppressor for Multiple Carcinomas and Lymphomas with Frequently Epigenetic Inactivation," PLOS One 3(8):e2990 (2008).
Di Stasi et al., "Inducible Apoptosis as a Safety Switch for Adoptive Cell Therapy," N. Engl. J. Med. 365:1673-1683 (2011).
Federov et al., "Inhibitory Chimeric Antigen Receptors (iCARs) Limit Undesirable Side Effects of T-Cell Therapies," Experimental Hematology 41:S23-S75 (2013).
Federov et al., "Novel Approaches to Enhance the Specificity and Safety of Engineered T Cells," The Cancer Journal 20(2):160-165 (2014).
Federov et al., "PD-1- and CTLA-4-Based Inhibitory Chimeric Antigen Receptors (iCARs) Divert Off-Target Immunotherapy Responses," Science Translational Medicine 5(215):215ra172 (2013).
Ferrara et al., "Graft-versus-host disease," Lancet 373:1550-1561 (2009).
Fu et al., "A Simple and Sensitive Method for Measuring Tumor-Specific T cell Cytotoxicity," PLOS One 5(7):e11867 (2010).
Gade et al., "Targeted Elimination of Prostate Cancer by Genetically Directed Human T Lymphocytes," Cancer Res. 65(19):9080-9088 (2005).
Hodi et al., "Improved Survival with Ipilimumab in Patients with Metastatic Melanoma," N. Engl. J. Med. 363(8):711-723 (2010).
International Search Report dated Nov. 20, 2014 in International Application No. PCT/US2014/030671.
Kalos et al., "T cells with Chimeric Antigen Receptors Have Potent Antitumor Effects and Can Establish Memory in Patients with Advanced Leukemia," Sci. Transl. Med. 3:95ra73 (2011).
Kieback et al., "A safeguard eliminates T cell receptor gene-modified autoreactive T cells after adoptive transfer," PNAS 105(2):623-628 (2008).
Kinoshita et al., "Expression of Prostate-Specific Membrane Antigen in Normal and Malignant Human Tissues," World J. Surg. 30:628-636 (2006).
Kotsiou et al., "New ways to separate Graft-versus-Host Disease and Graft-versus-Tumour effects after allogeneic haematopoietic stem cell transplantation," Br. J. Haematol. 160:133-145 (2013).
Linette et al., "Cardiovascular toxicity and titin cross-reactivity of affinity-enhanced T cells in myeloma and melanoma," Blood 122(6):863-871 (2013).
Lupo-Stanghellini et al., "Clinical Impact of Suicide Gene Therapy in Allogeneic Hematopoietic Stem Cell Transplantation," Hum. Gene Ther. 21:241-250 (2010).
Maher et al., "Human T-lymphocyte cytotoxicity and proliferation directed by a single chimeric TCRζ/CD28 receptor," Nat. Biotechnol. 20:70-75 (2002).
Markley et al., "IL-7 and IL-21 are superior to IL-2 and IL-15 in promoting human T cell-mediated rejection of systemic lymphoma in immuno-deficient mice," Blood 115(17):3508-3519 (2010).
Meimei et al., "Lost expression of DCC gene in ovarian cancer and its inhibition in ovarian cancer cells," Med. Oncol 28:282-289 (2011).
Morgan et al., "Cancer regression and neurologic toxicity following anti-MAGE-A3 TCR gene therapy," J. Immunother. 36(2):133-151 (2013).
Morgan et al., "Case Report of a Serious Adverse Event Following the Administration of T Cells Transduced With a Chimeric Antigen Receptor Recognizing ERBB2," Mol. Ther. 18(4):843-851 (2010).
Nishimura et al., "Development of Lupus-like Autoimmune Diseases by Disruption of the PD-1 Gene Encoding an ITIM Motif Carrying Immunoreceptor," Immunity 11:141-151 (1999).
Padmanee et al., "Novel cancer immunotherapy agents with survival benefit: recent successes and next steps," Nature Reviews Cancer 11(11):805-812 (2011).
Pardoll, "The blockade of immune checkpoints in cancer immunotherapy," Nat. Rev. Cancer 12:252-264 (2012).
Parry et al., "CTLA-4 and PD-1 Receptors Inhibit T-cell Activation by Distinct Mechanisms," Mol. Cell. Biol. 25(21):9543-9553 (2005).
Pedicord et al., "Single dose of anti-CTLA-4 enhances CD8+ T-cell memory formation, function, and maintenance," PNAS 108:266-271 (2011).
Peggs et al., "Cell intrinsic mechanisms of T-cell inhibition and application to cancer therapy," Immunol. Rev. 224:141-165 (2008).
Restifo et al., "Adoptive immunotherapy for cancer: Harnessing the T cell response," Nat. Rev. Immunol. 12:269-281 (2012).
Rudd, "The reverse stop-signal model for CTLA4 function," Nat. Rev. Immunol. 8:153-160 (2008).
Sadelain et al., "The Basic Principles of Chimeric Antigen Receptor Design," Cancer Discov. 3(4):388-398 (2013).
Sadelain et al., "The promise and potential pitfalls of chimeric antigen receptors," Curr. Opin. Immunol. 21:215-223 (2009).
Sharma et al., "Novel cancer immunotherapy agents with survival benefit: Recent successes and next steps," Nat. Rev. Cancer 11:805-812 (2011).
Singh et al., "p53 Target Gene SMAR1 is Dysregulated in Breast Cancer: Its Role in Cancer Cell Migration and Invasion," PLOS One 2(8):e660 (2007).
Stephan et al., "T cell-encoded CD80 and 4-1BBL induce auto- and transcostimulation, resulting in potent tumor rejection," Nat. Med. 13(12):1440-1449 (2007).
Teft et al., "A Molecular Perspective of CTLA-4 Function," Annu. Rev. Immunol. 24:65-97 (2006).
Thaventhiran et al., "T Cell Co-inhibitory Receptors: Functions and Signalling Mechanisms," J Clin Cell Immunol s12:1-12 (2012).
Themeli et al., "Generation of tumor-targeted human T lymphocytes from induced pluripotent stem cells for cancer therapy," Nat. Biotechnol. 31(10):928-933 (2013).
Tivol et al., "Loss of CTLA-4 leads to Massive Lymphoproliferation and Fatal Multiorgan Tissue Destruction, Revealing a Critical Negative Regulatory Role of CTLA-4," Immunity 3:541-547 (1995).
Topalian et al., "Safety, Activity, and Immune Correlates of Anti-PD-1 Antibody in Cancer," N. Engl. J. Med. 366(26):2443-2454 (2012).
Tsuboi et al., "Two opposing roles of O-glycans in tumor metastasis," Trends Mol. Med. 18(4):224-232 (2012).
Tsuchiya et al., "Differential expression of N-cadherin and E-cadherin in normal human tissues," Arch. Histol. Cytol.69(2):135-145 (2006).
Turtle et al., "Engineered T cells for anti-cancer therapy," Curr. Opin. Immunol. 24:633-639(2012).
Uhlen et al., "Towards a knowledge-based Human Protein Atlas," Nat. Biotechnol. 28(12):1248-1250 (2010).
Velu et al., "Enhancing SIV-specific immunity in vivo by PD-I blockade," Nature 458:206-210 (2009).

(56) References Cited

OTHER PUBLICATIONS

Vogler et al., "An Improved Bicistronic CD20/tCD34 Vector for Efficient Purification and In Vivo Depletion of Gene-Modified T cells for Adoptive Immunotherapy," Mol. Ther. 18(7):1330-1338 (2010).
Wang et al., "Establishment of NOD-Pdcd1−/− mice as an efficient animal model of type I diabetes," PNAS 102(33):11823-11828 (2005).
Yokosuka et al., "Programmed cell death 1 forms negative costimulatory microclusters that directly inhibit T cell receptor signaling by recruiting phosphatase SHP2," J. Exp. Med. 209(6):1201-1217 (2012).
Yuan et al., "Langerhans Cells Derived from Genetically Modified Human CD34+ Hemopoietic Progenitors Are More Potent Than Peptide-Pulsed Langerhans Cells for Inducing Antigen Specific CD8+ Cytolytic T Lymphocyte Responses," J. Immunol. 174:758-766 (2005).
Altvater et al., "2B4 (CD244) Signaling by Recombinant Antigen-specific Chimeric Receptors Costimulates Natural Killer Cell Activation to Leukemia and Neuroblastoma Cells," Clin Cancer Res 15(15):4857-4866 (2009).
Wilkie et al., "Dual targeting of ErbB2 and MUC1 in breast cancer using chimeric antigen receptors engineered to provide complementary signaling," Journal of Clinical Immunology 32(5):1059-1070 (2012).
Chicaybam et al., "A conditional system for the activation of lymphocytes expressing activating and inhibitory CARs," XVIII Annual Congress of the European Society of Gene and Cell Therapy (ESGCT), P60:1418 (2010).
Chicaybam et al., "Chimeric Antigen Receptors in Cancer Immuno-Gene Therapy: Current Status and Future Directions," International Reviews of Immunology, 30:294-311 (2011).
Koestner et al., "PD-L1 blockade effectively restores strong graft-versus-leukemia effects without graft-versus-host disease after delayed adoptive transfer of T-cell receptor gene-engineered allogeneic CD8+ T cells," Blood, 117(3), 1030-1041 (2011).
Casucci et al., "Suicide Gene Therapy to Increase the Safety of Chimeric Antigen Receptor-Redirected T Lymphocytes," Journal of Cancer, 2:378-382 (2011).
Davies et al., "Combining CD19 Redirection and Alloanergization to Generate Tumor-Specific Human T Cells for Allogeneic Cell Therapy of B-Cell Malignancies," Cancer Res., 70(10):3915-3924 (2010).
Hoyer et al., "CD33 Detection by Immunohistochemistry in Paraffin-Embedded Tissues," Am J Clin Pathol, 129:316-323 (2008).
Silver et al., "Prostate-specific Membrane Antigen Expression in Normal and Malignant Human Tissues," Clin. Cancer Res., 3:81-85 (1997).
Torikai et al., "A foundation for universal T-cell based immunotherapy: T cells engineered to express a CD19-specific chimeric-antigen-receptor and eliminate expression of endogenous TCR," Blood, 119(24):5697-5705 (2012).
Yazawa et al., "Immunotherapy using unconjugated CD19 monoclonal antibodies in animal models for B lymphocyte malignancies and autoimmune disease," PNAS 102(42):15178-15183 (2005).

* cited by examiner

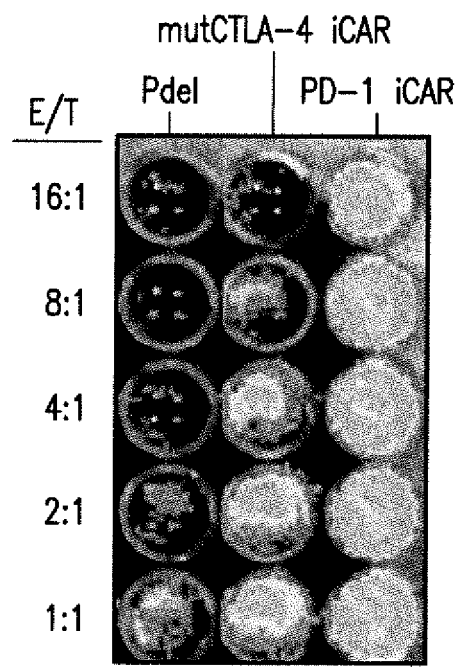
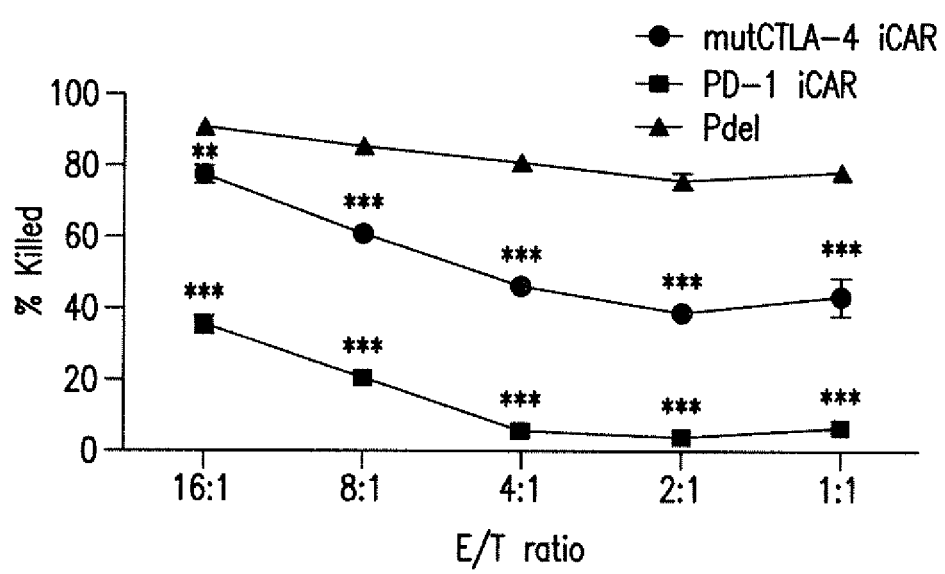
FIG. 2C

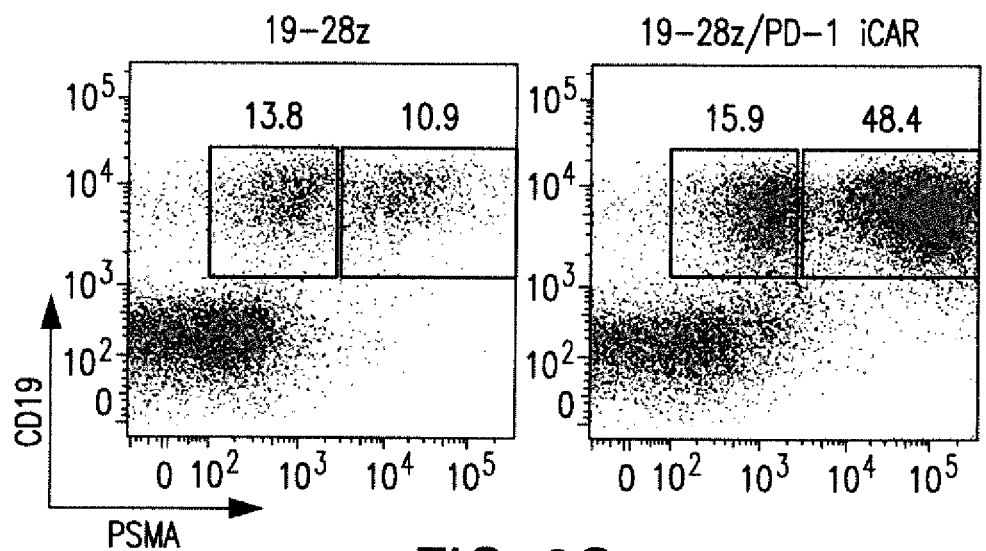
FIG. 8C
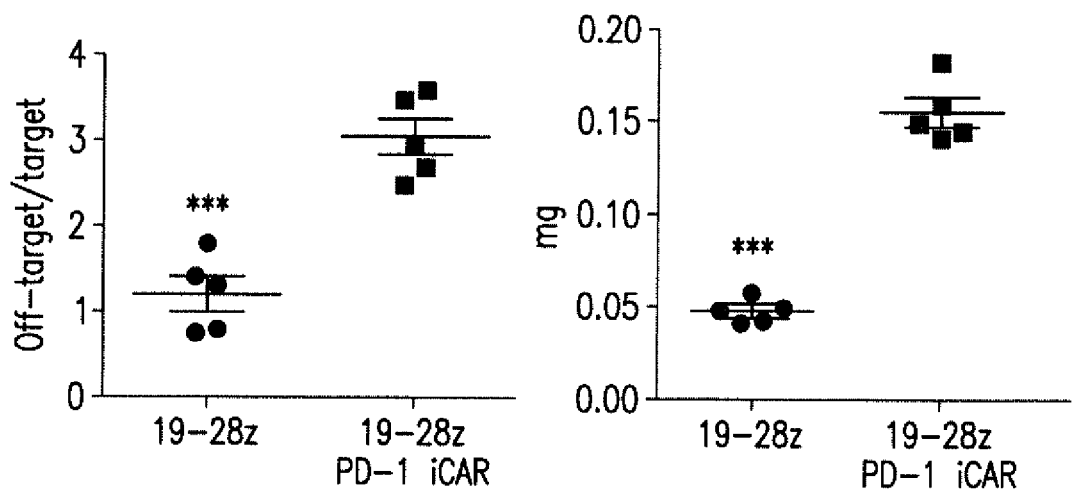
FIG. 8D
FIG. 8E

WB-Intracellular Domain of CTLA4

1. CTLA4 iCAR Transduced T-cells
2. Untransduced T-cells
3. EL4

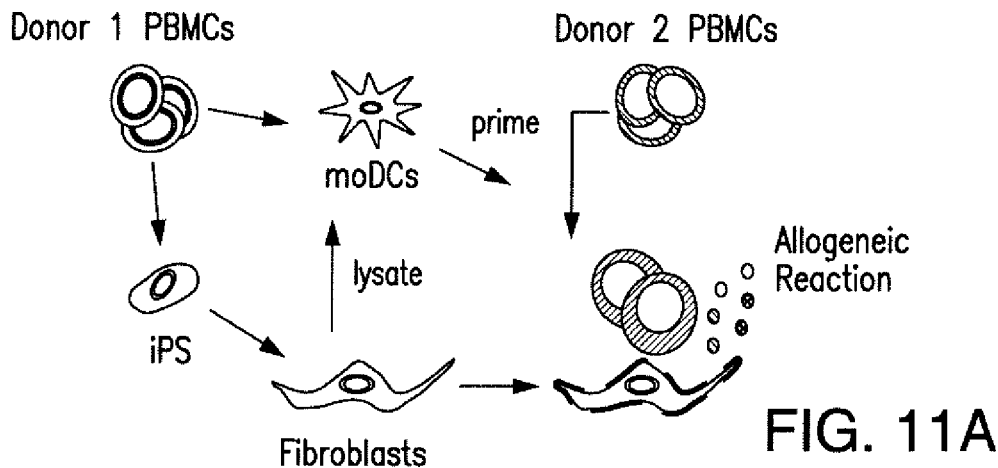
FIG. 11A
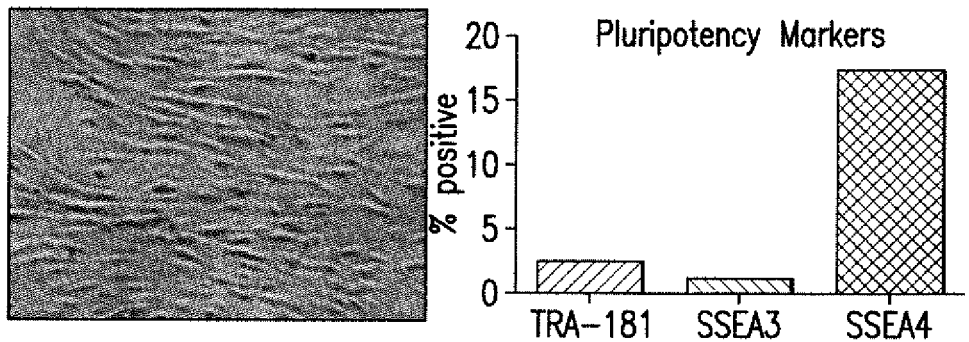
FIG. 11B
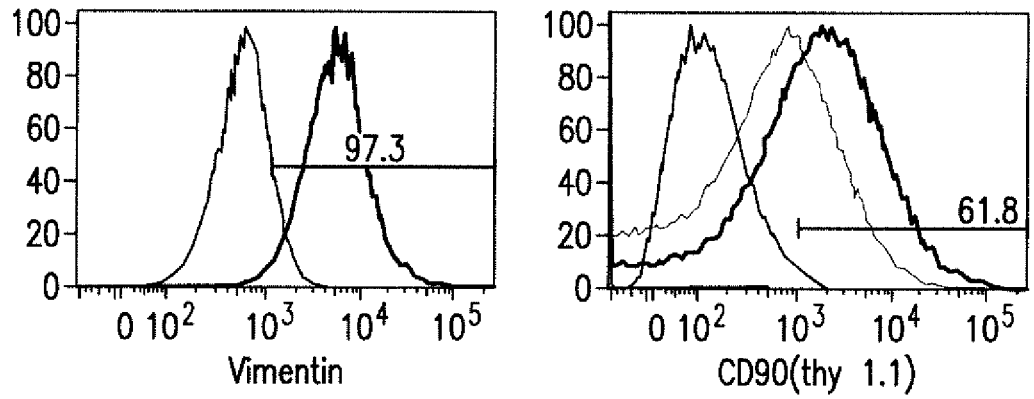
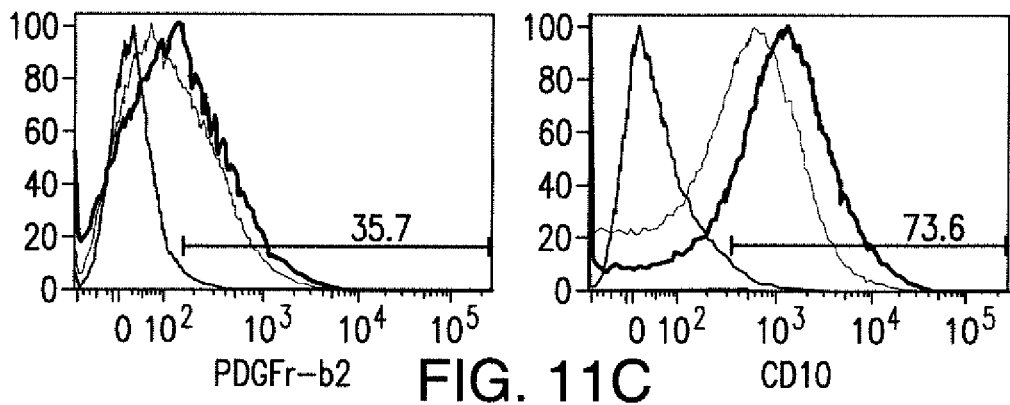
FIG. 11C

|   | SHP-1 | SHP-2 | pY |
|---|---|---|---|
| Control | ● | ● | ● |
| Target | · | · | ● |
| Off-Target | ● | ● | ● |

| Raw BLI (Flux-photons) | mutCTLA4 iCAR | | | PD1 iCAR | | | Pdel | | |
|---|---|---|---|---|---|---|---|---|---|
| 4:1 | 1.5E+07 | 1.4E+07 | 1.4E+07 | 1.5E+07 | 1.5E+07 | 1.5E+07 | 1.6E+07 | 1.6E+07 | 1.6E+07 |
| 2:1 | 1.2E+07 | 9.9E+06 | 1.1E+07 | 1.2E+07 | 1.0E+07 | 1.1E+07 | 1.2E+07 | 1.2E+07 | 1.2E+07 |
| 1:1 | 8.2E+06 | 8.2E+06 | 8.2E+06 | 8.3E+06 | 8.5E+06 | 8.4E+06 | 7.9E+06 | 9.0E+06 | 8.4E+06 |
| No T cells | 2.4E+07 | 1.2E+07 | 1.9E+07 | | | | | | |

FIG. 19B

| pg/mL | mutCTLA4 iCAR | | | PD1 iCAR | | | Pdel | | |
|---|---|---|---|---|---|---|---|---|---|
| GM-CSF | 647.2 | 801.3 | 765.5 | 703.8 | 897.3 | 783.4 | 714.8 | 818.8 | 774.9 |
| INFγ | 621.2 | 552.2 | 534.4 | 533 | 595 | 533.2 | 581 | 622 | 618.8 |
| TNF-α | 379 | 422 | 400.1 | 388 | 379 | 375.5 | 394 | 643 | 523.2 |

FIG. 19C

| Raw BLI (Flux-photons) | mutCTLA4 iCAR | | | PD1 iCAR | | | Pdel | | |
|---|---|---|---|---|---|---|---|---|---|
| 16:1 | 3.87E+01 | 4.28E+01 | 4.07E+01 | 1.67E+01 | 2.09E+01 | 1.85E+01 | 4.88E+01 | 4.74E+01 | 4.70E+01 |
| 8:1 | 3.09E+01 | 3.30E+01 | 3.23E+01 | 9.96E+00 | 1.19E+01 | 1.10E+01 | 4.56E+01 | 4.45E+01 | 4.50E+01 |
| 4:1 | 2.30E+01 | 2.62E+01 | 2.40E+01 | 3.27E+01 | 3.06E+01 | 3.21E+01 | 4.24E+01 | 4.28E+01 | 4.25E+01 |
| 2:1 | 2.11E+01 | 1.98E+01 | 2.02E+01 | 5.27E+01 | 3.48E+01 | 1.90E+00 | 3.80E+01 | 4.21E+01 | 3.99E+01 |
| 1:1 | 2.78E+01 | 1.81E+01 | 2.25E+01 | 5.01E+01 | 2.00E+00 | 3.53E+00 | 4.11E+01 | 4.15E+01 | 4.12E+01 |
| No T cells | 3.92E+07 | 3.85E+07 | 3.76E+07 | | | | | | |

| PD1 vs Pdel | Significant? | P value | PDI | Pdel | Difference | SE of difference | t ratio | df |
|---|---|---|---|---|---|---|---|---|
| 16:1 | * | 2.72372E-05 | 35.47 | 90.58 | -55.12 | 2.55 | 21.59 | 4 |
| 8:1 | * | 7.47524E-07 | 20.80 | 85.47 | -64.67 | 1.22 | 53.20 | 4 |
| 4:1 | * | 9.99669E-10 | 6.03 | 80.83 | -74.80 | 0.27 | 278.33 | 4 |
| 2:1 | * | 1.2563E-05 | 3.73 | 75.87 | -72.13 | 2.75 | 26.23 | 4 |
| 1:1 | * | 1.74306E-06 | 6.67 | 78.23 | -71.57 | 1.66 | 43.03 | 4 |

| CTLA4 vs Pdel | Significant? | P value | CTLA4 | Pdel | Difference | SE of difference | t ratio | df |
|---|---|---|---|---|---|---|---|---|
| 16:1 | * | 0.00581413 | 77.33 | 90.58 | -13.25 | 2.47 | 5.37 | 4 |
| 8:1 | * | 5.02912E-05 | 60.86 | 85.47 | -24.61 | 1.33 | 18.50 | 4 |
| 4:1 | * | 4.23971E-05 | 46.33 | 80.83 | -34.50 | 1.79 | 19.31 | 4 |
| 2:1 | * | 9.05225E-05 | 38.67 | 75.87 | -37.20 | 2.33 | 15.94 | 4 |
| 1:1 | * | 0.0027265 | 43.27 | 78.23 | -34.97 | 5.30 | 6.60 | 4 |

FIG. 19D

| GM-CSF RAW (pg/ml) | Pdel | | Avg Pdel | mutCTLA4 iCAR | | | PD1 iCAR | |
|---|---|---|---|---|---|---|---|---|
| 16:1 | 564.94 | 573.44 | 591.49 | 576.62 | 549.74 | 670.09 | 596.70 | 181.79 | 245.95 | 209.53 |
| 8:1 | 339.22 | 378.48 | 320.44 | 346.05 | 277.03 | 217.73 | 243.96 | 58.42 | 42.98 | 48.67 |
| 4:1 | 179.60 | 136.10 | 190.34 | 168.68 | 74.20 | 75.28 | 75.93 | 26.04 | 25.31 | 25.69 |
| 2:1 | 63.26 | 71.91 | 73.08 | 69.42 | 26.72 | 26.80 | 26.34 | 9.54 | 8.97 | 9.06 |
| 1:1 | 20.49 | 23.10 | 16.49 | 20.03 | 6.15 | 6.92 | 6.59 | 2.49 | 3.38 | 2.91 |

| %PDEL | mutCTLA4 iCAR | | | PD1 iCAR | | |
|---|---|---|---|---|---|---|
| 16:1 | 95.34 | 116.21 | 103.48 | 42.65 | 36.34 |
| 8:1 | 80.05 | 62.92 | 70.50 | 12.42 | 14.06 |
| 4:1 | 43.99 | 44.63 | 45.02 | 15.00 | 15.23 |
| 2:1 | 38.49 | 38.61 | 37.94 | 12.92 | 13.06 |
| 1:1 | 30.72 | 34.57 | 32.89 | 16.88 | 14.55 |

FIG. 19E

| Normalized flux | Low Pdel | | | High Pdel | | | High P-PDI | | | Low P-PDI | | |
|---|---|---|---|---|---|---|---|---|---|---|---|---|
| 16:1 | 96.76 | 96.88 | 96.99 | 97.41 | 96.9 | 97.2 | 54.7 | 59.9 | 57.8 | 96.65 | 93.5 | 95 |
| 8:1 | 87.3 | 92.68 | 89.71 | 97.66 | 97.02 | 97.03 | 24.7 | 30.7 | 27.3 | 83.6 | 82.4 | 83.8 |
| 4:1 | 83.2 | 84.2 | 83.81 | 96.65 | 95.1 | 95.44 | 21.5 | 25.8 | 23.48 | 74.3 | 74.2 | 74.8 |
| 2:1 | 77.6 | 80.1 | 78 | 91.4 | 92.68 | 92.87 | 18.3 | 15.3 | 16.2 | 64.3 | 66.8 | 65.1 |
| 1:1 | 71.1 | 68 | 69.1 | 89.4 | 85.7 | 87.37 | 13.7 | 17.5 | 15.1 | 48.6 | 57.5 | 53.4 |

Low PD1 vs Low Pdel

| | Significant? | P value | Low PDI | Low Pdel | Difference | SE of difference | t ratio | df |
|---|---|---|---|---|---|---|---|---|
| 16:1 | | 0.12 | 95.05 | 96.88 | −1.83 | 0.91 | 2.00 | 4.00 |
| 8:1 | * | 0.01 | 83.27 | 89.90 | −6.63 | 1.62 | 4.10 | 4.00 |
| 4:1 | * | 0.00 | 74.43 | 83.74 | −9.30 | 0.35 | 26.96 | 4.00 |
| 2:1 | * | 0.00 | 65.40 | 78.57 | −13.17 | 1.07 | 12.31 | 4.00 |
| 1:1 | * | 0.00 | 53.17 | 69.40 | −16.23 | 2.73 | 5.95 | 4.00 |

High PDI vs High Pdel

| | Significant? | P value | High PDI | High Pdel | Difference | SE of difference | t ratio | df |
|---|---|---|---|---|---|---|---|---|
| 16:1 | * | 0.00 | 57.47 | 97.17 | −39.70 | 1.52 | 26.16 | 4.00 |
| 8:1 | * | 0.00 | 27.57 | 97.24 | −69.67 | 1.75 | 39.81 | 4.00 |
| 4:1 | * | 0.00 | 23.59 | 95.73 | −72.14 | 1.33 | 54.29 | 4.00 |
| 2:1 | * | 0.00 | 16.60 | 92.32 | −75.72 | 1.00 | 75.60 | 4.00 |
| 1:1 | * | 0.00 | 15.43 | 87.49 | −72.06 | 1.54 | 46.75 | 4.00 |

FIG. 20A

| Normalized flux | PSMA low | | | PSMA high | | |
|---|---|---|---|---|---|---|
| 8:1 | 74.3 | 73.8 | 73.8 | 61.3 | 68.6 | 70.7 |
| 4:1 | 64.3 | 64.1 | 64.7 | 21.5 | 31.6 | 25.54 |
| 2:1 | 57.5 | 57 | 57.6 | 13.8 | 19.9 | 16.1 |
| 1:1 | 48.6 | 49.4 | 49.3 | 20.7 | 9.7 | 15.9 |

| PSAM low vs PSMA High | | | | | | | |
|---|---|---|---|---|---|---|---|
| | Significant? | P value | PSMA Low | PSMA high | Difference | SE of difference | t ratio | df |
| 8:1 | | 0.08 | 73.70 | 66.87 | 6.83 | 2.87 | 2.38 | 4.00 |
| 4:1 | * | 0.00 | 64.37 | 26.21 | 38.15 | 2.94 | 12.98 | 4.00 |
| 2:1 | * | 0.00 | 57.37 | 16.60 | 40.77 | 1.79 | 22.80 | 4.00 |
| 1:1 | * | 0.00 | 49.10 | 15.43 | 33.67 | 3.19 | 10.54 | 4.00 |

| Days | Raw BLI (Flux-photons) | | | | | | | | | |
|---|---|---|---|---|---|---|---|---|---|---|
| | No T Cells | | | PD1 iCAR | | | Pdel | | | |
| 3.00 | 7.78E+07 | 1.43E+07 | 1.40E+07 | 1.48E+07 | 1.44E+07 | 1.46E+07 | 1.69E+07 | 4.44E+07 | 1.15E+07 | 2.74E+07 | 8.59E+05 | 5.46E+07 | 5.81E+06 | 2.32E+07 |
| 5.00 | 4.09E+07 | 1.91E+07 | 1.04E+07 | 4.73E+07 | 2.78E+07 | 8.26E+06 | 9.87E+06 | 3.93E+07 | 2.58E+07 | 6.17E+06 | 4.41E+06 | 2.09E+06 | 2.05E+06 | 4.09E+06 |
| 8.00 | 2.22E+07 | 2.01E+07 | 1.50E+07 | 2.82E+07 | 2.60E+07 | 3.28E+07 | 1.47E+07 | 3.29E+07 | 2.17E+07 | 5.28E+06 | 4.76E+06 | 5.43E+06 | 2.59E+06 | 3.19E+06 |
| 34.00 | 4.62E+07 | 2.55E+07 | 1.34E+07 | 5.53E+07 | 3.36E+07 | 5.63E+07 | 3.42E+07 | 5.85E+07 | 2.84E+07 | 2.01E+07 | 6.37E+06 | 1.32E+06 | 1.25E+06 | 2.19E+06 |
| 48.00 | 4.39E+07 | 1.96E+07 | 3.81E+07 | 3.65E+07 | 2.70E+07 | 7.50E+07 | 2.56E+07 | 5.23E+06 | 3.17E+07 | 2.83E+06 | 7.10E+05 | 1.44E+06 | 1.86E+06 | 2.06E+06 |

FIG. 21B

No T cells vs Pdel

| | Significant? | P value | No Tcells | Pdel | Difference | SE of difference | t ratio | df |
|---|---|---|---|---|---|---|---|---|
| 3.00E+00 | | 7.75E-01 | 2.71E+07 | 2.24E+07 | 4.69E+06 | 1.58E+07 | 2.96E-01 | 8.00E+00 |
| 5.00E+00 | * | 5.97E-03 | 2.91E+07 | 3.76E+06 | 2.53E+07 | 6.83E+06 | 3.71E+00 | 8.00E+00 |
| 8.00E+00 | * | 6.39E-05 | 2.23E+07 | 4.25E+06 | 1.81E+07 | 2.38E+06 | 7.59E+00 | 8.00E+00 |
| 3.40E+01 | * | 2.58E-03 | 3.48E+07 | 2.63E+06 | 3.22E+07 | 7.46E+06 | 4.31E+00 | 8.00E+00 |
| 4.80E+01 | * | 9.12E-05 | 3.30E+07 | 1.78E+06 | 3.12E+07 | 4.33E+06 | 7.21E+00 | 8.00E+00 |

No T cells vs PD1

| | Significant? | P value | No Tcells | PD1 | Difference | SE of difference | t ratio | df |
|---|---|---|---|---|---|---|---|---|
| 3.00E+00 | | 6.45E-01 | 2.71E+07 | 2.03E+07 | 6.74E+06 | 1.41E+07 | 4.79E-01 | 8.00E+00 |
| 5.00E+00 | | 6.48E-01 | 2.91E+07 | 2.45E+07 | 4.55E+06 | 9.61E+06 | 4.74E-01 | 8.00E+00 |
| 8.00E+00 | | 7.58E-01 | 2.23E+07 | 2.37E+07 | -1.44E+06 | 4.52E+06 | 3.18E-01 | 8.00E+00 |
| 3.40E+01 | | 4.75E-01 | 3.48E+07 | 4.21E+07 | -7.30E+06 | 9.74E+06 | 7.49E-01 | 8.00E+00 |
| 4.80E+01 | | 7.25E-01 | 3.30E+07 | 3.77E+07 | -4.69E+06 | 1.28E+07 | 3.65E-01 | 8.00E+00 |

Relative to On-Target

| | 1928z/Pdel | | 1928z/PD1 iCAR | | 1928z/mutCTLA4 iCAR | |
|---|---|---|---|---|---|---|
| INFg | 1.05 | 0.93 | 0.35 | 0.18 | 0.51 | 0.54 |
| IL2 | 0.85 | 0.94 | 0.10 | 0.11 | 0.38 | 0.42 |
| TNFa | 1.05 | 1.02 | 0.29 | 0.28 | 0.45 | 0.43 |
| IL10 | 0.92 | 0.98 | 0.27 | 0.27 | 0.54 | 0.65 |
| GMCSF | 0.95 | 1.04 | 0.23 | 0.26 | 0.62 | 0.69 |

| Significant? | P value | 1928z/pdel | 1928z/pd1 | Difference | SE of difference | t ratio | df |
|---|---|---|---|---|---|---|---|
| INFg | * | 0.00 | 0.95 | 0.26 | 0.69 | 0.07 | 9.51 | 4.00 |
| IL2 | * | 0.00 | 0.89 | 0.12 | 0.78 | 0.03 | 27.09 | 4.00 |
| TNFa | * | 0.00 | 1.02 | 0.27 | 0.75 | 0.02 | 35.73 | 4.00 |
| IL10 | * | 0.00 | 0.96 | 0.28 | 0.67 | 0.02 | 29.46 | 4.00 |
| GMCSF | * | 0.00 | 1.00 | 0.25 | 0.75 | 0.03 | 26.52 | 4.00 |

| Significant? | P value | 1928z/pdel | 1928z/mutCTLA4 | Difference | SE of difference | t ratio | df |
|---|---|---|---|---|---|---|---|
| INFg | * | 0.00 | 0.95 | 0.54 | 0.41 | 0.06 | 7.18 | 4.00 |
| IL2 | * | 0.00 | 0.89 | 0.40 | 0.49 | 0.03 | 17.32 | 4.00 |
| TNFa | * | 0.00 | 1.02 | 0.44 | 0.58 | 0.02 | 37.31 | 4.00 |
| IL10 | * | 0.00 | 0.96 | 0.59 | 0.36 | 0.04 | 9.87 | 4.00 |
| GMCSF | * | 0.00 | 1.00 | 0.65 | 0.35 | 0.03 | 10.30 | 4.00 |

FIG. 22A

| Cell Counts | Significant? | P value | 1928z/pdel | 1928z/pd1 | Difference | SE of difference | t ratio | df |
|---|---|---|---|---|---|---|---|---|
| 0 | | | | | | | | |
| 7 | * | 0.00226118 | 464667 | 246000 | 218667 | 31497.8 | 6.94229 | 4 |
| 14 | * | 0.000187776 | 4490000 | 840333 | 3649667 | 275554 | 13.2448 | 4 |

FIG. 22B

| Normalized mCherry signal | 1928z/mutCTLA4 iCAR | | | | 1928z/PD1 iCAR | | | | 1928z/Pdel | | | | 1928z | | | |
|---|---|---|---|---|---|---|---|---|---|---|---|---|---|---|---|---|
| 2.00 | 0.98 | 1.23 | 1.19 | 1.21 | 0.96 | 0.98 | 1.58 | 0.90 | 1.02 | 1.02 | 1.06 | 1.03 | 1.11 | 1.02 | 0.98 |
| 18.00 | 0.88 | 1.43 | 1.09 | 1.21 | 1.27 | 1.58 | 1.00 | 1.00 | 1.02 | 0.41 | 0.27 | 0.43 | 0.69 | 0.40 | 0.26 |
| 38.00 | 0.73 | 0.54 | 0.62 | 0.78 | 0.79 | 1.09 | 0.75 | 0.38 | 0.08 | 0.06 | 0.06 | 0.09 | 0.09 | 0.10 |
| 120.00 | 0.12 | 0.27 | 0.11 | 0.06 | 1.66 | 1.58 | 1.00 | 0.04 | 0.05 | 0.05 | 0.03 | 0.09 | 0.07 | 0.07 |

| Significant? | P value | 1928z/pdel | 1928z/pd1 | Difference | SE of difference | t ratio | df |
|---|---|---|---|---|---|---|---|
| 2.00 | 1.06E-01 | 1.02 | 0.97 | -0.06 | 0.03 | 1.90 | 6.00 |
| 18.00 | * | 9.54E-04 | 0.37 | 1.22 | 0.85 | 0.14 | 6.01 | 6.00 |
| 38.00 | * | 2.11E-04 | 0.07 | 0.96 | 0.89 | 0.11 | 7.95 | 6.00 |
| 120.00 | * | 1.32E-04 | 0.04 | 1.38 | 1.33 | 0.15 | 8.64 | 6.00 |

| Significant? | P value | 1928z/pdel | 1928z/mutCTLA4 | Difference | SE of difference | t ratio | df |
|---|---|---|---|---|---|---|---|
| 2.00 | 7.44E-02 | 1.02 | 1.15 | -0.13 | 0.06 | 2.16 | 6.00 |
| 18.00 | * | 6.04E-04 | 0.37 | 1.15 | -0.78 | 0.12 | 6.55 | 6.00 |
| 38.00 | * | 3.79E-05 | 0.07 | 0.67 | -0.60 | 0.06 | 10.77 | 6.00 |
| 120.00 | 8.37E-02 | 0.04 | 0.14 | -0.10 | 0.05 | 2.07 | 6.00 |

FIG. 22C

SEQUENCE LISTING

<160> NUMBER OF SEQ ID NOS: 34

<210> SEQ ID NO 1
<211> LENGTH: 164
<212> TYPE: PRT
<213> ORGANISM: Homo sapiens

<400> SEQUENCE: 1

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60
```

```
Gln Gln Gly Gln Asn Gln Leu Tyr Asn Glu Leu Asn Leu Gly Arg Arg
 65                  70                  75                  80

Glu Glu Tyr Asp Val Leu Asp Lys Arg Gly Arg Asp Pro Glu Met
                 85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 2
<211> LENGTH: 220
<212> TYPE: PRT
<213> ORGANISM: Homo sapiens

<400> SEQUENCE: 2

Met Leu Arg Leu Leu Leu Ala Leu Asn Leu Phe Pro Ser Ile Gln Val
  1               5                  10                  15

Thr Gly Asn Lys Ile Leu Val Lys Gln Ser Pro Met Leu Val Ala Tyr
             20                  25                  30

Asp Asn Ala Val Asn Leu Ser Cys Lys Tyr Ser Tyr Asn Leu Phe Ser
         35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
             85                  90                  95

Phe Tyr Leu Gln Asn Leu Tyr Val Asn Gln Thr Asp Ile Tyr Phe Cys
        100                 105                 110

Lys Ile Glu Val Met Tyr Pro Pro Tyr Leu Asp Asn Glu Lys Ser
    115                 120                 125

Asn Gly Thr Ile Ile His Val Lys Gly Lys His Leu Cys Pro Ser Pro
130                 135                 140

Leu Phe Pro Gly Pro Ser Lys Pro Phe Trp Val Leu Val Val Gly
145                 150                 155                 160

Gly Val Leu Ala Cys Tyr Ser Leu Leu Val Thr Val Ala Phe Ile Ile
            165                 170                 175

Phe Trp Val Arg Ser Lys Arg Ser Arg Leu Leu His Ser Asp Tyr Met
        180                 185                 190

Asn Met Thr Pro Arg Arg Pro Gly Pro Thr Arg Lys His Tyr Gln Pro
    195                 200                 205

Tyr Ala Pro Pro Arg Asp Phe Ala Ala Tyr Arg Ser
    210                 215                 220

<210> SEQ ID NO 3
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<220> FEATURE:
<221> NAME/KEY: MOD_RES
<222> LOCATION: (486)..(486)
<223> OTHER INFORMATION: Any amino acid

<400> SEQUENCE: 3
```

Met Ala Leu Pro Val Thr Ala Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Glu Pro Pro
370                 375                 380

```
Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Gly Arg Asp Pro
            405                 410                 415

Glu Met Gly Gly Lys Pro Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
        450                 455                 460

Gly Leu Ser Thr Ala Thr Lys Asp Thr Tyr Asp Ala Leu His Met Gln
465                 470                 475                 480

Ala Leu Pro Pro Arg Xaa
            485
```

<210> SEQ ID NO 4
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4

```
ccatggctct cccagtgact gccctactgc ttccctagc gcttctcctg catgcagagg      60
tgaagctgca gcagtctggg gctgagctgg tgaggcctgg gtcctcagtg aagatttcct    120
gcaaggcttc tggctatgca ttcagtagct actggatgaa ctgggtgaag cagaggcctg    180
gacagggtct tgagtggatt ggacagattt atcctggaga tggtgatact aactacaatg    240
gaaagttcaa gggtcaagcc acactgactg cagacaaatc ctccagcaca gcctacatgc    300
agctcagcgg cctaacatct gaggactctg cggtctatt ctgtgcaaga aagaccatta    360
gttcggtagt agatttctac tttgactact ggggccaagg gaccacggtc accgtctcct    420
caggtggagg tggatcaggt ggaggtggat ctggtggagg tggatctgac attgagctca    480
cccagtctcc aaaattcatg tccacatcag taggagacag ggtcagcgtc acctgcaagg    540
ccagtcagaa tgtgggtact aatgtagcct ggtatcaaca gaaaccagga caatctccta    600
aaccactgat ttactcggca acctaccgga acagtggagt ccctgatcgc ttcacaggca    660
gtggatctgg gacagatttc actctcacca tcactaacgt gcagtctaaa gacttggcag    720
actatttctg tcaacaatat aacaggtatc cgtacacgtc cggaggggg accaagctgg    780
agatcaaacg ggcggccgca attgaagtta tgtatcctcc tccttaccta gacaatgaga    840
agagcaatgg aaccattatc catgtgaaag ggaaacacct ttgtccaagt cccctatttc    900
ccggaccttc taagccctt tgggtgctgg tggtggttgg tggagtcctg gcttgctata    960
gcttgctagt aacagtggcc tttattattt tctgggtgag gagtaagagg agcaggctcc   1020
tgcacagtga ctacatgaac atgactcccc gccgccccgg gcccaccgc aagcattacc   1080
agccctatgc cccaccacgc gacttcgcag cctatcgctc cagagtgaag ttcagcagga   1140
gcgcagagcc ccccgcgtac cagcagggcc agaaccagct ctataacgag ctcaatctag   1200
gacgaagaga ggagtacgat gttttggaca agagacgtgg ccgggaccct gagatggggg   1260
gaaagccgag aaggaagaac cctcaggaag gcctgtacaa tgaactgcag aaagataaga   1320
tggcggaggc ctacagtgag attgggatga aggcgagcg ccggagggc aaggggcacg   1380
```

```
atggccttta ccagggtctc agtacagcca ccaaggacac ctacgacgcc cttcacatgc    1440
aggccctgcc ccctcgcg                                                  1458
```

<210> SEQ ID NO 5
<211> LENGTH: 223
<212> TYPE: PRT
<213> ORGANISM: Homo sapiens

<400> SEQUENCE: 5

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 6
<211> LENGTH: 288
<212> TYPE: PRT
<213> ORGANISM: Homo sapiens

<400> SEQUENCE: 6

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95
```

```
Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 7
<211> LENGTH: 525
<212> TYPE: PRT
<213> ORGANISM: Homo sapiens

<400> SEQUENCE: 7

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
```

```
                180                 185                 190
Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
        515                 520                 525

<210> SEQ ID NO 8
<211> LENGTH: 370
<212> TYPE: PRT
<213> ORGANISM: Homo sapiens

<400> SEQUENCE: 8

Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Val Ser Ile
            20                  25                  30
```

```
Ser Gly Val Pro Leu Gln Leu Gln Pro Asn Ser Ile Gln Thr Lys Val
        35                  40                  45

Asp Ser Ile Ala Trp Lys Lys Leu Leu Pro Ser Gln Asn Gly Phe His
 50                  55                  60

His Ile Leu Lys Trp Glu Asn Gly Ser Leu Pro Ser Asn Thr Ser Asn
 65                  70                  75                  80

Asp Arg Phe Ser Phe Ile Val Lys Asn Leu Ser Leu Ile Lys Ala
                 85                  90                  95

Ala Gln Gln Gln Asp Ser Gly Leu Tyr Cys Leu Glu Val Thr Ser Ile
            100                 105                 110

Ser Gly Lys Val Gln Thr Ala Thr Phe Gln Val Phe Val Phe Glu Ser
        115                 120                 125

Leu Leu Pro Asp Lys Val Glu Lys Pro Arg Leu Gln Gly Gln Gly Lys
130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Glu Val Asp Ile Asn
            180                 185                 190

Gly Thr His Thr Tyr Thr Cys Asn Val Ser Asn Pro Val Ser Trp Glu
        195                 200                 205

Ser His Thr Leu Asn Leu Thr Gln Asp Cys Gln Asn Ala His Gln Glu
    210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
            260                 265                 270

Asp Val Lys Asp Leu Lys Thr Arg Arg Asn His Glu Gln Glu Gln Thr
        275                 280                 285

Phe Pro Gly Gly Gly Ser Thr Ile Tyr Ser Met Ile Gln Ser Gln Ser
    290                 295                 300

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Arg Asn His Ser Pro Ser
                325                 330                 335

Phe Asn Ser Thr Ile Tyr Glu Val Ile Gly Lys Ser Gln Pro Lys Ala
            340                 345                 350

Gln Asn Pro Ala Arg Leu Ser Arg Lys Glu Leu Glu Asn Phe Asp Val
        355                 360                 365

Tyr Ser
370

<210> SEQ ID NO 9
<211> LENGTH: 289
<212> TYPE: PRT
<213> ORGANISM: Homo sapiens

<400> SEQUENCE: 9

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30
```

-continued

```
Ser Cys Asp Val Gln Leu Tyr Ile Lys Arg Gln Ser Glu His Ser Ile
    35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
        130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 10
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Ala Leu Pro Val Thr Ala Leu Leu Leu Pro Leu Ala Leu Leu Leu
```

|   | 1 |   |   |   | 5 |   |   |   |   | 10 |   |   |   |   | 15 |
|---|---|---|---|---|---|---|---|---|---|---|---|---|---|---|---|

His Ala Ala Arg Pro Ser Gln Phe Arg Val Ser Pro Leu Asp Arg Thr
            20                      25                      30

Trp Asn Leu Gly Glu Thr Val Glu Leu Lys Cys Gln Val Leu Leu Ser
            35                      40                      45

Asn Pro Thr Ser Gly Cys Ser Trp Leu Phe Gln Pro Arg Gly Ala Ala
 50                          55                      60

Ala Ser Pro Thr Phe Leu Leu Tyr Leu Ser Gln Asn Lys Pro Lys Ala
 65                      70                      75                  80

Ala Glu Gly Leu Asp Thr Gln Arg Phe Ser Gly Lys Arg Leu Gly Asp
                    85                      90                      95

Thr Phe Val Leu Thr Leu Ser Asp Phe Arg Arg Glu Asn Glu Gly Tyr
                100                     105                     110

Tyr Phe Cys Ser Ala Leu Ser Asn Ser Ile Met Tyr Phe Ser His Phe
            115                     120                     125

Val Pro Val Phe Leu Pro Ala Lys Pro Thr Thr Thr Pro Ala Pro Arg
 130                     135                     140

Pro Pro Thr Pro Ala Pro Thr Ile Ala Ser Gln Pro Leu Ser Leu Arg
145                     150                     155                     160

Pro Glu Ala Cys Arg Pro Ala Ala Gly Gly Ala Val His Thr Arg Gly
                165                     170                     175

Leu Asp Phe Ala Cys Asp Ile Tyr Ile Trp Ala Pro Leu Ala Gly Thr
            180                     185                     190

Cys Gly Val Leu Leu Leu Ser Leu Val Ile Thr Leu Tyr Cys Asn His
            195                     200                     205

Arg Asn Arg Arg Arg Val Cys Lys Cys Pro Arg Pro Val Val Lys Ser
 210                     215                     220

Gly Asp Lys Pro Ser Leu Ser Ala Arg Tyr Val
225                     230                     235

<210> SEQ ID NO 12
<211> LENGTH: 777
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
atggctctcc cagtgactgc cctactgctt cccctagcgc ttctcctgca tgcagaggtg      60
cagctgcagc agtcaggacc tgaactggtg aagcctggga cttcagtgag gatatcctgc     120
aagacttctg gatacacatt cactgaatat accatacact gggtgaagca gagccatgga     180
aagagccttg agtggattgg aaacatcaat cctaacaatg gtggtaccac ctacaatcag     240
aagttcgagg acaaggccac attgactgta gacaagtcct ccagtacagc ctacatggag     300
ctccgcagcc taacatctga ggattctgca gtctattatt gtgcagctgg ttggaacttt     360
gactactggg gccaagggac cacggtcacc gtctcctcag gtggaggtgg atcaggtgga     420
ggtggatctg gtggaggtgg atctgacatt gtgatgaccc agtctcacaa attcatgtcc     480
acatcagtag gagacagggt cagcatcatc tgtaaggcca gtcaagatgt gggtactgct     540
gtagactggt atcaacagaa accaggacaa tctcctaaac tactgattta ttgggcatcc     600
actcggcaca ctggagtccc tgatcgcttc acaggcagtg gatctgggac agacttcact     660
ctcaccatta ctaatgttca gtctgaagac ttggcagatt atttctgtca gcaatataac     720
agctatcccc tcacgttcgg tgctgggacc atgctggacc tgaaacgggc ggccgca    777

```
<210> SEQ ID NO 13
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13
```

Met Ala Leu Pro Val Thr Ala Leu Leu Pro Leu Ala Leu Leu Leu
1               5                   10                  15

His Ala Glu Val Gln Leu Gln Gln Ser Gly Pro Glu Leu Val Lys Pro
            20                  25                  30

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
    50                  55                  60

Trp Ile Gly Asn Ile Asn Pro Asn Asn Gly Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Gly Ser Gly Gly Gly Ser Gly
    130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
                165                 170                 175

Val Gly Thr Ala Val Asp Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Ser Gly Thr Asp Phe Thr Leu Thr Ile Thr
    210                 215                 220

Asn Val Gln Ser Glu Asp Leu Ala Asp Tyr Phe Cys Gln Gln Tyr Asn
225                 230                 235                 240

Ser Tyr Pro Leu Thr Phe Gly Ala Gly Thr Met Leu Asp Leu Lys Arg
                245                 250                 255

Ala Ala Ala

```
<210> SEQ ID NO 14
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
```
atggctctcc cagtgactgc cctactgctt cccctagcgc ttctcctgca tgcagaggtg    60

```
aagctgcagc agtctggggc tgagctggtg aggcctgggt cctcagtgaa gatttcctgc    120
aaggcttctg gctatgcatt cagtagctac tggatgaact gggtgaagca gaggcctgga    180
cagggtcttg agtggattgg acagatttat cctggagatg gtgatactaa ctacaatgga    240
aagttcaagg gtcaagccac actgactgca gacaaatcct ccagcacagc ctacatgcag    300
ctcagcggcc taacatctga ggactctgcg gtctatttct gtgcaagaaa gaccattagt    360
tcggtagtag atttctactt tgactactgg ggccaaggga ccacggtcac cgtctcctca    420
ggtggaggtg gatcaggtgg aggtggatct ggtggaggtg gatctgacat tgagctcacc    480
cagtctccaa aattcatgtc cacatcagta ggagacaggg tcagcgtcac ctgcaaggcc    540
agtcagaatg tgggtactaa tgtagcctgg tatcaacaga accaggaca atctcctaaa    600 ccactgattt actcggcaac ctaccggaac agtggagtcc ctgatcgctt cacaggcagt    660
ggatctggga cagatttcac tctcaccatc actaacgtgc agtctaaaga cttggcagac    720
tatttctgtc aacaatataa caggtatccg tacacgtccg agggggggac caagctggag    780
atcaaacggg cggccgca                                                  798
```

<210> SEQ ID NO 15
<211> LENGTH: 532
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 15

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220
```

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
            245                 250                 255

Thr Lys Leu Glu Ile Lys Arg Ala Ala Ala Met Ala Leu Pro Val Thr
        260                 265                 270

Ala Leu Leu Leu Pro Leu Ala Leu Leu Leu His Ala Glu Val Lys Leu
        275                 280                 285

Gln Gln Ser Gly Ala Glu Leu Val Arg Pro Gly Ser Ser Val Lys Ile
    290                 295                 300

Ser Cys Lys Ala Ser Gly Tyr Ala Phe Ser Ser Tyr Trp Met Asn Trp
305                 310                 315                 320

Val Lys Gln Arg Pro Gly Gln Gly Leu Glu Trp Ile Gly Gln Ile Tyr
                325                 330                 335

Pro Gly Asp Gly Asp Thr Asn Tyr Asn Gly Lys Phe Lys Gly Gln Ala
            340                 345                 350

Thr Leu Thr Ala Asp Lys Ser Ser Thr Ala Tyr Met Gln Leu Ser
        355                 360                 365

Gly Leu Thr Ser Glu Asp Ser Ala Val Tyr Phe Cys Ala Arg Lys Thr
    370                 375                 380

Ile Ser Ser Val Val Asp Phe Tyr Phe Asp Tyr Trp Gly Gln Gly Thr
385                 390                 395                 400

Thr Val Thr Val Ser Ser Gly Gly Gly Ser Gly Gly Gly Gly Ser
                405                 410                 415

Gly Gly Gly Gly Ser Asp Ile Glu Leu Thr Gln Ser Pro Lys Phe Met
                420                 425                 430

Ser Thr Ser Val Gly Asp Arg Val Ser Val Thr Cys Lys Ala Ser Gln
        435                 440                 445

Asn Val Gly Thr Asn Val Ala Trp Tyr Gln Gln Lys Pro Gly Gln Ser
    450                 455                 460

Pro Lys Pro Leu Ile Tyr Ser Ala Thr Tyr Arg Asn Ser Gly Val Pro
465                 470                 475                 480

Asp Arg Phe Thr Gly Ser Gly Ser Gly Thr Asp Phe Thr Leu Thr Ile
                485                 490                 495

Thr Asn Val Gln Ser Lys Asp Leu Ala Asp Tyr Phe Cys Gln Gln Tyr
            500                 505                 510

Asn Arg Tyr Pro Tyr Thr Ser Gly Gly Gly Thr Lys Leu Glu Ile Lys
        515                 520                 525

Arg Ala Ala Ala
    530

<210> SEQ ID NO 16
<211> LENGTH: 1209
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
atggctctcc cagtgactgc cctactgctt cccctagcgc ttctcctgca tgcagaggtg     60
cagctgcagc agtcaggacc tgaactggtg aagcctggga cttcagtgag gatatcctgc    120
aagacttctg gatacacatt cactgaatat accatacact gggtgaagca gagccatgga    180

-continued

```
aagagccttg agtggattgg aaacatcaat cctaacaatg gtggtaccac ctacaatcag    240
aagttcgagg acaaggccac attgactgta gacaagtcct ccagtacagc ctacatggag    300
ctccgcagcc taacatctga ggattctgca gtctattatt gtgcagctgg ttggaacttt    360
gactactggg gccaagggac cacggtcacc gtctcctcag gtggaggtgg atcaggtgga    420
ggtggatctg gtggaggtgg atctgacatt gtgatgaccc agtctcacaa attcatgtcc    480
acatcagtag gagacagggt cagcatcatc tgtaaggcca gtcaagatgt gggtactgct    540
gtagactggt atcaacagaa accaggacaa tctcctaaac tactgattta ttgggcatcc    600
actcggcaca ctggagtccc tgatcgcttc acaggcagtg gatctgggac agacttcact    660
ctcaccatta ctaatgttca gtctgaagac ttggcagatt atttctgtca gcaatataac    720
agctatcccc tcacgttcgg tgctgggacc atgctggacc tgaaacgggc ggccgcagag    780
agaagggcag aagtgcccac agcccacccc agccccctcac ccaggccagc cggccagttc    840
caaaccctgg tggttggtgt cgtgggcggc ctgctgggca gcctggtgct gctagtctgg    900
gtcctggccg tcatctgctc ccgggccgca cgagggacaa taggagccag cgcaccggc    960 cagcccctga aggaggaccc ctcagccgtg cctgtgttct ctgtggacta tggggagctg    1020
gatttccagt ggcgagagaa gaccccggag ccccccgtgc cctgtgtccc tgagcagacg    1080
gagtatgcca ccattgtctt tcctagcgga atgggcacct catccccgc ccgcaggggc    1140 tcagccgacg gccctcggag tgcccagcca ctgaggcctg aggatggaca ctgctcttgg    1200
cccctctga                                                           1209
```

<210> SEQ ID NO 17
<211> LENGTH: 402
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Met Ala Leu Pro Val Thr Ala Leu Leu Leu Pro Leu Ala Leu Leu Leu
1               5                   10                  15

His Ala Glu Val Gln Leu Gln Gln Ser Gly Pro Glu Leu Val Lys Pro
            20                  25                  30

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
    50                  55                  60

Trp Ile Gly Asn Ile Asn Pro Asn Asn Gly Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Ser Gly Gly Gly Gly Ser Gly
    130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
```

```
                165                 170                 175
Val Gly Thr Ala Val Asp Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Ser Gly Thr Asp Phe Thr Leu Thr Ile Thr
    210                 215                 220

Asn Val Gln Ser Glu Asp Leu Ala Asp Tyr Phe Cys Gln Gln Tyr Asn
225                 230                 235                 240

Ser Tyr Pro Leu Thr Phe Gly Ala Gly Thr Met Leu Asp Leu Lys Arg
                245                 250                 255

Ala Ala Ala Glu Arg Arg Ala Glu Val Pro Thr Ala His Pro Ser Pro
            260                 265                 270

Ser Pro Arg Pro Ala Gly Gln Phe Gln Thr Leu Val Val Gly Val Val
        275                 280                 285

Gly Gly Leu Leu Gly Ser Leu Val Leu Leu Val Trp Val Leu Ala Val
    290                 295                 300

Ile Cys Ser Arg Ala Ala Arg Gly Thr Ile Gly Ala Arg Arg Thr Gly
305                 310                 315                 320

Gln Pro Leu Lys Glu Asp Pro Ser Ala Val Pro Val Phe Ser Val Asp
                325                 330                 335

Tyr Gly Glu Leu Asp Phe Gln Trp Arg Glu Lys Thr Pro Glu Pro Pro
            340                 345                 350

Val Pro Cys Val Pro Glu Gln Thr Glu Tyr Ala Thr Ile Val Phe Pro
        355                 360                 365

Ser Gly Met Gly Thr Ser Ser Pro Ala Arg Arg Gly Ser Ala Asp Gly
    370                 375                 380

Pro Arg Ser Ala Gln Pro Leu Arg Pro Glu Asp Gly His Cys Ser Trp
385                 390                 395                 400

Pro Leu

<210> SEQ ID NO 18
<211> LENGTH: 1029
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
atggctctcc cagtgactgc cctactgctt cccctagcgc ttctcctgca tgcagaggtg      60
cagctgcagc agtcaggacc tgaactggtg aagcctggga cttcagtgag gatatcctgc     120
aagacttctg gatacacatt cactgaatat accatacact gggtgaagca gagccatgga    180
aagagccttg agtggattgg aaacatcaat cctaacaatg gtggtaccac ctacaatcag    240
aagttcgagg acaaggccac attgactgta gacaagtcct ccagtacagc ctacatggag    300
ctccgcagcc taacatctga ggattctgca gtctattatt gtgcagctgg ttggaacttt    360
gactactggg gccaagggac cacggtcacc gtctcctcag gtgaggtgg atcaggtgga    420 ggtggatctg gtggaggtgg atctgacatt gtgatgaccc agtctcacaa attcatgtcc    480
acatcagtag gagacagggt cagcatcatc tgtaaggcca gtcaagatgt gggtactgct    540
gtagactggt atcaacagaa accaggacaa tctcctaaac tactgattta ttgggcatcc    600
actcggcaca ctggagtccc tgatcgcttc acaggcagtg gatctgggac agacttcact    660
```

```
ctcaccatta ctaatgttca gtctgaagac ttggcagatt atttctgtca gcaatataac    720
agctatcccc tcacgttcgg tgctgggacc atgctggacc tgaaacgggc ggccgcactg    780
ggcataggca acggaaccca gatttatgta attgatccag aaccgtgccc agattctgac    840
ttcctcctct ggatccttgc agcagttagt tcggggttgt ttttttatag ctttctcctc    900
acagctgttt ctttgagcaa aatgctaaag aaaagaagcc ctcttacaac agggtctat     960 gtgaaaatgc ccccaacaga gccagaatgt gaaaagcaat ttcagcctta ttttattccc   1020
atcaattga                                                          1029
```

<210> SEQ ID NO 19
<211> LENGTH: 342
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Met Ala Leu Pro Val Thr Ala Leu Leu Leu Pro Leu Ala Leu Leu Leu
1               5                   10                  15

His Ala Glu Val Gln Leu Gln Gln Ser Gly Pro Glu Leu Val Lys Pro
            20                  25                  30

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
    50                  55                  60

Trp Ile Gly Asn Ile Asn Pro Asn Asn Gly Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Gly Ser Gly Gly Gly Ser Gly
    130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
                165                 170                 175

Val Gly Thr Ala Val Asp Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Ser Gly Thr Asp Phe Thr Leu Thr Ile Thr
    210                 215                 220

Asn Val Gln Ser Glu Asp Leu Ala Asp Tyr Phe Cys Gln Gln Tyr Asn
225                 230                 235                 240

Ser Tyr Pro Leu Thr Phe Gly Ala Gly Thr Met Leu Asp Leu Lys Arg
                245                 250                 255

Ala Ala Ala Leu Gly Ile Gly Asn Gly Thr Gln Ile Tyr Val Ile Asp
            260                 265                 270

Pro Glu Pro Cys Pro Asp Ser Asp Phe Leu Leu Trp Ile Leu Ala Ala
```

```
                275                 280                 285
Val Ser Ser Gly Leu Phe Phe Tyr Ser Phe Leu Leu Thr Ala Val Ser
            290                 295                 300

Leu Ser Lys Met Leu Lys Lys Arg Ser Pro Leu Thr Thr Gly Val Tyr
305                 310                 315                 320

Val Lys Met Pro Pro Thr Glu Pro Glu Cys Glu Lys Gln Phe Gln Pro
                325                 330                 335

Tyr Phe Ile Pro Ile Asn
            340

<210> SEQ ID NO 20
<211> LENGTH: 1029
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
atggctctcc cagtgactgc cctactgctt cccctagcgc ttctcctgca tgcagaggtg      60
cagctgcagc agtcaggacc tgaactggtg aagcctggga cttcagtgag gatatcctgc     120
aagacttctg gatacacatt cactgaatat accatacact gggtgaagca gagccatgga     180
aagagccttg agtggattgg aaacatcaat cctaacaatg gtgtaccac ctacaatcag      240 aagttcgagg acaaggccac attgactgta gacaagtcct ccagtacagc ctacatggag     300
ctccgcagcc taacatctga ggattctgca gtctattatt gtgcagctgg ttggaacttt     360
gactactggg gccaagggac cacggtcacc gtctcctcag gtggaggtgg atcaggtgga     420
ggtggatctg gtgaggtgg atctgacatt gtgatgaccc agtctcacaa attcatgtcc      480
acatcagtag gagacagggt cagcatcatc tgtaaggcca gtcaagatgt gggtactgct     540
gtagactggt atcaacagaa accaggacaa tctcctaaac tactgattta ttgggcatcc     600
actcggcaca ctggagtccc tgatcgcttc acaggcagtg gatctgggac agacttcact     660
ctcaccatta ctaatgttca gtctgaagac ttggcagatt atttctgtca gcaatataac     720
agctatcccc tcacgttcgg tgctgggacc atgctggacc tgaaacgggc ggccgcactg     780
ggcataggca acggaaccca gatttatgta attgatccag aaccgtgccc agattctgac     840
ttcctcctct ggatccttgc agcagttagt tcggggttgt tttttttatag ctttctcctc     900 acagctgttt ctttgagcaa aatgctaaag aaaagaagcc ctcttacaac aggggtcggt     960
gtgaaaatgc ccccaacaga gccagaatgt gaaaagcaat tcagccttat ttttattccc    1020
atcaattga                                                            1029

<210> SEQ ID NO 21
<211> LENGTH: 342
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Met Ala Leu Pro Val Thr Ala Leu Leu Leu Pro Leu Ala Leu Leu Leu
1               5                   10                  15

His Ala Glu Val Gln Leu Gln Gln Ser Gly Pro Glu Leu Val Lys Pro
            20                  25                  30
```

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
    50                  55                  60

Trp Ile Gly Asn Ile Asn Pro Asn Asn Gly Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
                165                 170                 175

Val Gly Thr Ala Val Asp Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Ser Gly Thr Asp Phe Thr Leu Thr Ile Thr
    210                 215                 220

Asn Val Gln Ser Glu Asp Leu Ala Asp Tyr Phe Cys Gln Gln Tyr Asn
225                 230                 235                 240

Ser Tyr Pro Leu Thr Phe Gly Ala Gly Thr Met Leu Asp Leu Lys Arg
                245                 250                 255

Ala Ala Ala Leu Gly Ile Gly Asn Gly Thr Gln Ile Tyr Val Ile Asp
            260                 265                 270

Pro Glu Pro Cys Pro Asp Ser Asp Phe Leu Leu Trp Ile Leu Ala Ala
        275                 280                 285

Val Ser Ser Gly Leu Phe Phe Tyr Ser Phe Leu Leu Thr Ala Val Ser
    290                 295                 300

Leu Ser Lys Met Leu Lys Lys Arg Ser Pro Leu Thr Thr Gly Val Gly
305                 310                 315                 320

Val Lys Met Pro Pro Thr Glu Pro Glu Cys Glu Lys Gln Phe Gln Pro
                325                 330                 335

Tyr Phe Ile Pro Ile Asn
            340

<210> SEQ ID NO 22
<211> LENGTH: 1095
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
atggctctcc cagtgactgc cctactgctt ccccctagcgc ttctcctgca tgcagaggtg      60
cagctgcagc agtcaggacc tgaactggtg aagcctggga cttcagtgag gatatcctgc     120
aagacttctg gatacacatt cactgaatat accatacact gggtgaagca gagccatgga     180

```
aagagccttg agtggattgg aaacatcaat cctaacaatg gtggtaccac ctacaatcag    240
aagttcgagg acaaggccac attgactgta gacaagtcct ccagtacagc ctacatggag    300
ctccgcagcc taacatctga ggattctgca gtctattatt gtgcagctgg ttggaacttt    360
gactactggg gccaagggac cacggtcacc gtctcctcag gtggaggtgg atcaggtgga    420
ggtggatctg gtggaggtgg atctgacatt gtgatgaccc agtctcacaa attcatgtcc    480
acatcagtag gagacagggt cagcatcatc tgtaaggcca gtcaagatgt gggtactgct    540
gtagactggt atcaacagaa accaggacaa tctcctaaac tactgattta ttgggcatcc    600
actcggcaca ctggagtccc tgatcgcttc acaggcagtg gatctgggac agacttcact    660
ctcaccatta ctaatgttca gtctgaagac ttggcagatt atttctgtca gcaatataac    720
agctatcccc tcacgttcgg tgctgggacc atgctggacc tgaaacgggc ggccgcactt    780
ggagcagcag tgtacttcac agagctgtct agcccaggtg cccaacgctc tgggagagcc    840
ccaggtgccc tcccagcagg ccacctcctg ctgtttctca tccttggtgt cctttctctg    900
ctccttttgg tgactggagc ctttggcttt cacctttgga agacagtg gcgaccaaga    960 cgattttctg ccttagagca agggattcac cctccgcagg ctcagagcaa gatagaggag   1020
ctggagcaag aaccggagcc ggagccggag ccggaaccgg agcccgagcc cgagcccgag   1080
ccggagcagc tctga                                                    1095
```

<210> SEQ ID NO 23
<211> LENGTH: 364
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Met Ala Leu Pro Val Thr Ala Leu Leu Leu Pro Leu Ala Leu Leu Leu
1               5                   10                  15

His Ala Glu Val Gln Leu Gln Gln Ser Gly Pro Glu Leu Val Lys Pro
            20                  25                  30

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
    50                  55                  60

Trp Ile Gly Asn Ile Asn Pro Asn Asn Gly Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Ser Gly Gly Gly Gly Ser Gly
    130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
                165                 170                 175

Val Gly Thr Ala Val Asp Trp Tyr Gln Gln Lys Pro Gly Gln Ser Pro
            180                 185                 190
```

```
Lys Leu Leu Ile Tyr Trp Ala Ser Thr Arg His Thr Gly Val Pro Asp
        195                 200                 205

Arg Phe Thr Gly Ser Gly Ser Gly Thr Asp Phe Thr Leu Thr Ile Thr
    210                 215                 220

Asn Val Gln Ser Glu Asp Leu Ala Asp Tyr Phe Cys Gln Gln Tyr Asn
225                 230                 235                 240

Ser Tyr Pro Leu Thr Phe Gly Ala Gly Thr Met Leu Asp Leu Lys Arg
            245                 250                 255

Ala Ala Ala Leu Gly Ala Ala Val Tyr Phe Thr Glu Leu Ser Ser Pro
            260                 265                 270

Gly Ala Gln Arg Ser Gly Arg Ala Pro Gly Ala Leu Pro Ala Gly His
            275                 280                 285

Leu Leu Leu Phe Leu Ile Leu Gly Val Leu Ser Leu Leu Leu Leu Val
        290                 295                 300

Thr Gly Ala Phe Gly Phe His Leu Trp Arg Arg Gln Trp Arg Pro Arg
305                 310                 315                 320

Arg Phe Ser Ala Leu Glu Gln Gly Ile His Pro Pro Gln Ala Gln Ser
                325                 330                 335

Lys Ile Glu Glu Leu Glu Gln Glu Pro Glu Pro Glu Pro Glu Pro Glu
            340                 345                 350

Pro Glu Pro Glu Pro Glu Pro Glu Gln Leu
        355                 360

<210> SEQ ID NO 24
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
atggctctcc cagtgactgc cctactgctt cccctagcgc ttctcctgca tgcagaggtg      60
cagctgcagc agtcaggacc tgaactggtg aagcctggga cttcagtgag gatatcctgc    120
aagacttctg gatacacatt cactgaatat accatacact gggtgaagca gagccatgga    180
aagagccttg agtggattgg aaacatcaat cctaacaatg gtggtaccac ctacaatcag    240
aagttcgagg acaaggccac attgactgta gacaagtcct ccagtacagc ctacatggag    300
ctccgcagcc taacatctga ggattctgca gtctattatt gtgcagctgg ttggaacttt    360
gactactggg gccaagggac cacggtcacc gtctcctcag gtggaggtgg atcaggtgga    420
ggtggatctg gtggaggtgg atctgacatt gtgatgaccc agtctcacaa attcatgtcc    480
acatcagtag gagacagggt cagcatcatc tgtaaggcca gtcaagatgt gggtactgct    540
gtagactggt atcaacagaa accaggacaa tctcctaaac tactgattta ttgggcatcc    600
actcggcaca ctggagtccc tgatcgcttc acaggcagtg gatctgggac agacttcact    660
ctcaccatta ctaatgttca gtctgaagac ttggcagatt atttctgtca gcaatataac    720
agctatcccc tcacgttcgg tgctgggacc atgctggacc tgaaacgggc ggccgcagat    780
gtaaaaagtg cctcagaacg accctccaag gacgaaatgg caagcagacc ctggctcctg    840
tatagtttac ttccctttgg gggattgcct ctactcatca ctacctgttt ctgcctgttc    900
tgctgcctga aaggcaccaa ggaaagcaa atgaactct ctgacacagc aggaagggaa    960
attaacctgg ttgatgctca ccttaagagt gagcaaacag aagcaagcac caggcaaaat   1020
```

```
tcccaagtac tgctatcaga aactggaatt tatgataatg accctgacct ttgtttcagg    1080
atgcaggaag ggtctgaagt ttattctaat ccatgcctgg aagaaaacaa accaggcatt    1140
gtttatgctt ccctgaacca ttctgtcatt ggaccgaact caagactggc aagaaatgta    1200
aaagaagcac caacagaata tgcatccata tgtgtgagga gttaa                    1245
```

<210> SEQ ID NO 25
<211> LENGTH: 414
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

```
Met Ala Leu Pro Val Thr Ala Leu Leu Leu Pro Leu Ala Leu Leu Leu
1               5                   10                  15

His Ala Glu Val Gln Leu Gln Gln Ser Gly Pro Glu Leu Val Lys Pro
            20                  25                  30

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
    50                  55                  60

Trp Ile Gly Asn Ile Asn Pro Asn Asn Gly Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Ser Gly Gly Gly Gly Ser Gly
    130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
                165                 170                 175

Val Gly Thr Ala Val Asp Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Ser Gly Thr Asp Phe Thr Leu Thr Ile Thr
    210                 215                 220

Asn Val Gln Ser Glu Asp Leu Ala Asp Tyr Phe Cys Gln Gln Tyr Asn
225                 230                 235                 240

Ser Tyr Pro Leu Thr Phe Gly Ala Gly Thr Met Leu Asp Leu Lys Arg
                245                 250                 255

Ala Ala Ala Asp Val Lys Ser Ala Ser Glu Arg Pro Ser Lys Asp Glu
            260                 265                 270

Met Ala Ser Arg Pro Trp Leu Leu Tyr Ser Leu Leu Pro Leu Gly Gly
        275                 280                 285

Leu Pro Leu Leu Ile Thr Thr Cys Phe Cys Leu Phe Cys Cys Leu Arg
    290                 295                 300

Arg His Gln Gly Lys Gln Asn Glu Leu Ser Asp Thr Ala Gly Arg Glu
```

```
                    305                 310                 315                 320
Ile Asn Leu Val Asp Ala His Leu Lys Ser Glu Gln Thr Glu Ala Ser
                325                 330                 335

Thr Arg Gln Asn Ser Gln Val Leu Leu Ser Glu Thr Gly Ile Tyr Asp
            340                 345                 350

Asn Asp Pro Asp Leu Cys Phe Arg Met Gln Glu Gly Ser Glu Val Tyr
        355                 360                 365

Ser Asn Pro Cys Leu Glu Glu Asn Lys Pro Gly Ile Val Tyr Ala Ser
    370                 375                 380

Leu Asn His Ser Val Ile Gly Pro Asn Ser Arg Leu Ala Arg Asn Val
385                 390                 395                 400

Lys Glu Ala Pro Thr Glu Tyr Ala Ser Ile Cys Val Arg Ser
                405                 410
```

```
<210> SEQ ID NO 26
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
atggctctcc cagtgactgc cctactgctt cccctagcgc ttctcctgca tgcagaggtg      60
cagctgcagc agtcaggacc tgaactggtg aagcctggga cttcagtgag gatatcctgc     120
aagacttctg gatacacatt cactgaatat accatacact gggtgaagca gagccatgga    180
aagagccttg agtggattgg aaacatcaat cctaacaatg gtggtaccac ctacaatcag    240
aagttcgagg acaaggccac attgactgta gacaagtcct ccagtacagc ctacatggag    300
ctccgcagcc taacatctga ggattctgca gtctattatt gtgcagctgg ttggaacttt    360
gactactggg gccaagggac cacggtcacc gtctcctcag gtggaggtgg atcaggtgga    420
ggtggatctg gtggaggtgg atctgacatt gtgatgaccc agtctcacaa attcatgtcc    480
acatcagtag gagacagggt cagcatcatc tgtaaggcca gtcaagatgt gggtactgct    540
gtagactggt atcaacagaa accaggacaa tctcctaaac tactgattta ttgggcatcc    600
actcggcaca ctggagtccc tgatcgcttc acaggcagtg gatctgggac agacttcact    660
ctcaccatta ctaatgttca gtctgaagac ttggcagatt atttctgtca gcaatataac    720
agctatcccc tcacgttcgg tgctgggacc atgctggacc tgaaacgggc ggccgcacag    780
gactgtcaga atgcccatca ggaattcaga ttttggccgt ttttggtgat catcgtgatt    840
ctaagcgcac tgttccttgg caccttgccc tgcttctgtg tgtggaggag aaagaggaag    900
gagaagcagt cagagaccag tcccaaggaa tttttgacaa tttacgaaga tgtcaaggat    960
ctgaaaacca ggagaaatca cgagcaggag cagactttc ctggaggggg gagcaccatc   1020
tactctatga tccagtccca gtcttctgct cccacgtcac aagaacctgc atatacatta   1080
tattcattaa ttcagccttc caggaagtct ggatccagga agaggaacca cagcccttcc   1140
ttcaatagca ctatctatga agtgattgga aagagtcaac ctaaagccca gaaccctgct   1200
cgattgagcc gcaaagagct ggagaacttt gatgtttatt cctag                   1245

<210> SEQ ID NO 27
<211> LENGTH: 414
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 27

```
Met Ala Leu Pro Val Thr Ala Leu Leu Leu Pro Leu Ala Leu Leu Leu
1               5                   10                  15

His Ala Glu Val Gln Leu Gln Gln Ser Gly Pro Glu Leu Val Lys Pro
            20                  25                  30

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
50                  55                  60

Trp Ile Gly Asn Ile Asn Pro Asn Asn Gly Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Gly Ser Gly Gly Gly Gly Ser Gly
130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
                165                 170                 175

Val Gly Thr Ala Val Asp Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Ser Gly Thr Asp Phe Thr Leu Thr Ile Thr
        210                 215                 220

Asn Val Gln Ser Glu Asp Leu Ala Asp Tyr Phe Cys Gln Gln Tyr Asn
225                 230                 235                 240

Ser Tyr Pro Leu Thr Phe Gly Ala Gly Thr Met Leu Asp Leu Lys Arg
                245                 250                 255

Ala Ala Ala Gln Asp Cys Gln Asn Ala His Gln Glu Phe Arg Phe Trp
            260                 265                 270

Pro Phe Leu Val Ile Ile Val Ile Leu Ser Ala Leu Phe Leu Gly Thr
        275                 280                 285

Leu Ala Cys Phe Cys Val Trp Arg Arg Lys Arg Lys Glu Lys Gln Ser
    290                 295                 300

Glu Thr Ser Pro Lys Glu Phe Leu Thr Ile Tyr Glu Asp Val Lys Asp
305                 310                 315                 320

Leu Lys Thr Arg Arg Asn His Glu Gln Glu Gln Thr Phe Pro Gly Gly
                325                 330                 335

Gly Ser Thr Ile Tyr Ser Met Ile Gln Ser Gln Ser Ser Ala Pro Thr
            340                 345                 350

Ser Gln Glu Pro Ala Tyr Thr Leu Tyr Ser Leu Ile Gln Pro Ser Arg
        355                 360                 365

Lys Ser Gly Ser Arg Lys Arg Asn His Ser Pro Ser Phe Asn Ser Thr
        370                 375                 380
```

Ile Tyr Glu Val Ile Gly Lys Ser Gln Pro Lys Ala Gln Asn Pro Ala
385                 390                 395                 400

Arg Leu Ser Arg Lys Glu Leu Glu Asn Phe Asp Val Tyr Ser
            405                 410

<210> SEQ ID NO 28
<211> LENGTH: 1128
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28
atggctctcc cagtgactgc cctactgctt cccctagcgc ttctcctgca tgcagaggtg    60
cagctgcagc agtcaggacc tgaactggtg aagcctggga cttcagtgag gatatcctgc   120
aagacttctg gatacacatt cactgaatat accatacact gggtgaagca gagccatgga   180
aagagccttg agtggattgg aaacatcaat cctaacaatg gtggtaccac ctacaatcag   240
aagttcgagg acaaggccac attgactgta gacaagtcct ccagtacagc ctacatggag   300
ctccgcagcc taacatctga ggattctgca gtctattatt gtgcagctgg ttggaacttt   360
gactactggg gccaagggac cacggtcacc gtctcctcag gtggaggtgg atcaggtgga   420
ggtggatctg gtggaggtgg atctgacatt gtgatgaccc agtctcacaa attcatgtcc   480
acatcagtag gagacagggt cagcatcatc tgtaaggcca gtcaagatgt gggtactgct   540
gtagactggt atcaacagaa accaggacaa tctcctaaac tactgattta ttgggcatcc   600
actcggcaca ctggagtccc tgatcgcttc acaggcagtg gatctgggac agacttcact   660
ctcaccatta ctaatgttca gtctgaagac ttggcagatt atttctgtca gcaatataac   720
agctatcccc tcacgttcgg tgctgggacc atgctggacc tgaaacgggc ggccgcaccc   780
accacgacgc cagcgccgcg accaccaacc ccggcgccca cgatcgcgtc gcagccctg    840 tccctgcgcc cagaggcgtg ccggccagcg gcggggggcg cagtgcacac gagggggctg   900
gacttcgcct gtgatatcta catctgggcg ccctggccg  ggacttgtgg ggtccttctc   960
ctgtcactgg ttatcaccct ttactgcaac cacagagcac cggcggtttc tttgagcaaa  1020
atgctaaaga aagaagccc tcttacaaca ggggtcggtg tgaaaatgcc cccaacagag   1080
ccagaatgtg aaaagcaatt tcagccttat tttattccca tcaattga              1128

<210> SEQ ID NO 29
<211> LENGTH: 375
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Met Ala Leu Pro Val Thr Ala Leu Leu Leu Pro Leu Ala Leu Leu Leu
1               5                   10                  15

His Ala Glu Val Gln Leu Gln Gln Ser Gly Pro Glu Leu Val Lys Pro
            20                  25                  30

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
    50                  55                  60

Trp Ile Gly Asn Ile Asn Pro Asn Gly Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Ser Gly Gly Gly Ser Gly
    130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
                165                 170                 175

Val Gly Thr Ala Val Asp Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Ser Gly Thr Asp Phe Thr Leu Thr Ile Thr
    210                 215                 220

Asn Val Gln Ser Glu Asp Leu Ala Asp Tyr Phe Cys Gln Gln Tyr Asn
225                 230                 235                 240

Ser Tyr Pro Leu Thr Phe Gly Ala Gly Thr Met Leu Asp Leu Lys Arg
                245                 250                 255

Ala Ala Ala Pro Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Asn His Arg Ala Pro Ala Val
                325                 330                 335

Ser Leu Ser Lys Met Leu Lys Lys Arg Ser Pro Leu Thr Thr Gly Val
            340                 345                 350

Gly Val Lys Met Pro Pro Thr Glu Pro Glu Cys Glu Lys Gln Phe Gln
        355                 360                 365

Pro Tyr Phe Ile Pro Ile Asn
    370                 375

<210> SEQ ID NO 30
<211> LENGTH: 1296
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30
atggctctcc cagtgactgc cctactgctt cccctagcgc ttctcctgca tgcagaggtg    60
cagctgcagc agtcaggacc tgaactggtg aagcctggga cttcagtgag gatatcctgc   120
aagacttctg gatacacatt cactgaatat accatacact gggtgaagca gagccatgga   180

```
aagagccttg agtggattgg aaacatcaat cctaacaatg gtggtaccac ctacaatcag    240
aagttcgagg acaaggccac attgactgta gacaagtcct ccagtacagc ctacatggag    300
ctccgcagcc taacatctga ggattctgca gtctattatt gtgcagctgg ttggaacttt    360
gactactggg gccaagggac cacggtcacc gtctcctcag gtggaggtgg atcaggtgga    420
ggtggatctg gtggaggtgg atctgacatt gtgatgaccc agtctcacaa attcatgtcc    480
acatcagtag gagacagggt cagcatcatc tgtaaggcca gtcaagatgt gggtactgct    540
gtagactggt atcaacagaa accaggacaa tctcctaaac tactgattta ttgggcatcc    600
actcggcaca ctggagtccc tgatcgcttc acaggcagtg gatctgggac agacttcact    660
ctcaccatta ctaatgttca gtctgaagac ttggcagatt atttctgtca gcaatataac    720
agctatcccc tcacgttcgg tgctgggacc atgctggacc tgaaacgggc ggccgcaccc    780
accacgacgc cagcgccgcg accaccaacc ccggcgccca cgatcgcgtc gcagcccctg    840
tccctgcgcc cagaggcgtg ccggccagcg gcgggggggcg cagtgcacac gagggggctg    900
gacttcgcct gtgatatcta catctgggcg ccctgccg ggacttgtgg ggtccttctc    960
ctgtcactgg ttatcaccct ttactgcaac cacagaatgc attgctcccg ggccgcacga    1020
gggacaatag gagccaggcg caccggccag cccctgaagg aggaccctc agccgtgcct    1080 gtgttctctg tggactatgg ggagctggat ttccagtggc gagagaagac cccggagccc    1140
cccgtgccct gtgtccctga gcagacggag tatgccacca ttgtctttcc tagcggaatg    1200
ggcacctcat ccccgccccg caggggctca gccgacggcc tcggagtgc ccagccactg    1260 aggcctgagg atggacactg ctcttggccc ctctga                             1296
```

<210> SEQ ID NO 31
<211> LENGTH: 431
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

Met Ala Leu Pro Val Thr Ala Leu Leu Leu Pro Leu Ala Leu Leu Leu
1               5                   10                  15

His Ala Glu Val Gln Leu Gln Gln Ser Gly Pro Glu Leu Val Lys Pro
            20                  25                  30

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
    50                  55                  60

Trp Ile Gly Asn Ile Asn Pro Asn Asn Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Ser Gly Gly Gly Ser Gly
    130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
                165                 170                 175
Val Gly Thr Ala Val Asp Trp Tyr Gln Gln Lys Pro Gly Gln Ser Pro
            180                 185                 190
Lys Leu Leu Ile Tyr Trp Ala Ser Thr Arg His Thr Gly Val Pro Asp
        195                 200                 205
Arg Phe Thr Gly Ser Gly Ser Gly Thr Asp Phe Thr Leu Thr Ile Thr
    210                 215                 220
Asn Val Gln Ser Glu Asp Leu Ala Asp Tyr Phe Cys Gln Gln Tyr Asn
225                 230                 235                 240
Ser Tyr Pro Leu Thr Phe Gly Ala Gly Thr Met Leu Asp Leu Lys Arg
                245                 250                 255
Ala Ala Ala Pro Thr Thr Thr Pro Ala Pro Arg Pro Pro Thr Pro Ala
            260                 265                 270
Pro Thr Ile Ala Ser Gln Pro Leu Ser Leu Arg Pro Glu Ala Cys Arg
        275                 280                 285
Pro Ala Ala Gly Gly Ala Val His Thr Arg Gly Leu Asp Phe Ala Cys
    290                 295                 300
Asp Ile Tyr Ile Trp Ala Pro Leu Ala Gly Thr Cys Gly Val Leu Leu
305                 310                 315                 320
Leu Ser Leu Val Ile Thr Leu Tyr Cys Asn His Arg Met His Cys Ser
                325                 330                 335
Arg Ala Ala Arg Gly Thr Ile Gly Ala Arg Arg Thr Gly Gln Pro Leu
            340                 345                 350
Lys Glu Asp Pro Ser Ala Val Pro Val Phe Ser Val Asp Tyr Gly Glu
        355                 360                 365
Leu Asp Phe Gln Trp Arg Glu Lys Thr Pro Glu Pro Pro Val Pro Cys
    370                 375                 380
Val Pro Glu Gln Thr Glu Tyr Ala Thr Ile Val Phe Pro Ser Gly Met
385                 390                 395                 400
Gly Thr Ser Ser Pro Ala Arg Arg Gly Ser Ala Asp Gly Pro Arg Ser
                405                 410                 415
Ala Gln Pro Leu Arg Pro Glu Asp Gly His Cys Ser Trp Pro Leu
            420                 425                 430

<210> SEQ ID NO 32
<211> LENGTH: 1113
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

| | |
|---|---:|
| atggctctcc cagtgactgc cctactgctt cccctagcgc ttctcctgca tgcagaggtg | 60 |
| cagctgcagc agtcaggacc tgaactggtg aagcctggga cttcagtgag gatatcctgc | 120 |
| aagacttctg gatacacatt cactgaatat accatacact gggtgaagca gagccatgga | 180 |
| aagagccttg agtggattgg aaacatcaat cctaacaatg gtggtaccac ctacaatcag | 240 |
| aagttcgagg acaaggccac attgactgta gacaagtcct ccagtacagc ctacatggag | 300 |
| ctccgcagcc taacatctga ggattctgca gtctattatt gtgcagctgg ttggaacttt | 360 |
| gactactggg gccaagggac cacggtcacc gtctcctcag gtggaggtgg atcaggtgga | 420 |
| ggtggatctg gtggaggtgg atctgacatt gtgatgaccc agtctcacaa attcatgtcc | 480 |

```
acatcagtag gagacagggt cagcatcatc tgtaaggcca gtcaagatgt gggtactgct    540
gtagactggt atcaacagaa accaggacaa tctcctaaac tactgattta ttgggcatcc    600
actcggcaca ctggagtccc tgatcgcttc acaggcagtg gatctgggac agacttcact    660
ctcaccatta ctaatgttca gtctgaagac ttggcagatt atttctgtca gcaatataac    720
agctatcccc tcacgttcgg tgctgggacc atgctggacc tgaaacgggc ggccgcaccc    780
accacgacgc cagcgccgcg accaccaacc ccggcgccca cgatcgcgtc gcagcccctg    840
tccctgcgcc cagaggcgtg ccggccagcg gcggggggcg cagtgcacac gaggggggctg    900 gacttcgcct gtgatatcta catctgggcg ccctggccg ggacttgtgg ggtccttctc    960
ctgtcactgg ttatcaccct ttactgcaac cacagagcac cggcgatgct aaagaaaaga   1020
agccctctta caacaggggt ctatgtgaaa atgcccccaa cagagccaga atgtgaaaag   1080
caatttcagc cttattttat tcccatcaat tga                                1113

<210> SEQ ID NO 33
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Ala Leu Pro Val Thr Ala Leu Leu Leu Pro Leu Ala Leu Leu Leu
1               5                   10                  15

His Ala Glu Val Gln Leu Gln Gln Ser Gly Pro Glu Leu Val Lys Pro
            20                  25                  30

Gly Thr Ser Val Arg Ile Ser Cys Lys Thr Ser Gly Tyr Thr Phe Thr
        35                  40                  45

Glu Tyr Thr Ile His Trp Val Lys Gln Ser His Gly Lys Ser Leu Glu
    50                  55                  60

Trp Ile Gly Asn Ile Asn Pro Asn Asn Gly Gly Thr Thr Tyr Asn Gln
65                  70                  75                  80

Lys Phe Glu Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Ala Gly Trp Asn Phe Asp Tyr Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser His Lys Phe Met Ser
145                 150                 155                 160

Thr Ser Val Gly Asp Arg Val Ser Ile Ile Cys Lys Ala Ser Gln Asp
                165                 170                 175

Val Gly Thr Ala Val Asp Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Ser Gly Thr Asp Phe Thr Leu Thr Ile Thr
    210                 215                 220

Asn Val Gln Ser Glu Asp Leu Ala Asp Tyr Phe Cys Gln Gln Tyr Asn
225                 230                 235                 240
```

```
Ser Tyr Pro Leu Thr Phe Gly Ala Gly Thr Met Leu Asp Leu Lys Arg
            245                 250                 255

Ala Ala Ala Pro Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
        290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Asn His Arg Ala Pro Ala Met
                325                 330                 335

Leu Lys Lys Arg Ser Pro Leu Thr Thr Gly Val Tyr Val Lys Met Pro
            340                 345                 350

Pro Thr Glu Pro Glu Cys Glu Lys Gln Phe Gln Pro Tyr Phe Ile Pro
            355                 360                 365

Ile Asn
    370

<210> SEQ ID NO 34
<211> LENGTH: 4
<212> TYPE: PRT
<213> ORGANISM: Homo sapiens

<400> SEQUENCE: 34

Tyr Val Lys Met
1
```

COMPOSITIONS AND METHODS FOR IMMUNOTHERAPY

PRIORITY CLAIM

This application is a continuation of International Patent Application No. PCT/US2014/030671 filed, Mar. 17, 2014 and claims priority to U.S. Provisional Application No. 61/802,118, filed Mar. 15, 2013, to both of which priority is claimed and the contents of both of which are incorporated herein in their entireties.

GRANT INFORMATION

This invention was made with government support under grant number GM007739 awarded by the National Institutes of Health. The government has certain rights in the invention.

INTRODUCTION

The present invention provides immunoresponsive cells including an antigen recognizing receptor that binds a first antigen and an inhibitory chimeric antigen receptor (iCAR) that binds a second antigen, where the binding of the antigen recognizing receptor to the first antigen activates the immunoresponsive cell, and the binding of the iCAR to the second antigen inhibits the immunoresponsive cell. The present invention also provides methods of producing the immunoresponsive cells, and methods of treating cancers by using the immunoresponsive cells.

BACKGROUND OF THE INVENTION

T-cell based therapies have curative potential in bone marrow and organ transplantation, cancer immunotherapy, viral infections, and autoimmune diseases. However, major treatment-related complications stem from unintended T-cell reactivity against normal tissues, such as in graft-versus-host disease (GVHD) following donor lymphocyte infusion or "on-target, off-tumor reactivity" in autologous targeted T-cell therapy.

The use of donor lymphocyte infusion (DLI) in allogeneic bone marrow transplants (BMT; 25,000 annually worldwide) has produced significant curative gains in certain patient subsets. Recently, DLI has been shown to provide effective therapy for patients with metastatic renal cell carcinoma, breast, colon, and ovarian cancer, with trials under way to treat metastatic solid tumors. The key efficacy of DLI, referred to as graft versus leukemia (GVL) in the context of hematological malignancies, is limited by the induction of both acute and chronic graft versus host disease (GVHD) (rates in excess of 40%), to such an extent that several groups have concluded the current scheme of DLI cannot improve survival unless a decrease in GVHD induction is achieved.

Likewise, cancer immunotherapy trials have reported "on-target but off-tissue" adverse events from TCR and CAR engineered T cells, including for example, B-cell aplasia in chronic lymphocytic leukemia (CLL) patients treated with cells expressing anti-CD19 CAR, fatal acute respiratory distress syndrome (ARDS) from anti-ERBB2 CAR T cell cross reactivity on lung epithelium, and fatalities from cardiac myonecrosis in melanoma and myeloma patients treated with a Mage-A3 TCR.

Non-specific immunosuppression and T-cell elimination are currently the only means to control undesirable T-cell responses, at the cost of abrogating therapeutic benefit and causing serious secondary complications. They rely on the appearance of symptoms, which can be severe and occasionally unmanageable, thus, limiting the use of an otherwise efficacious cellular treatment.

Strategies to prevent the consequences of cellular side effects are acutely needed Current approaches fail to utilize the higher order complexity of T-cell therapies, as an advantage in controlling undesirable side effects. Accordingly, novel therapeutic strategies are urgently required.

SUMMARY OF THE INVENTION

The present invention generally provides immunoresponsive cells (e.g., T cells, Natural Killer (NK) cells, cytotoxic T lymphocytes (CTLs), and regulatory T cells), expressing an antigen binding receptor (e.g., CAR or TCR) having immune cell activating activity and an inhibitory chimeric antigen receptor (iCAR) that selectively reduces or eliminates the immune activity of the immunoresponsive cell. Thus, off-target effects of the immunoresponsive cell are reduced. In some embodiments, the decrease in immune activity is reversible. Accordingly, the invention provides methods of using such immunoresponsive cells for the treatment of neoplasia, infectious disease, and other pathologies.

In one aspect, the invention provides an isolated immunoresponsive cell including an antigen recognizing receptor that binds a first antigen, where the binding activates the immunoresponsive cell, and an inhibitory chimeric antigen receptor that binds a second antigen, where the binding inhibits the immunoresponsive cell.

In another aspect, the invention provides a method of reducing tumor burden in a subject, the method involving administering an effective amount of an immunoresponsive cell including an antigen recognizing receptor that binds a first antigen, where the binding activates the immunoresponsive cell, and an inhibitory chimeric antigen receptor that binds a second antigen, where the binding inhibits the immunoresponsive cell, thereby inducing tumor cell death in the subject. The method can selectively target tumor cells compared to non-tumor cells. In some embodiments, the method reduces the number of tumor cells. In some embodiments, the method reduces tumor size. In other embodiments, the method eradicates the tumor in the subject.

In another aspect, the invention provides a method of increasing survival of a subject having neoplasia, the method involving administering an effective amount of an immunoresponsive cell including an antigen recognizing receptor that binds a first antigen, where the binding activates the immunoresponsive cell, and an inhibitory chimeric antigen receptor that binds a second antigen, where the binding inhibits the immunoresponsive cell, thereby treating or preventing a neoplasia in the subject. In certain embodiments, the neoplasia is selected from the group consisting of blood cancer, B cell leukemia, multiple myeloma, lymphoblastic leukemia (ALL), chronic lymphocytic leukemia, non-Hodgkin's lymphoma, ovarian cancer, prostate cancer, pancreatic cancer, lung cancer, breast cancer, sarcoma, and acute myeloid leukemia (AML).

In another aspect, the invention provides a method for producing an antigen specific immunoresponsive cell that includes an antigen recognizing receptor that binds a first antigen, the method involving introducing into the immunoresponsive cell a nucleic acid sequence that encodes an inhibitory chimeric antigen receptor that binds a second antigen, where the binding inhibits the immunoresponsive cell.

In another aspect the invention provides an inhibitory chimeric antigen receptor (iCAR) including an extracellular domain that binds an antigen; a transmembrane domain operably linked to the extracellular domain; and an intracellular domain that activates intracellular signaling to decrease an immune response, the intracellular domain operably linked to the transmembrane domain. In some embodiments, the intracellular signaling domain is selected from the group consisting of a CTLA-4 polypeptide, a PD-1 polypeptide, a LAG-3 polypeptide, a 2B4 polypeptide, and a BTLA polypeptide. In certain embodiments, the transmembrane domain is selected from the group consisting of a CD4 polypeptide, a CD8 polypeptide, a CTLA-4 polypeptide, a PD-1 polypeptide, a LAG-3 polypeptide, a 2B4 polypeptide, and a BTLA polypeptide. Additionally, the inhibitory chimeric antigen receptor (iCAR) can further comprise a Fab, scFv, ligand, specific ligand, or polyvalent ligand. In some embodiments, the binding of an antigen to the iCAR activates the intracellular signaling domain that decreases an immune response.

In a related aspect, the invention provides a nucleic acid sequence encoding an inhibitory chimeric antigen receptor that binds an antigen, where the binding activates an intracellular signaling domain that decreases an immune response.

In another related aspect, the invention provides a vector including a nucleic acid sequence encoding an inhibitory chimeric antigen receptor that binds an antigen, where the binding activates an intracellular signaling domain that decreases an immune response.

In a related aspect, the invention provides a pharmaceutical composition (for the treatment of a neoplasia or pathogen infection) including an effective amount of an immunoresponsive cell of the invention in a pharmaceutically acceptable excipient.

In another aspect, the invention provides a kit for treatment of a neoplasia, pathogen infection, an autoimmune disorder, or an allogeneic transplant, the kit including an immunoresponsive cell that includes an antigen recognizing receptor that binds a first antigen and activates the immunoresponsive cell, and an inhibitory chimeric antigen receptor that binds a second antigen and inhibits the immunoresponsive cell. In various embodiments, the kit further includes written instructions for using said cell for the treatment of a subject having a neoplasia, a pathogen infection, an autoimmune disorder, or an allogeneic transplant.

In another aspect, the invention provides a method of modulating a graft versus leukemia response or graft versus tumor response in a subject, the method involving administering an effective amount of an immunoresponsive cell allogeneic to the subject including an inhibitory chimeric antigen receptor that binds an antigen, where the binding inhibits the allogeneic immunoresponsive cell, thereby modulating a graft versus leukemia response or graft versus tumor response in the subject. In certain embodiments, the subject has metastatic breast cancer, hematological malignancy, or a solid tumor, and the human leukocyte antigen (HLA) is HLA-I. In certain embodiments, the subject has a tumor that has undergone epithelium to mesenchymal transition (EMT), and the antigen is one or more of an Epithelial-mesenchymal transition (EMT) antigen, E-cadherin, and cytokeratin. In various embodiments, the binding of the inhibitory chimeric antigen receptor and the antigen, decreases cell death in a cell comprising the antigen. The method can reduce graft versus host disease (GVHD) in the subject, or a symptom thereof.

In various embodiments of the aspects delineated herein, the first antigen or antigen of the antigen recognizing receptor is a tumor or pathogen antigen. In particular embodiments, the antigen of the antigen recognizing receptor is one or more tumor antigen selected from the following group consisting of CD19, CAIX, CEA, CD5, CD7, CD10, CD20, CD22, CD30, CD33, CD34, CD38, CD41, CD44, CD49f, CD56, CD74, CD123, CD133, CD138, a cytomegalovirus (CMV) infected cell antigen, EGP-2, EGP-40, EpCAM, erb-B2,3,4, F8P, Fetal acetylcholine receptor, folate receptor-a, GD2, GD3, HER-2, hTERT, IL-13R-α2, κ-light chain, KDR, LeY, L1 cell adhesion molecule, MAGE-A1, Mesothelin, Muc-1, Muc-16, NKG2D ligands, NY-ESO-1, oncofetal antigen (h5T4), PSCA, PSMA, ROR1, TAG-72, VEGF-R2, and WT-1.

In various embodiments of the aspects delineated herein, the second antigen or antigen of the inhibitory chimeric antigen receptor is CD33, CD38, a human leukocyte antigen (HLA), an organ specific antigen, a blood-brain barrier specific antigen, an Epithelial-mesenchymal transition (EMT) antigen, E-cadherin, cytokeratin, Opioid-binding protein/cell adhesion molecule (OPCML), HYLA2, Deleted in Colorectal Carcinoma (DCC), Scaffold/Matrix attachment region-binding protein 1 (SMAR1), cell surface carbohydrate, or mucin type O-glycan. In various embodiments of the aspects delineated herein, the binding of an antigen to the iCAR activates the intracellular signaling domain that decreases an immune response.

In various embodiments of the aspects delineated herein, the inhibitory chimeric antigen receptor is recombinantly expressed. In various embodiments of the aspects delineated herein, the inhibitory chimeric antigen receptor is expressed from a vector. In various embodiments of the aspects delineated herein, the inhibitory chimeric antigen receptor (iCAR) includes an intracellular signaling domain selected from the group consisting of a CTLA-4 polypeptide, a PD-1 polypeptide, a LAG-3 polypeptide, a 2B4 polypeptide, and a BTLA polypeptide. In various embodiments of the aspects delineated herein, the inhibitory chimeric antigen receptor (iCAR) includes a transmembrane domain selected from the group consisting of a CD4 polypeptide, a CD8 polypeptide, a CTLA-4 polypeptide, a PD-1 polypeptide, a LAG-3 polypeptide, a 2B4 polypeptide, and a BTLA polypeptide. In various embodiments of the aspects delineated herein, the inhibitory chimeric antigen receptor (iCAR) includes a Fab, scFv, ligand, specific ligand, or polyvalent ligand. In certain embodiments, the cell expresses a recombinant or an endogenous antigen receptor that is selected from the group consisting of 19-28z, P28z, M28z, and 56-28z.

In various embodiments of the aspects delineated herein, the antigen recognizing receptor is a T cell receptor (TCR) or chimeric antigen receptor (CAR). In various embodiments of the aspects delineated herein, antigen recognizing receptor is exogenous or endogenous. In various embodiments of the aspects delineated herein, antigen recognizing receptor is recombinantly expressed. In various embodiments of the aspects delineated herein, the antigen recognizing receptor is expressed from a vector. In various embodiments of any of the aspects delineated herein, an allogeneic cell has an endogenous T cell receptor.

In various embodiments of the aspects delineated herein, the cell is one or more of a T cell, a Natural Killer (NK) cell, a cytotoxic T lymphocyte (CTL), a regulatory T cell, a human embryonic stem cell, a cell of the innate immune system, and a pluripotent stem cell from which lymphoid cells may be differentiated. In some embodiments, the immunoresponsive cell is autologous. In other embodiments, the immunoresponsive cell is non-autologous.

DEFINITIONS

Unless defined otherwise, all technical and scientific terms used herein have the meaning commonly understood by a person skilled in the art to which this invent ion belongs. The following references provide one of skill with a general definition of many of the terms used in this invention: Singleton et al., Dictionary of Microbiology and Molecular Biology (2nd ed. 1994); The Cam bridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds antigen, a formation of an immunological synapse occurs that includes clustering of many molecules near the bound receptor (e.g. CD4 or CD8, CD3γ/δ/ε/ζ, etc.) This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response. By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), OX40, and ICOS. Without being bound to a particular theory, receiving multiple stimulatory signals is important to mount a robust and long-term T cell mediated immune response. Without receiving these stimulatory signals, T cells quickly become inhibited and unresponsive to antigen. While the effects of these co-stimulatory signals vary and remain partially understood, they generally result in increasing gene expression in order to generate long lived, proliferative, and anti-apoptotic T cells that robustly respond to antigen for complete and sustained eradication.

The term "antigen recognizing receptor" as used herein refers to a receptor that is capable of activating an immune cell (e.g., a T-cell) in response to antigen binding. Exemplary antigen recognizing receptors may be native or endogenous T cell receptors, exogenous T cell receptors introduced into a cell and/or chimeric antigen receptors in which a tumor antigen-binding domain is fused to an intracellular signaling domain capable of activating an immune cell (e.g., a T-cell).

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., *J Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

By "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, including use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

The term "chimeric antigen receptor" or "CAR" as used herein refers to an antigen-binding domain that is fused to an intracellular signaling domain capable of activating or stimulating an immune cell. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries). In various embodiments, this scFv is fused to a transmembrane domain and then to an intracellular signaling domain. "First generation" CARs include those that solely provide CD3ζ signals upon antigen binding, "Second generation" CARs include those that provide both costimulation (e.g. CD28 or CD137) and activation (CD3ζ). "Third-generation" CARs include those that provide multiple costimulation (e.g. CD28 and CD137) and activation (CD3ζ). In various embodiments, the CAR is selected to have high affinity or avidity for the antigen.

The term "inhibitory chimeric antigen receptor" or "iCAR" as used herein refers to an antigen-binding domain that is fused to an intracellular signaling domain capable of inhibiting or suppressing the immune activity of an immune cell. iCARs have immune cell inhibitory potential, and are distinct and distinguishable from CARs, which are receptors with immune cell activating potential. For example, CARs are activating receptors as they include CD3ζ, iCARs do not contain activating domains. Thus, iCARs are distinct from CARs and are not a subgroup of CARs. In certain embodiments, the antigen-binding domain is fused to a transmembrane domain and the intracellular domain(s) of an immunoinhibitory receptor. The transmembrane domain of the iCAR can be a CD8 polypeptide, a CD4 polypeptide, a CTLA-4 polypeptide, a PD-1 polypeptide, a LAG-3 polypeptide, a 2B4 polypeptide, or a BTLA polypeptide. The intracellular domain of the iCAR can be a CTLA-4 polypeptide, a PD-1 polypeptide, a LAG-3 polypeptide, a 2B4 polypeptide, or a BTLA polypeptide. In various embodiments, the iCAR's extracellular binding domain is composed of a single chain variable fragment (scFv) derived from fusing the variable heavy and light regions of a murine or humanized monoclonal antibody. In certain embodiments, the scFV is an scFV specific for prostate-specific membrane antigen (PSMA). Alternatively, scFvs may be used that are derived from Fab's (instead of from an antibody, e.g., obtained from Fab libraries). iCARs have immunosuppressive activity that inhibits T-cell function specifically upon antigen recognition.

By "inhibits an immunoresponsive cell" or "suppresses an immunoresponsive cell" is meant induction of signal transduction or changes in protein expression in the cell resulting in suppression of an immune response (e.g., decrease in cytokine production). In preferred embodiments, inhibition or suppression of an immunoresponsive cell is selective and/or reversible.

The term "immunosuppressive activity" is meant induction of signal transduction or changes in protein expression in a cell (e.g., an activated immunoresponsive cell) resulting in a decrease in an immune response. Polypeptides known to suppress or decrease an immune response include, but are not limited to, CTLA-4 polypeptides, PD-1 polypeptides, LAG-3 polypeptides, 2B4 polypeptides, or BTLA polypeptides (e.g., via binding to their corresponding ligands). At a minimum, iCAR signaling uses the intracellular portions of such molecules and can also include portions of the transmembrane domain and/or extracellular domain of said molecules as necessary to produce a functional iCAR. The term "immunostimulatory activity" is meant induction of signal transduction or changes in protein expression in a cell (e.g., an activated immunoresponsive cell) resulting in an increase in an immune response. Immunostimulatory activity may include pro-inflammatory activity. Polypeptides known to stimulate or increase an immune response via their binding include CD28, OX-40, 4-1BB, and their corresponding ligands, including B7-1, B7-2, OX-40L, and 4-1BBL. Such polypeptides are present in the tumor microenvironment and activate immune responses to neoplastic cells. In various embodiments, promoting, stimulating, or agonizing pro-inflammatory polypeptides and/or their ligands enhances the immune response of the immunoresponsive cell.

By "CD3ζ polypeptide" is meant a protein having at least 85, 90, 95, 96, 97, 98, 99 or 100% identity to NCBI Reference No: NP_932170 or a fragment thereof that has activating or stimulatory activity. An exemplary CD3ζ is provided below [SEQ ID NO:1].

```
  1 mkwkalftaa ilqaqlpite aqsfglldpk lcylldgilf iygviltalf lrvkfsrsad
 61 apayqqgqnq lynelnlgrr eeydvldkrr grdpemggkp grrknpqegl ynelqkdkma
121 eayseigmkg errrgkghdg lyqglstatk dtydalhmga lppr
```

By "CD3ζ nucleic acid molecule" is meant a polynucleotide encoding a CD3ζ polypeptide.

By "CD28 polypeptide" is meant a protein having at least 85, 90, 95, 96, 97, 98, 99 or 100% identity to NCBI Reference No: NP_006130 or a fragment thereof that has stimulatory activity. An exemplary CD28 is provided below [SEQ ID NO:2].

```
  1 mlrlllalnl fpsiqvtgnk ilvkqspmlv aydnavnlsc kysynlfsre fraslhkgld
 61 savevcvvyg nysqqlqvys ktgfncdgkl gnesvtfylq nlyvnqtdiy fckievmypp
121 pyldneksng tiihvkgkhl cpsplfpgps kpfwvlvvvg gvlacysllv tvafiifwvr
181 skrsrllhsd ymnmtprrpg ptrkhyqpya pprdfaayrs
```

By "CD28 nucleic acid molecule" is meant a polynucleotide encoding a CD28 polypeptide.

By "19-28z" is meant a protein having at least 85, 90, 95, 96, 97, 98, 99 or 100% identity to the sequence provided below [SEQ ID NO:3], which includes a leader sequence at amino acids 1-18, and is able to bind CD19.

```
MALPVTALLLPLALLLHAEVKLQQSGAELVRPGSSVKISCKASGYAFSS
YWMNWVKQRPGQGLEWIGQIYPGDGDTNYNGKFKGQATLTADKSSSTAY
MQLSGLTSEDSAVYFCARKTISSVVDFYFDYWGQGTTVTVSSGGGGSGG
GGSGGGGSDIELTQSPKFMSTSVGDRVSVTCKASQNVGTNVAWYQQKPG
QSPKPLIYSATYRNSGVPDRFTGSGSGTDFTLTITNVQSKDLADYFCQQ
YNRYPYTSGGGTKLEIKRAAAIEVMYPPPYLDNEKENGTIIHVKGKHLC
PSPLFPGPSKPFWVLVVVGGVLACYSLLVTVAFIIFWVRSKRSRLLHSD
YMNMTPRRPGPTRKHYQPYAPPRDFAAYRSRVKFSRSAEPPAYQQGQNQ
LYNELNLGRREEYDVLDKRRGRDPEMGGKPRRKNPQEGLYNELQKDKMA
EAYSEIGMKGERRRGKGHDGLYQGLSTATKDTYDALHMQALPPRX
```

An exemplary nucleic acid sequence encoding a 19-28z polypeptide, including a leader sequence, is provided below [SEQ ID NO:4].

```
ccatggctctcccagtgactgccctactgcttccoctagcgcttctcctg
catgcagaggtgaagctgcagcagtctggggctgagctggtgaggcctgg
gtcctcagtgaagatttcctgcaaggcttctggctatgcattcagtagct
actggatgaactgggtgaagcagaggcctggacagggtcttgagtggatt
ggacagatttatcctggagatggtgatactaactacaatggaaagttcaa
gggtcaagccacactgactgcagacaaatcctccagcacagcctacatgc
agctcagcggcctaacatctgaggactctgcggtctatttctgtgcaaga
aagaccattagttcggtagtagatttctactttgactactggggccaagg
gaccacggtcaccgtctcctcaggtggaggtggatcaggtggaggtggat
```

-continued

```
ctggtggaggtggatctgacattgagctcacccagtctccaaaattcatg
tccacatcagtaggagacagggtcagcgtcacctgcaaggccagtcagaa
```

-continued

```
tgtgggtactaatgtagcctggtatcaacagaaaccaggacaatctccta
aaccactgatttactcggcaacctaccggaacagtggagtccctgatcgc
ttcacaggcagtggatctgggacagatttcactctcaccatcactaacgt
gcagtctaaagacttggcagactatttctgtcaacaatataacaggtatc
cgtacacgtccggaggggggaccaagctggagatcaaacgggcggccgca
attgaagttatgtatcctcctccttacctagacaatgagaagagcaatgg
aaccattatccatgtgaaagggaaacacctttgtccaagtccctatttc
ccggaccttctaagcccttttgggtgctggtggtggttggtggagtcctg
gcttgctatagcttgctagtaacagtggcctttattattttctgggtgag
gagtaagaggagcaggctcctgcacagtgactacatgaacatgactcccc
gccgcccgggcccaccgcaagcattaccagccctatgcccaccacgc
gacttcgcagcctatcgctccagagtgaagttcagcaggagcgcagagcc
ccccgcgtaccagcagggccagaaccagctctataacgagctcaatctag
gacgaagagaggagtacgatgttttggacaagagacgtggccgggaccct
gagatgggggaaagccgagaaggaagaaccctcaggaaggcctgtacaa
tgaactgcagaaagataagatggcggaggcctacagtgagattgggatga
aaggcgagcgccggaggggcaaggggcacgatggcctttaccagggtctc
agtacagccaccaaggacacctacgacgccttcacatgcaggccctgcc
ccctcgcg
```

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA. 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sam brook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "analog" is meant a structurally related polypeptide or nucleic acid molecule having the function of a reference polypeptide or nucleic acid molecule.

The term "ligand" as used herein refers to a molecule that binds to a receptor. In particular, the ligand binds a receptor on another cell, allowing for cell-to-cell recognition and/or interaction.

The term "constitutive expression" as used herein refers to expression under all physiological conditions.

By "disease" is meant any condition or disorder that damages or interferes with the normal function of a cell, tissue, or organ. Examples of diseases include neoplasia or pathogen infection of cell.

By "effective amount" is meant an amount sufficient to have a therapeutic effect. In one embodiment, an "effective amount" is an amount sufficient to arrest, ameliorate, or inhibit the continued proliferation, growth, or metastasis (e.g., invasion, or migration) of a neoplasia.

By "endogenous" is meant a nucleic acid molecule or polypeptide that is normally expressed in a cell or tissue.

By "enforcing tolerance" is meant preventing the activity of self-reactive cells or immunoresponsive cells that target transplanted organs or tissues.

By "exogenous" is meant a nucleic acid molecule or polypeptide that is not endogenously present in the cell, or not present at a level sufficient to achieve the functional effects obtained when over-expressed. The term "exogenous" would therefore encompass any recombinant nucleic acid molecule or polypeptide expressed in a cell, such as foreign, heterologous, and over-expressed nucleic acid molecules and polypeptides.

By a "heterologous nucleic acid molecule or polypeptide" is meant a nucleic acid molecule (e.g., acDNA, DNA or RNA molecule) or polypeptide that is not normally present in a cell or sample obtained from a cell. This nucleic acid may be from another organism, or it may be, for example, an mRNA molecule that is not normally expressed in a cell or sample.

By "immunoresponsive cell" is meant a cell that functions in an immune response or a progenitor, or progeny thereof.

By "increase" is meant to alter positively by at least 5%. An alteration may be by 5%, 10%, 25%, 30%, 50%, 75%, or even by 100%.

By "isolated cell" is meant a cell that is separated from the molecular and/or cellular components that naturally accompany the cell.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

The term "tumor antigen-binding domain" as used herein refers to a domain capable of specifically binding a particular antigenic determinant or set of antigenic determinants present on a tumor.

The term "obtaining" as in "obtaining the agent" is intended to include purchasing, synthesizing or otherwise acquiring the agent (or indicated substance or material).

"Linker", as used herein, shall mean a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). An exemplary linker sequence used in the invention is GGGGSGGGGSGGGGS [SEQ ID NO:10].

By "modulate" is meant positively or negatively alter. Exemplary modulations include a 1%, 2%, 5%, 10%, 25%, 50%, 75%, or 100% change.

By "neoplasia" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells). Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

By "operably linked", as used herein, is meant the linking of two or more biomolecules so that the biological functions, activities, and/or structure associated with the biomolecules are at least retained. In reference to polypeptides, the term means that the linking of two or more polypeptides results in a fusion polypeptide that retains at least some of the respective individual activities of each polypeptide component. The two or more polypeptides may be linked directly or via a linker. In reference to nucleic acids, the term means that a first polynucleotide is positioned adjacent to a second polynucleotide that directs transcription of the first polynucleotide when appropriate molecules (e.g., transcriptional activator proteins) are bound to the second polynucleotide.

By "pathogen" is meant a virus, bacteria, fungi, parasite or protozoa capable of causing disease.

Exemplary viruses include, but are not limited to, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and lridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Exemplary bacteria include, but are not limited to, *Pasteurella*, *Staphylococci*, *Streptococcus*, *Escherichia coli*, *Pseudomonas* species, and *Salmonella* species. Specific examples of infectious bacteria include but are not limited to, *Helicobacter pyloris*, *Borelia burgdoiferi*, *Legionella pneumophilia*, *Mycobacteria* sps (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcuspyogenes* (Group A *Streptococcus*), *Streptococcus agalactiae* (Group B *Streptococcus*), *Streptococcus* (viridans group), *Streptococcus faecalis*, *Streptococcus hovis*, *Streptococcus* (anaerobic sps.), *Streptococcus pneumoniae*, pathogenic *Campylobacter* sp., *Enterococcus* sp., *Haemophilus influenzae*, *Bacillus antracis*, *corynebacterium diphtheriae*, *corynebacterium* sp., *Erysipelothrix rhusiopathiae*, *Clostridium perfringers*, *Clostridium tetani*, *Enterobacter aerogenes*, *Klebsiella pneumoniae*, *Pasteurella multocida*, *Bacteroides* sp., *Fusobacterium nucleatum*, *Streptobacillus moniliformis*, *Treponema pallidium*, *Treponema pertenue*, *Leptospira*, *Rickettsia*, and *Actinomyces israelli*.

By "receptor" is meant a polypeptide, or portion thereof, present on a cell membrane that selectively binds one or more ligand.

By "reduce" is meant to alter negatively by at least 5%. An alteration may be by 5%, 10%, 25%, 30%, 50%, 75%, or even by 100%.

By "recognize" is meant selectively binds a target. A T cell that recognizes a virus typically expresses a receptor that binds an antigen expressed by the virus.

By "reference" or "control" is meant a standard of comparison. For example, the immune response of a cell expressing a CAR and an iCAR may be compared to the immune response of a corresponding cell expressing CAR alone.

As used herein, the term "single-chain variable fragment" or "scFv" is a fusion protein of the variable regions of the heavy (VH) and light chains (VL) of an immunoglobulin covalently linked to form a VH::VL heterodimer. The heavy (VH) and light chains (VL) are either joined directly or joined by a peptide-encoding linker (e.g., 10, 15, 20, 25 amino acids), which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

By "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

By "signal sequence" or "leader sequence" is meant a peptide sequence (5, 10, 15, 20, 25, 30 amino acids long) present at the N-terminus of newly synthesized proteins that directs their entry to the secretory pathway.

By "soluble" is meant a polypeptide that is freely diffusible in an aqueous environment (e.g., not membrane bound).

By "specifically binds" is meant a polypeptide or fragment thereof that recognizes and binds a biological molecule of interest (e.g., a polypeptide), but which does not substantially recognize and bind other molecules in a sample, for example, a biological sample, which naturally includes a polypeptide of the invention.

The term "tumor antigen" as used herein refers to an antigen (e.g., a polypeptide, glycoprotein, or glycolipid) that is uniquely or differentially expressed on a tumor cell compared to a normal or non-neoplastic cell. With reference to the invention, a tumor antigen includes any polypeptide expressed by a tumor that is capable of being recognized by an antigen recognizing receptor (e.g., CD19, Muc-1) or capable of suppressing an immune response via receptor-ligand binding (e.g., CD47, PD-L1/L2, 87.112).

By "tissue antigen" is meant an antigen (e.g., a polypeptide or glycoprotein or glycolipid) that is uniquely or differentially expressed on a normal or non-neoplastic cell or tissue compared to a tumor cell.

By "virus antigen" is meant a poly peptide expressed by a virus that is capable of inducing an immune response.

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

The term "subject" as used herein refers to a vertebrate, preferably a mammal, more preferably a human.

The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

Other aspects of the invention are described in the following disclosure and are within the ambit of the invention.

BRIEF DESCRIPTION OF THE FIGURES

The following Detailed Description, given by way of example, but not intended to limit the invention to specific embodiments described, may be understood in conjunction with the accompanying drawings.

FIGS. 2A to 2F show that iCARs protected iPS-fib from TCR-mediated allogeneic reactions. Control Pdel- or iCAR-transduced T cells primed with allogeneic moDCs were incubated with iPS-derived fibroblasts (iPS-fib) expressing click beetle luciferase (CBL), isogenic to the moDCs, using a range of E/T ratios. (A) Pdel-, PD-1-, or mutCTLA-4 iCAR-P-transduced T cells reacting against target iPS-fib (n=3 per condition). Killing of the iPS-fib was quantified with the Bright-Glo assay system. (B) Cytokine secretion in cell culture supernatants from (A) at 4:1 E/T ratio was assessed at 18 hours. GM-CSF, granulocyte-macrophage colony-stimulating factor; IFN-γ, interferon-g; TNF-α, tumor necrosis factor-a. (C) Pdel- or iCAR-positive T cells were incubated for 24 hours with off-target iPS-fib expressing PSMA (iPS-fib-PSMA), and luciferase signal (left) was quantified (right) (n=3 for each condition). (D to F) Cytokine secretion measured at 24 hours in cell culture supernatants from (C). Error bars represent ±SEM. *P<0.01, ***P<0.001 by analysis of variance (ANOVA) comparing iCARs to Pdel and post hoc analysis with multiple t tests corrected with the Holm-Sidak method. Raw data and P values are provided in the FIGS. 19A to 19E.

Figure 1A:
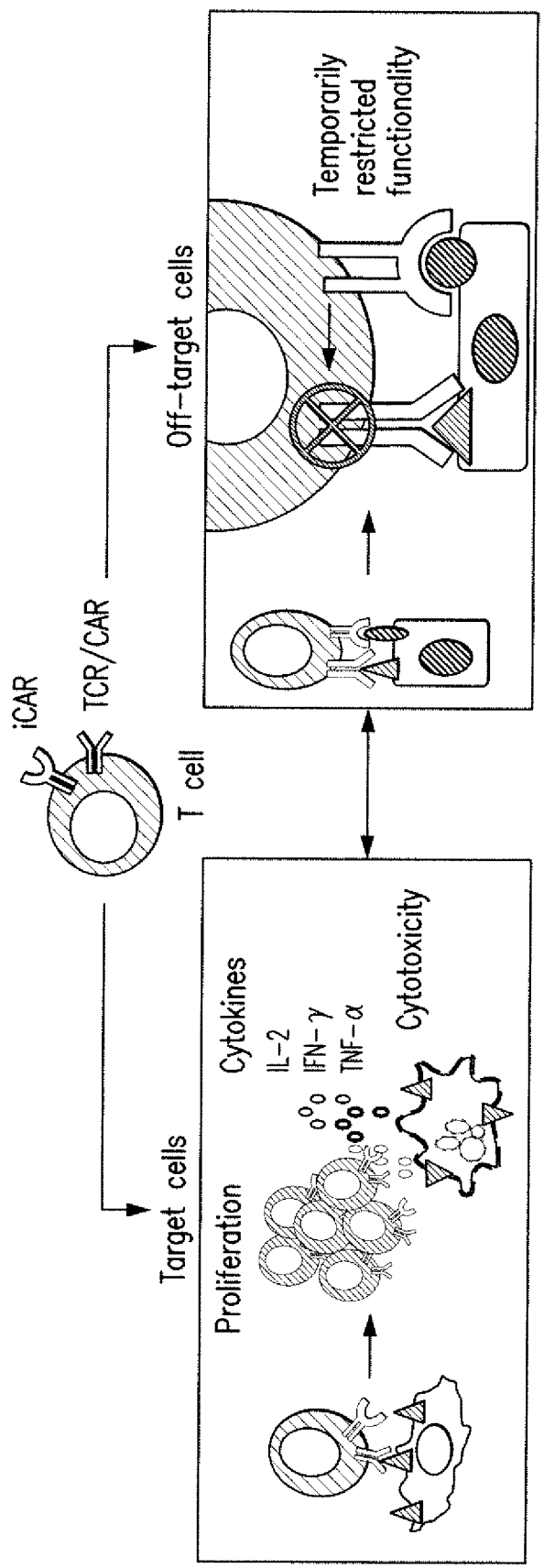
FIGS. 1A to 1D represent iCAR strategy, design, and expression in primary human T cells. (A) T cells with specificity for both tumor and off-target tissues can be restricted to tumor only by using an antigen-specific iCAR introduced into the T cells to protect the off-target tissue. (B) Schematic diagram of the bicistronic vectors used for iCARs and Pdel. iCAR-P: a spacer, transmembrane, and intracellular tail of each inhibitory receptor were cloned into a previously described retroviral vector having a CD8 leader sequence (LS). IRES, internal ribosomal entry site; hrGFP, humanized Renilla green fluorescent protein reporter. A Pdel control vector was designed with a spacer and CD8 transmembrane (TM) domain, and lacking an intracellular tail. (C) Cell surface expression of the iCARs was assessed by flow cytometry in transduced primary human T cells. Dot plots are representative of eight different donors. GAM, goat anti-mouse immunoglobulin G F(ab')2 antibody that binds to the murine-derived extracellular domain of the CAR. (D depicts flow cytometry analysis of cell surface expression of the iCARs using Goat-Anti-Mouse (GAM) staining in transduced primary human T cells.

***P<0.001 by Student's t test. Raw data and P values are provided in the FIGS. 22A to 22C.

FIGS. 6A to 6F show that iCARs restricted 19-28z CAR target cell specificity in vivo. (A) BLI depicting the tumor progress of NALM/6 or NALM/6-PSMA in NOD/SCID/$\gamma_c^-$ mice treated with sorted 19-28z/PD-1 iCAR-P T cells. Untreated mice (no T cells) were used as control. (B) Tumor burden for each mouse was quantified, and average total flux per group is shown. (C) Spleen weight of mice from (A) sacrificed at day 21. Each dot represents one recipient mouse. (D) Flow cytometric analysis of the femur bone marrow from (C) for the presence of tumor cells (CD19$^+$ GFP$^+$) and T cells (CD19-19-28z/GFP$^+$CD4$^+$CD8$^+$). 19-28z expression was assessed by staining for LNGFR receptor whose complementary DNA (cDNA) is linked to 19-28z and is used as a detection marker. (E and F) Absolute numbers of tumor cells (E) and of CD19$^-$19-28z/GFP$^+$CD4$^+$CD8$^+$ T cells (F) in the spleens from (C) were quantified by flow cytometry with CountBright beads (n=4). Error bars represent ±SEM. P<0.01, *P<0.001 by Student's t test.

FIGS. 7A to 7D show that iCAR function was temporary and reversible. (A) 19-28z/Pdel or 19-28z/PD-1 iCAR-P T cells were incubated with target (T) or off-target (O) AAPCs for the first stimulation. After 3 or 7 days, the cells from each group were restimulated with either target [T→T (1) or O→T (2)] or off-target [T→O (3) or O→O (4)] AAPCs in a crisscross manner to analyze the effects of the first stimulation on subsequent T cell function. (B) Killing of target (T) or off-target (O) AAPCs at 24 hours after incubation with each T cell group (second stimulation) was analyzed with the Bright-Glo assay system (n=3 for each condition). (C) Secretion of effector cytokines in the cell culture supernatant from (B) was analyzed 24 hours after the second stimulation, and interferon-g (IFN-g) is shown as a representative result (n=3 for each condition). (D) T cell proliferation at day 7 after the second stimulation (n=3 for each condition). Error bars represent ±SEM. Statistical comparison was performed within each condition (that is, T→T Pdel versus PD-1 iCAR-P). ***P<0.001 by Student's t test.

FIGS. 8A to 8E show that iCAR- and CAR-expressing T cells discerned targets in vitro and vivo. (A) 19-28z/Pdel or 19-28z/PD-1 iCAR-P T cells were incubated with a 1:1 mix of target (CD19$^+$GFP$^+$, green) and off-target (CD19$^+$PSMA$^+$ mCherry$^+$, red) AAPCs, and time-lapse microscopy was used to visualize real-time killing of each population for 38 hours. Representative images are shown, and full-length movies were made. Scale bars, 0.1 mm. (B) As in (A), 19-28z/Pdel or 19-28z/PD-1 iCAR-P T cells were incubated with a 1:1 mix of target (CD19+) and off-target (CD19+ PSMA+) AAPCs. Killing of each AAPC population was assessed in parallel experiments where one of each AAPC type was labeled with CBL (CD19+CBL+/CD19+PSMA+ mix or CD19+/CD19+PSMA+CBL+ mix). Killing was quantified with the Bright-Glo assay system at 38 hours (n=3 for each condition). (C to E) NOD/SCID/$\gamma_c^-$ mice were injected with a 1:1 mixture of NALM/6 and NALM/6-PSMA cells and treated with 19-28z or 19-28z/PD-1 iCAR-P T cells. (C) Upon sacrifice, the presence of the target and off-target NALM/6 cells in the bone marrow was analyzed by flow cytometry. (D) Ratio of target/off-target NALM/6 cells in the bone marrow of sacrificed mice was quantified by flow cytometry. (E) Spleen weight of treated mice was also recorded at sacrifice. Error bars represent ±SEM. ***P<0.001 by Student's t test.

Figure 9A:
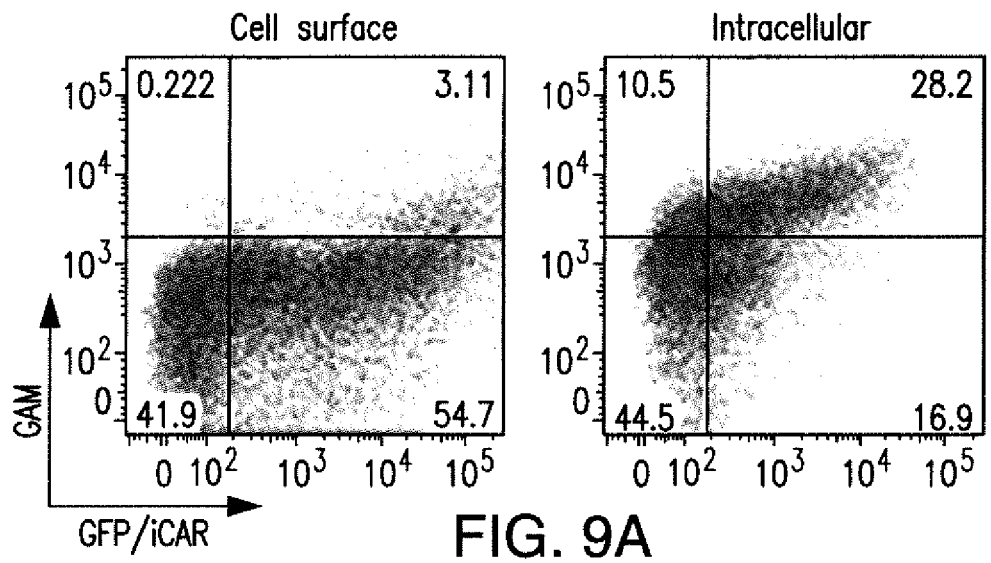
Figure 9B:
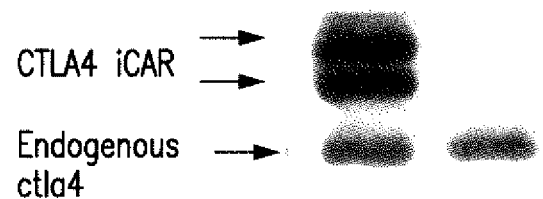
Figure 9C:
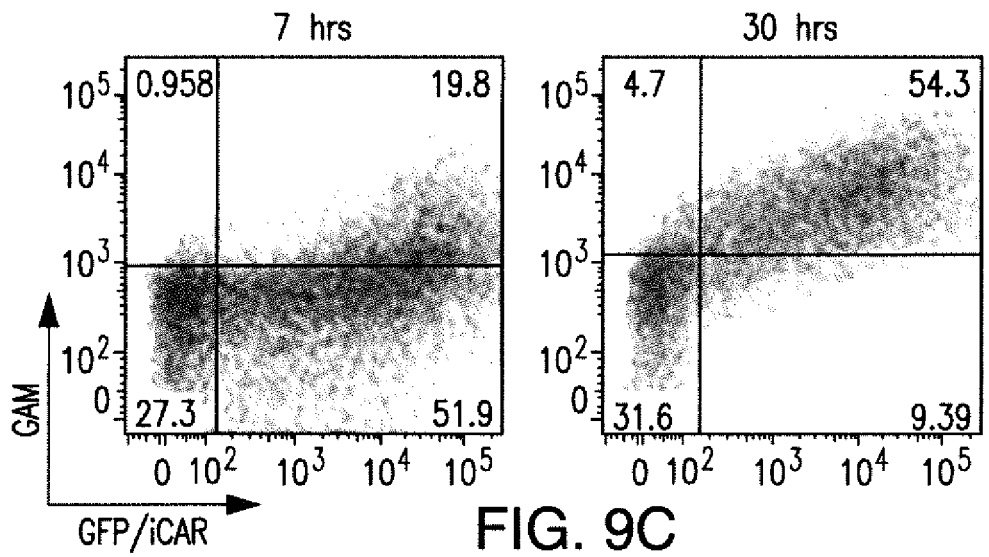

FIGS. 9A-C show that CTLA-4 iCAR cell surface expression was increased after T cell activation. (A) Cell surface and intracellular expression of CTLA4 iCAR-P on transduced primary human T cells (B) Western blot analysis using an antibody specific for the intracellular domain of CTLA4 on untransduced (2) and CTLA4 iCAR-P transduced (1) primary human T cells. Murine EL4 cells (3) served as negative control. (C) 1928z/CTLA4 iCAR T cells were activated using 3T3-19 AAPCs and analyzed for cell surface CTLA4 iCAR expression at 7 hrs and 30 hrs post activation (n=3).

Figure 10:
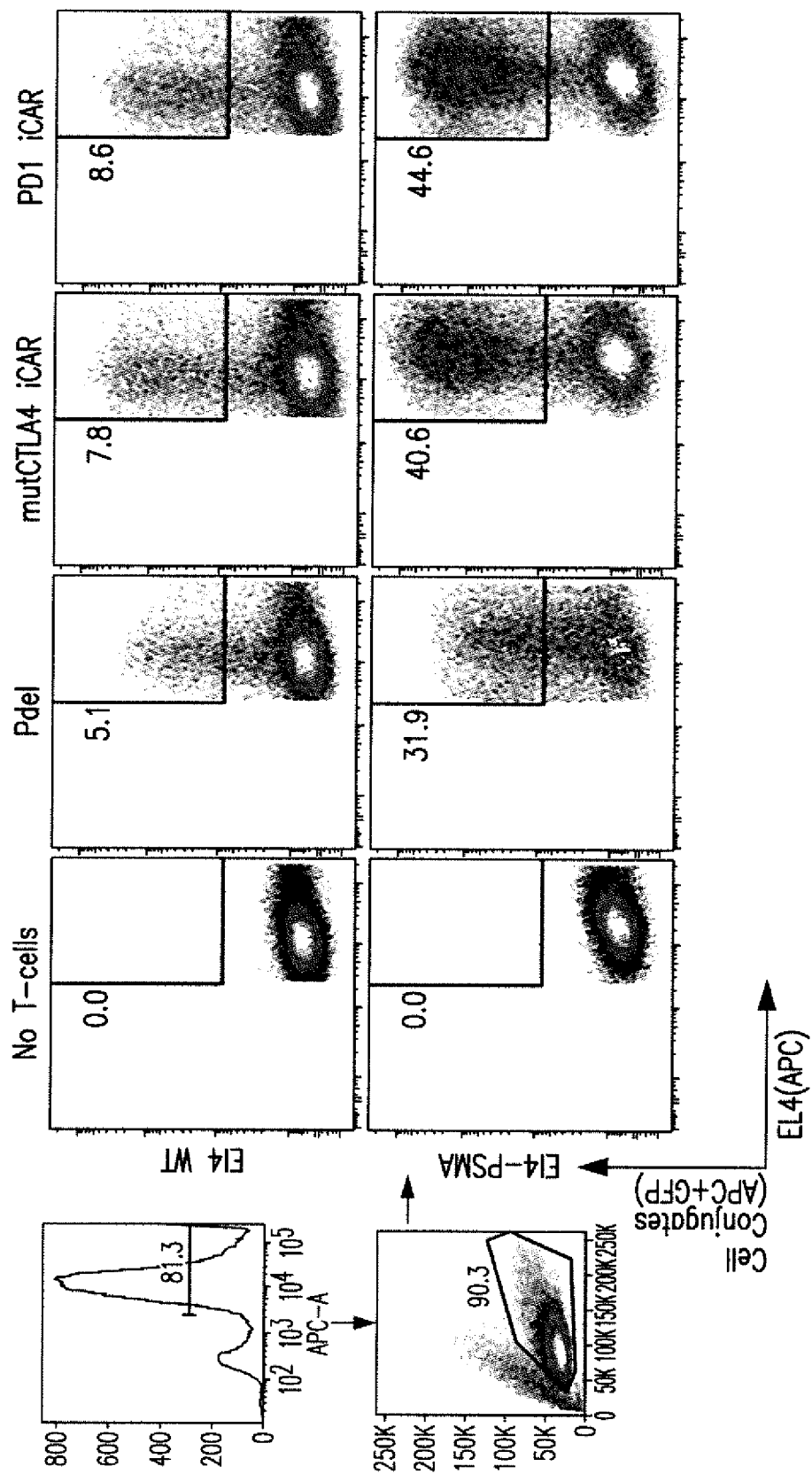

FIG. 10 shows that iCAR-P bound to PSMA expressing cells. EL4-wt or EL4-PSMA cells, labeled with the lipophilic DiD dye, were incubated with iCAR/GFP expressing T cells in a cellular conjugation assay. Conjugates are detected by flow cytometry as DiD/GFP double positive events.

FIGS. 11A to 11D represent allogeneic reactivity model using iPS-derived fibroblasts and isogenic moDCs. (A) Induced pluripotent stem (iPS) cells were generated from Donor 1 PBMCs and used to derive fibroblasts. Donor 1 PBMCs were also used to derive moDCs, which were pulsed with fibroblast lysates and could prime an allogeneic reaction from a second donor's PBMCs. (B) Microscopy picture showing the morphology of teratoma-derived iPS-fibroblasts grown in culture. (C) iPS-fib, lacked expression of pluripotency markers, displayed fibroblast morphology, and stained positive for several fibroblast cell surface markers including CD90, PDGFr-b2, and CD10. (RED=isotype control; BLUE and GREEN are two independent isolated lines) (D) iPS-fib basally stained positive for HLA class I, but not class II, and rapidly upregulated expression of both upon recombinant INF gamma treatment.

Figure 12A:
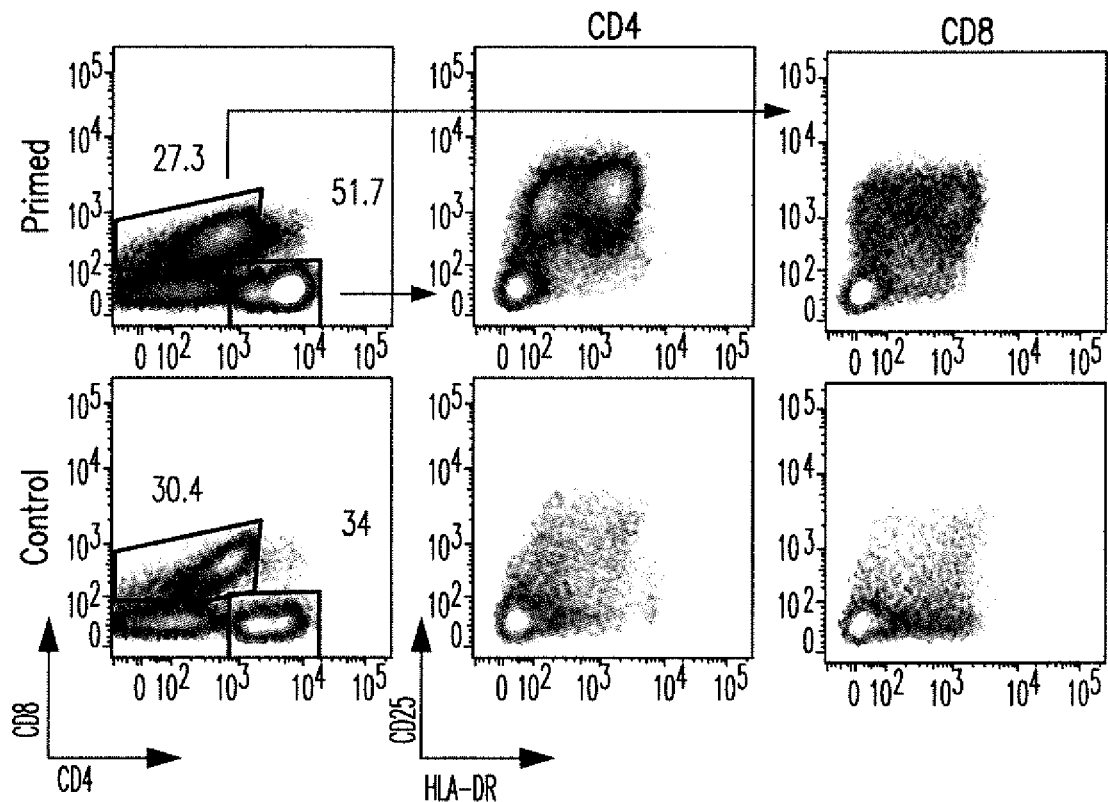
Figure 12B:
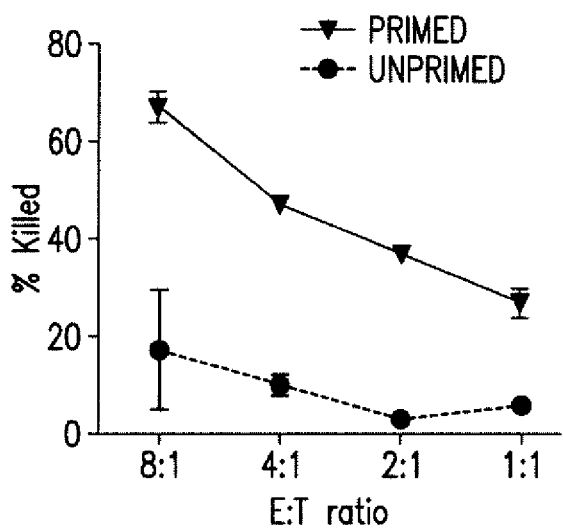
Figure 12C:
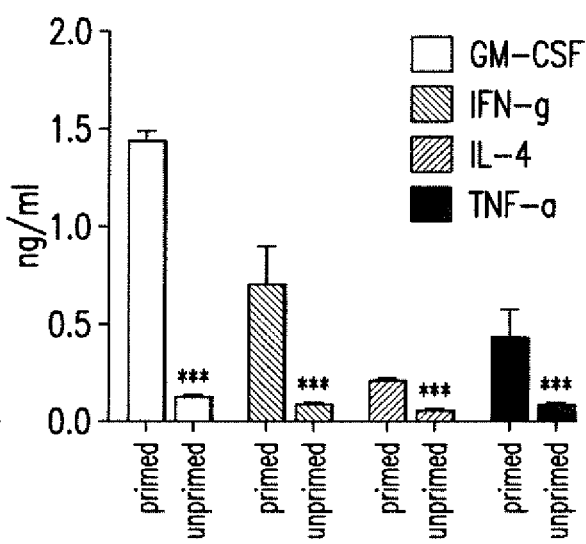

FIGS. 12A to 12C represent potent reactivity of iCAR-transduced primary human T cells against allogeneic iPS-derived fibroblasts. (A) iCAR transduced T cells from one donor were primed with moDCs pulsed with iPS-fib lysates of a different donor, and 6 days later stained for the activation markers CD25 and HLA-DR. (B) Twice primed iCAR transduced T cells were incubated for 18 hrs with iPS-fib-luc and killing was quantified using the Bright-Glo assay system (n=3 for each condition). (C) Cytokines were measured at 18 hrs in the cell culture supernatant from (B) at 4:1 E:T ratio. Error bars represent +/- SEM. Statistical comparison was carried out within each condition (ie $T_1T$). ***p<0.001 by Student's t test.

Figure 13A:
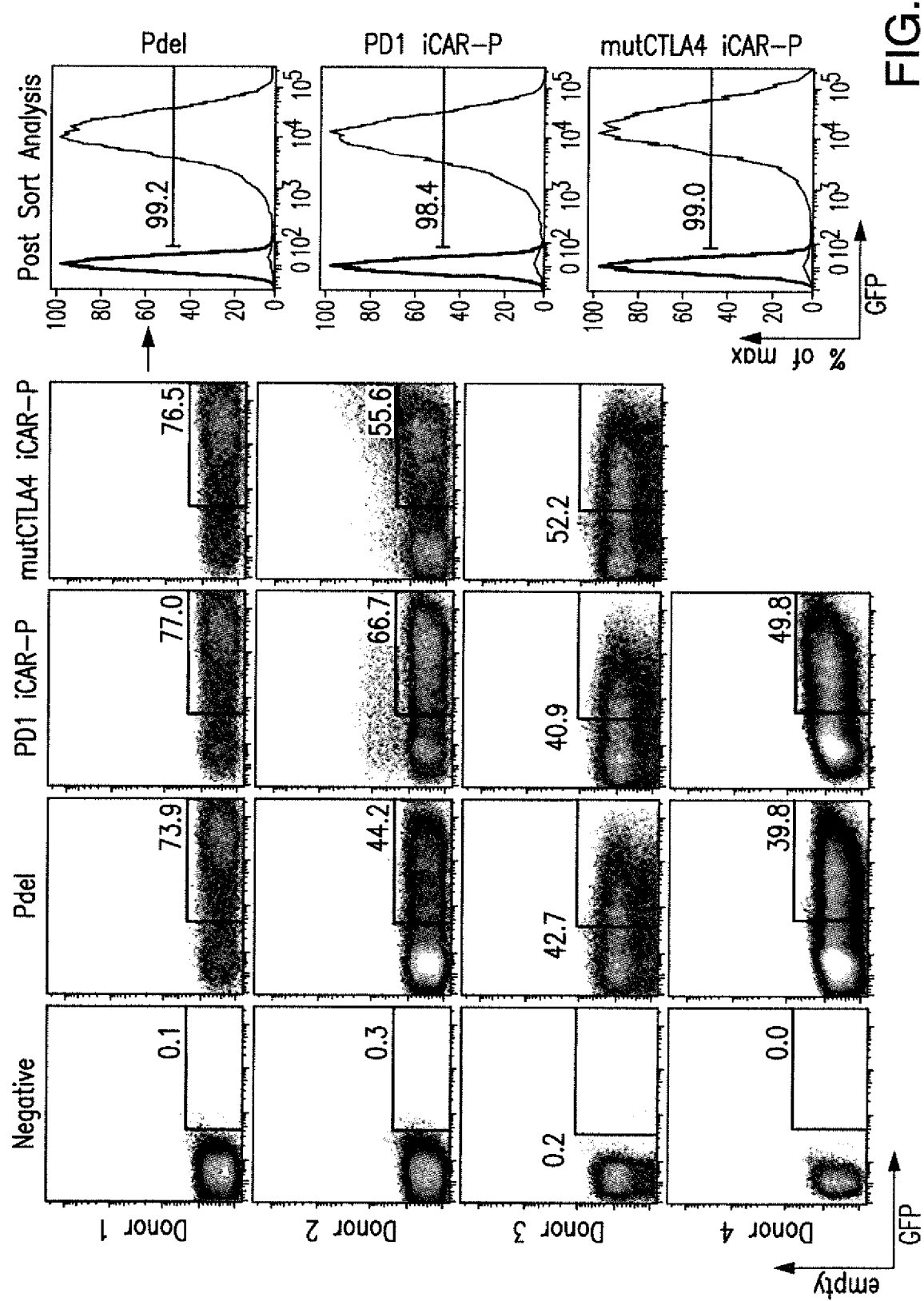
Figure 13B:
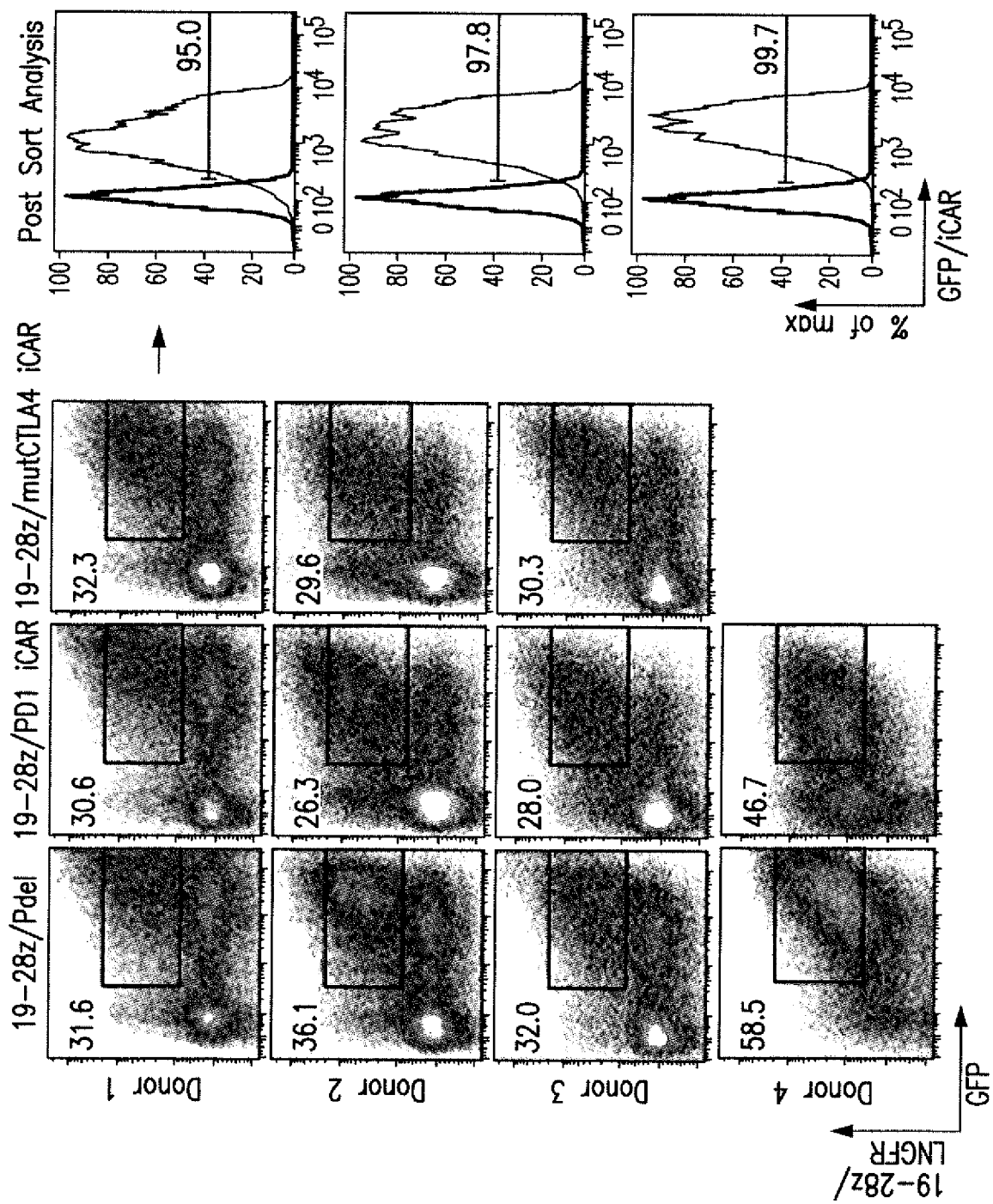

FIGS. 13A and 13B represent transduction and sorting strategy of iCAR or 19-28z/iCAR T cells. (A) PD1-iCAR (GFP) or Pdel (GFP) transduced T cells were sorted for transgene expression based on GFP expression level. Each donor represents a separate experiment. Post sort analysis was carried out to confirm purity. (B) 19-28z (LNGFR)/ iCAR(GFP) or 19-28z/Pdel/GFP transduced T cells were sorted for transgene expression based on GFP expression and LNGFR level. Each donor represents a separate experiment. Post sort analysis was carried out to confirm purity and iCAR expression.

Figure 14A:
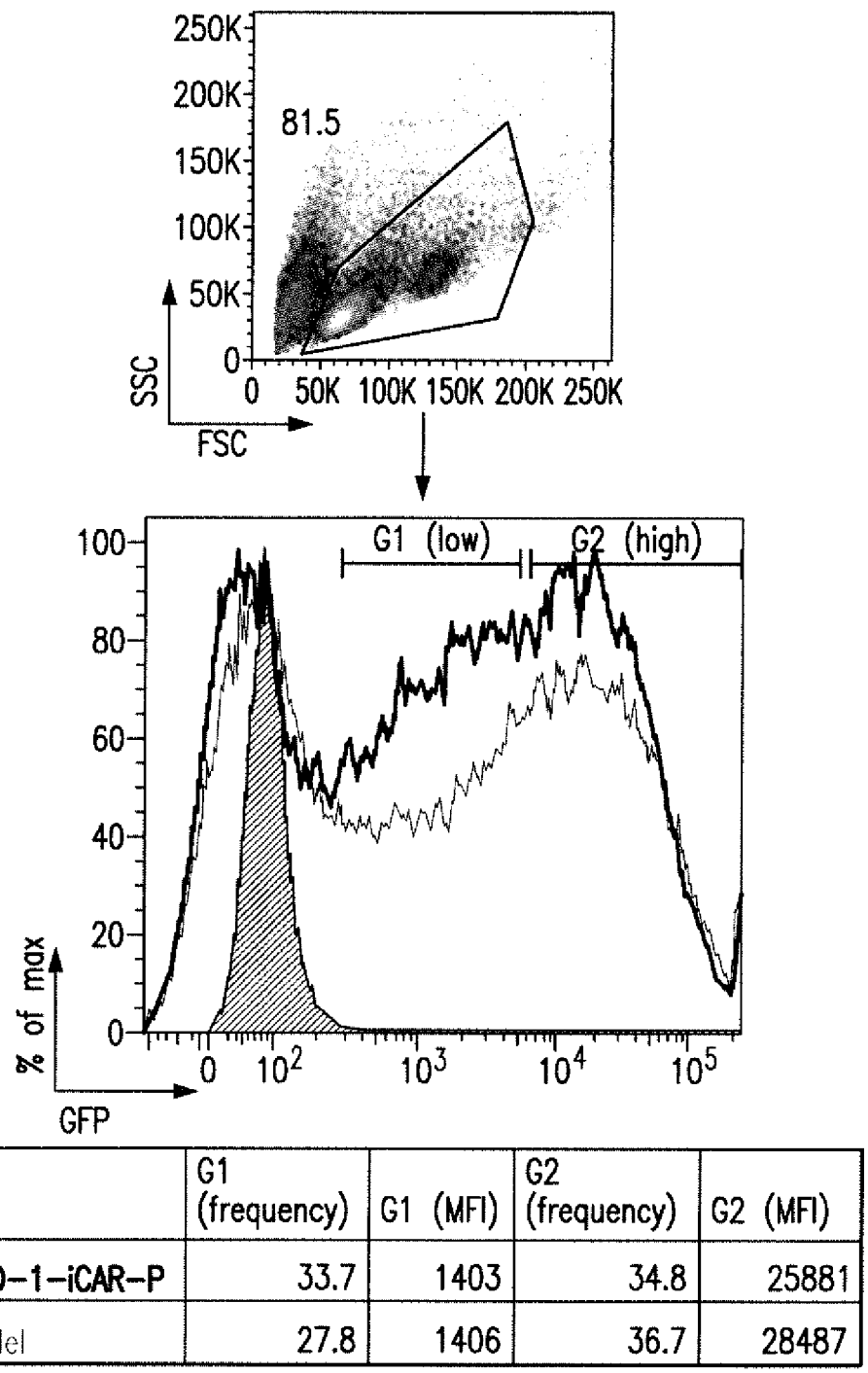
Figure 14B:
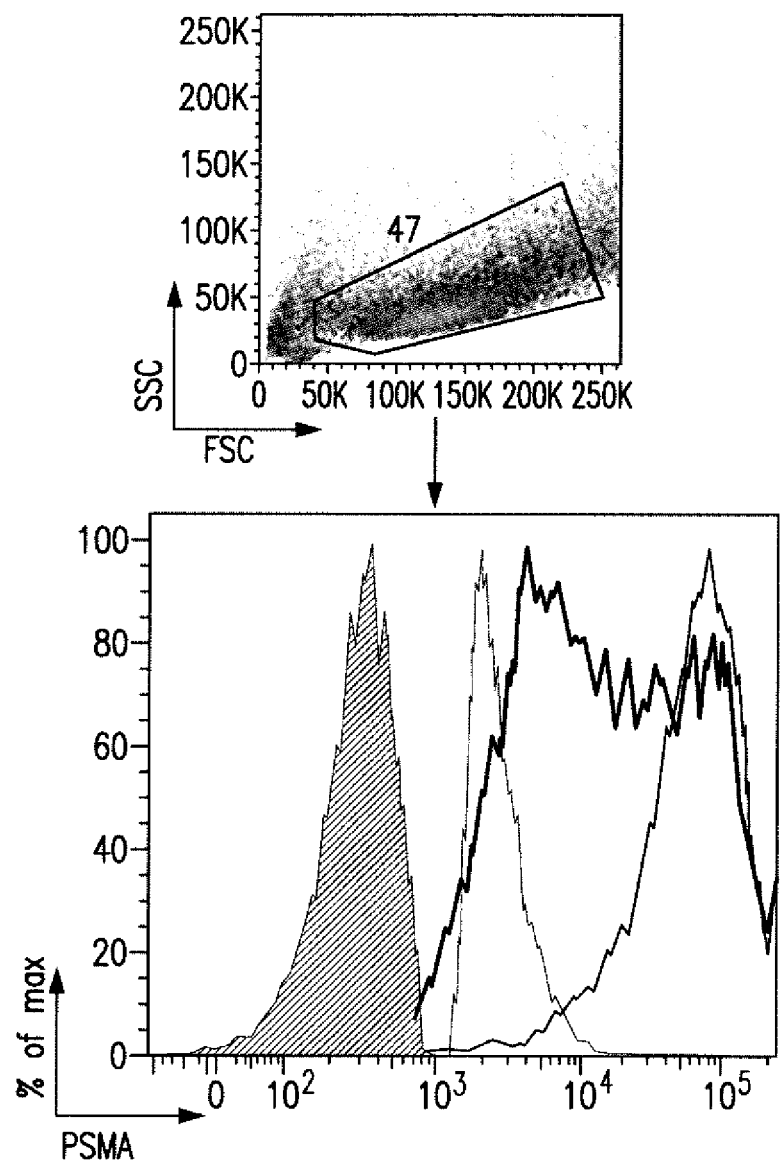

FIGS. 14A and 14B represent sorting strategy of low/high iCAR—expressing T cells and PSMA-expressing iPS fibroblasts. (A) PD1-iCAR/GFP or Pdel/GFP transduced T cells were sorted for low or high transgene expression based on GFP expression level. (B) iPS-derived fibroblasts (iPS-fib) were transduced to express PSMA and sorted using an anti-PSMA antibody (iPS-fib-PSMA sort bulk+). These cells were used for experiments in FIGS. 2 and 4. A second separate sort was used to purify low or high surface PSMA expressing iPS-fib using an anti-PSMA antibody and these cells were used in experiments in FIG. 3.

FIGS. 15A to 15D show that iCARs inhibited 19-28z-driven human T cell cytokine release and proliferation. (A)

human T cell proliferation in artificial antigenpresenting cells (AAPCs) expressing CD19 or both CD19 and PSMA. (B) Representative INFγ cytokine analysis of supernatants at 24 h and 48 h post seeding of dual sorted 19-28z/Pdel or iCAR transduced human T cells on CD19 (target) or CD19/PSMA (off-target) positive AAPCs. Data represented as a ratio of offtarget/target values and are pooled from three independent experiments. (n=6 wells per condition). Error bars represent +/− SEM. (C) Absolute counts of double positive 19-28z/Pdel or iCAR T cells stimulated on day 0 and 7 with CD19+ (target) AAPCs. (D) Comparison of therapeutic T cell responses with NALM/6 and NALM/6-PSMA cells in a xenograft NOD/SCID/$\gamma_c^-$ mouse model.

Figure 16C:
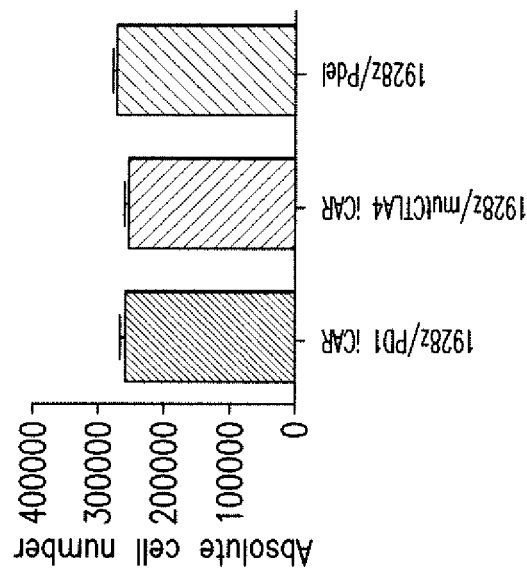
Figure 16B:
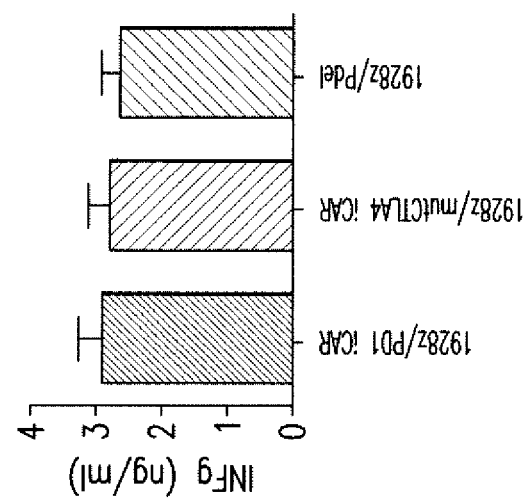
Figure 16A:
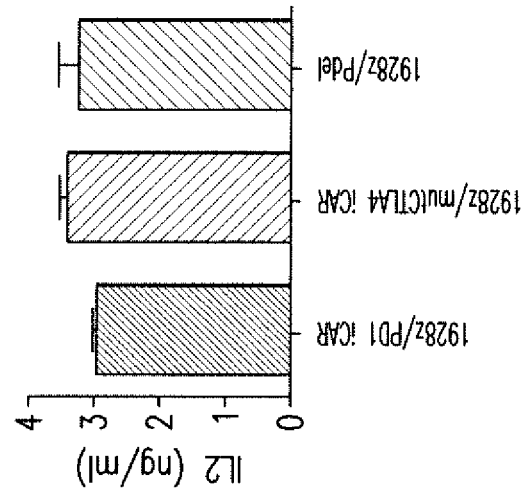
Figure 16D:
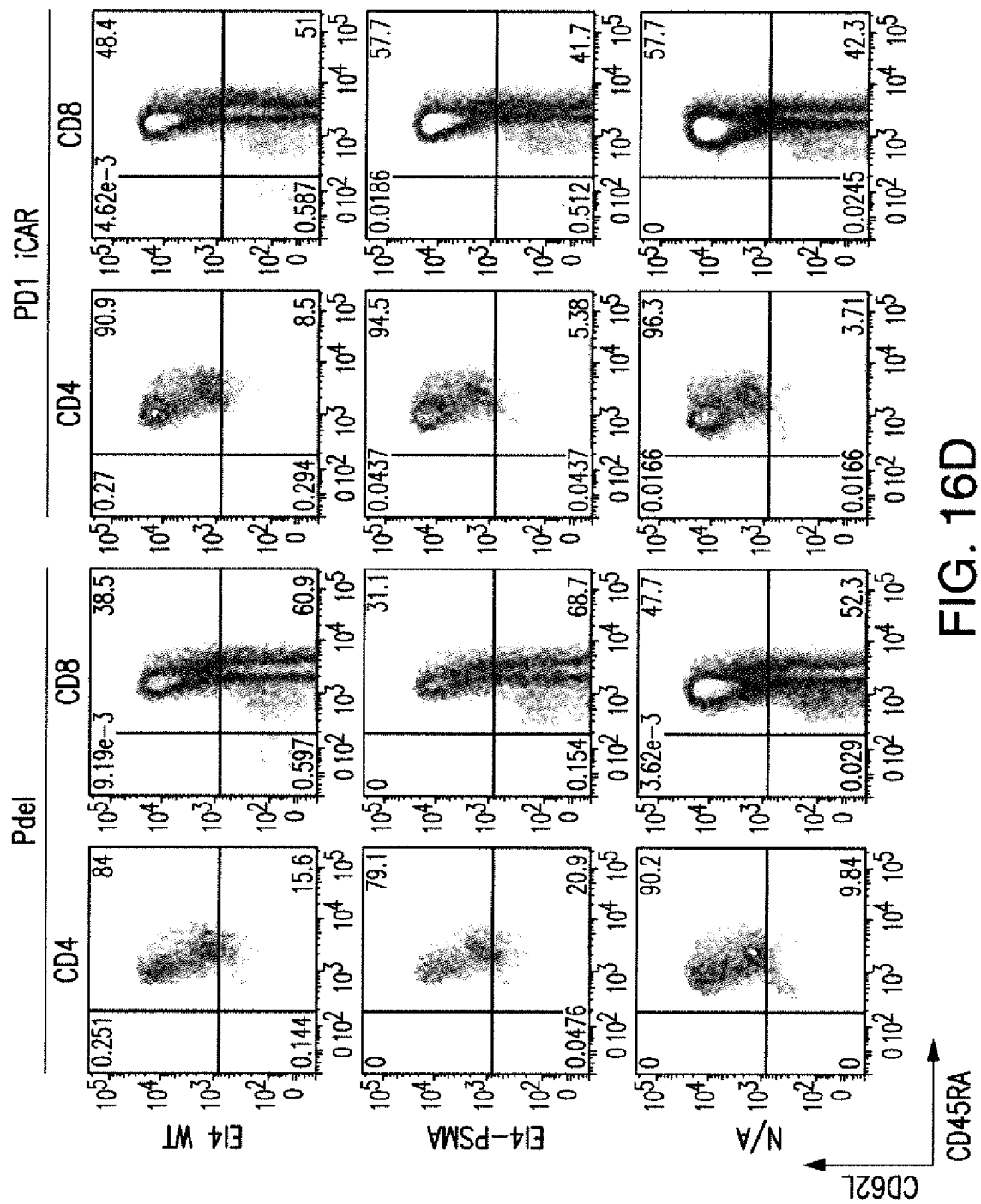
Figure 16E:
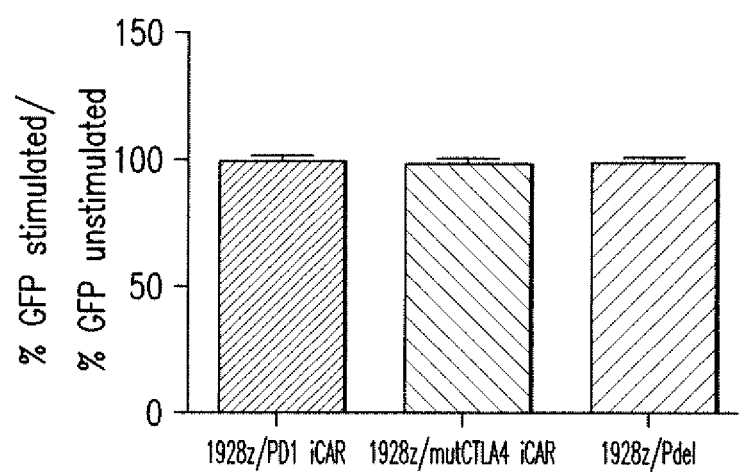

FIGS. 16As to 16I show that basal expression of iCARs did not affect function of primary human T cells. (A,B) Seven days post transduction with 1928z/iCAR, T cells were activated with CD3/CD28 beads and IL-2/INFγ levels were assessed after 24 hrs (C). At eight days after bead activation, absolute T cell expansion was quantified using CountBright beads (D) and the change in the percent of GFP positive cells in each iCAR group was normalized relative to unstimulated cells. (E) 1928z/iCAR T cells were co-cultured for five days with irradiated EL4-WT or EL4-PSMA cells and immunophenotyped using flow cytometry. (F) depicts cellular conjugation assay of EL4-wt or EL4-PSMA cells, labeled with the lipophilic DiD dye and incubated with iCAR expressing T-cells. (G) represent graphs depicting IL-2/INFγ levels in T-cells 24 hrs after activation with CD3/CD28 beads, seven days post transduction with 1928z/iCAR. (H) is a graph depicting quantification of absolute T-cell expansion using CountBright beads at eight days post bead activation. (I) is a graph depicting the change in the percent of GFP positive cells in each iCAR group was calculated relative to unstimulated cells.

Figure 17A:
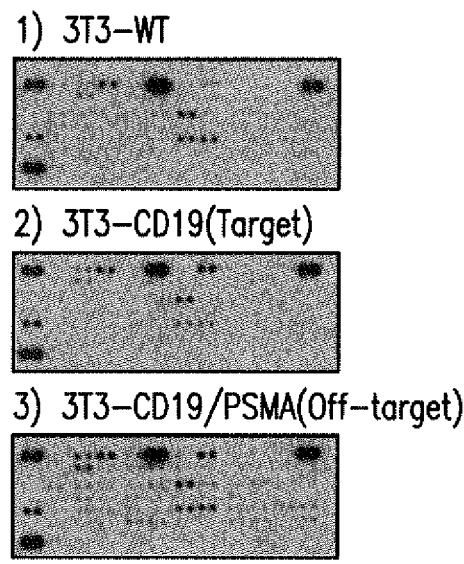
Figure 17B:
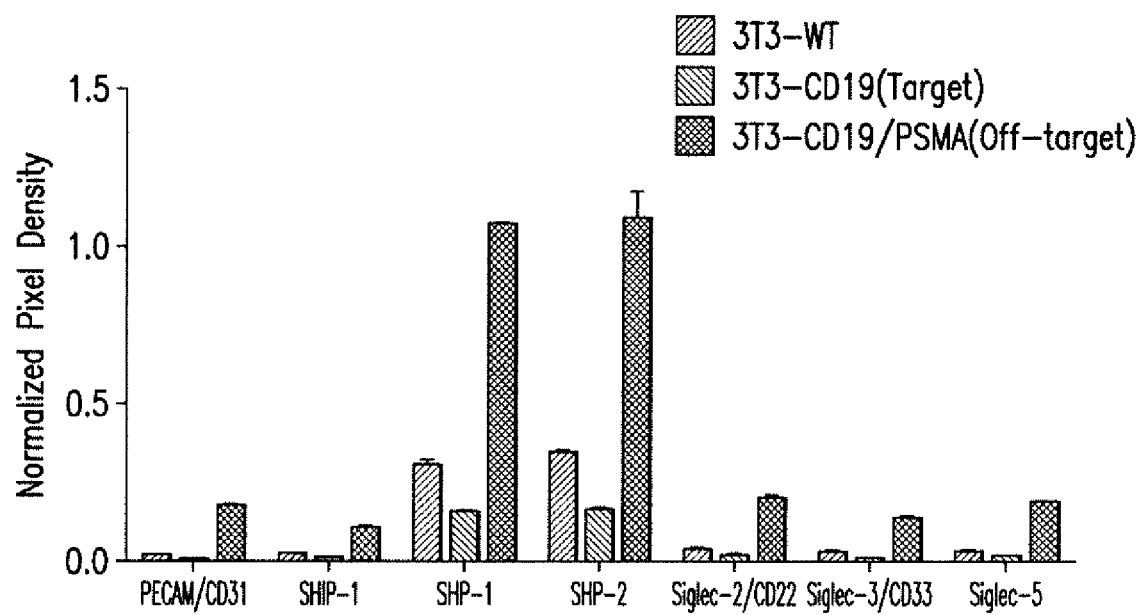
Figure 17C:
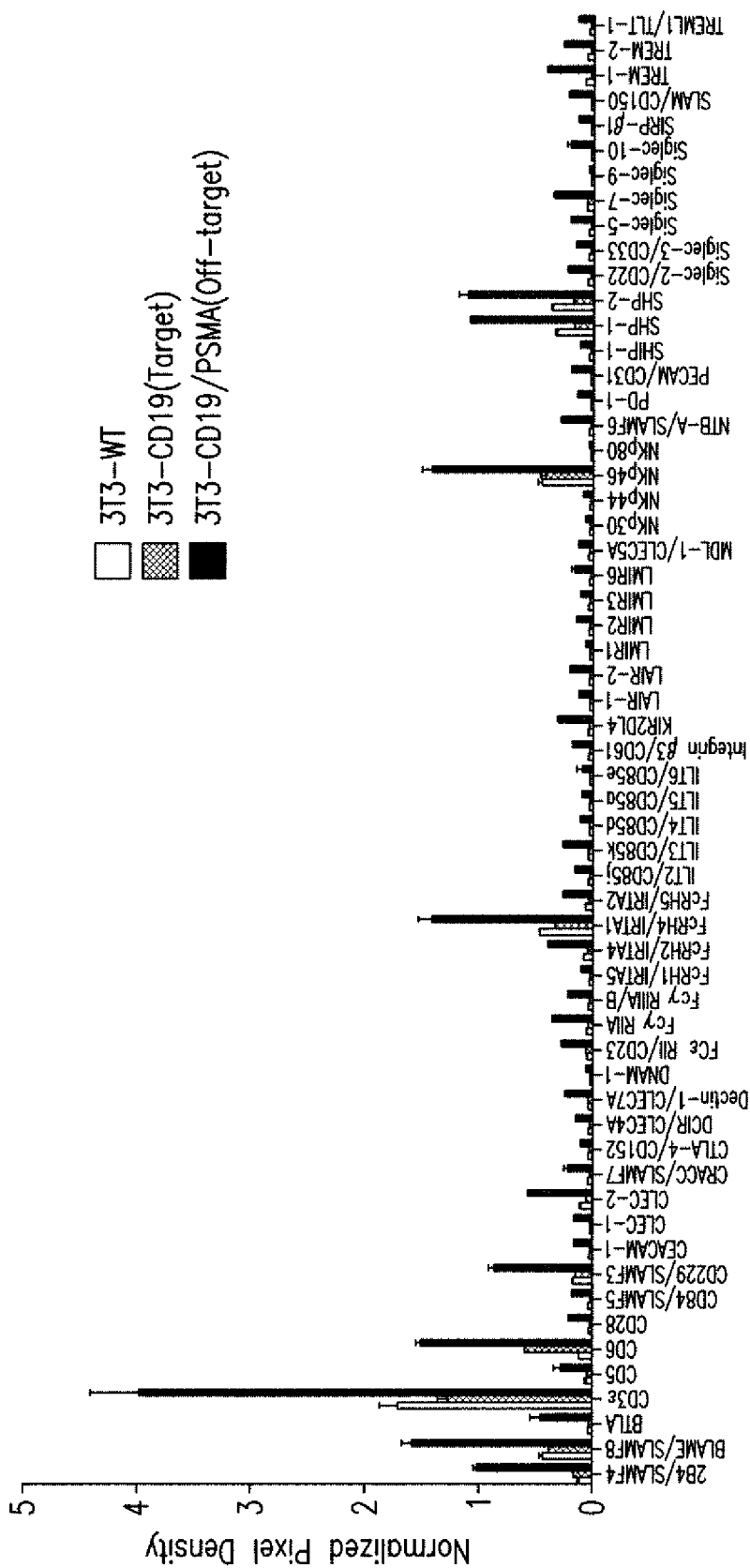

FIGS. 17A to 17C represent signaling and biochemical pathway characterization of the PD-1 iCAR. 19-28z/PD-1 iCAR cells were exposed to AAPCs expressing no antigen (WT), CD19 (Target), or CD19 and PSMA (Off-Target) at an E:T ratio of 4:1 for 60 min. (A) Human Phospho-Immunoreceptor Array incubated with 100 μg of lysate from 19-28z/PD-1 iCAR T cells and respective AAPCs. All blots were detected using chemiluminescence on the same X-ray film to standardize exposure levels. (B,C) Quantification of arrays in (A) using scanned X-ray film images analyzed using image analysis software. All pixel density is normalized on each array using internal pY controls. (B) SHP1 and SHP2 phosphorylation states on target, off-target, or control AAPCs. (C) Quantification of phosphorylation levels of 59 ITAM/ITIM-associated immunoreceptors.

Figure 18:
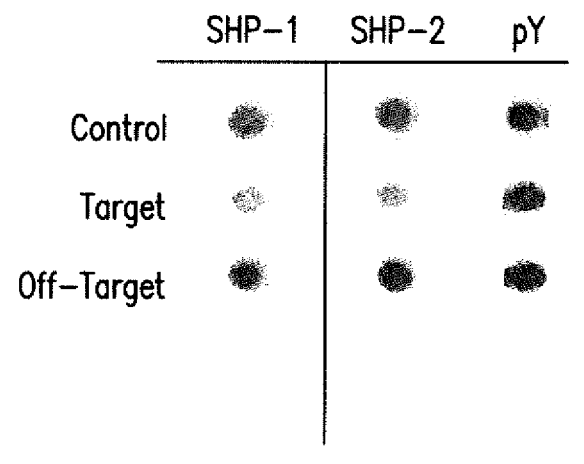

FIG. 18 shows that iCAR directly acted on the stimulatory receptor to block its signaling.

FIGS. 19A to 19E represent raw data and statistical significance testing for FIGS. 2A to 2F. (A) Killing of the iPS-fibroblasts was quantified using the Bright-Glo assay system for Pdel, PD-1, or mutCTLA-4 iCAR-P transduced T cells. (B) Cytokine secretion in cell culture supernatants from (A) at 4:1 E:T ratio was assessed at 18 hrs. (C) Pdel or iCAR positive T cells were incubated for 24 hrs with off-target iPS-fib expressing PSMA (iPS-fib-PSMA) and luciferase signal was quantified. (D) Posthoc analysis for (C) was carried out using multiple t-tests corrected with the Holm-Sidak method. (E) Cytokine secretion measured at 24 hrs in cell culture supernatants from (C). Raw values for GM-CSF are presented. E:T ratio, effector:target ratio.

FIGS. 20A and 20B represent raw data and statistical significance testing for FIGS. 3A to 3D. (A) Killing of iPSfib-PSMA relative to untreated cells was assessed by using the Bright-Glo assay system for sorted high and low Pdel or PD1 iCAR-P transduced alloreactive T cells. Posthoc analysis was carried out using multiple t-tests corrected with the Holm-Sidak method. (B) PD1 iCAR-P transduced alloreactive T-cells killing of iPS-fib-PSMA sorted for high or low levels of PSMA expression was quantified using the Bright-Glo assay system. Posthoc analysis was carried out using multiple t-tests corrected with the Holm-Sidak method.

Figure 4A:
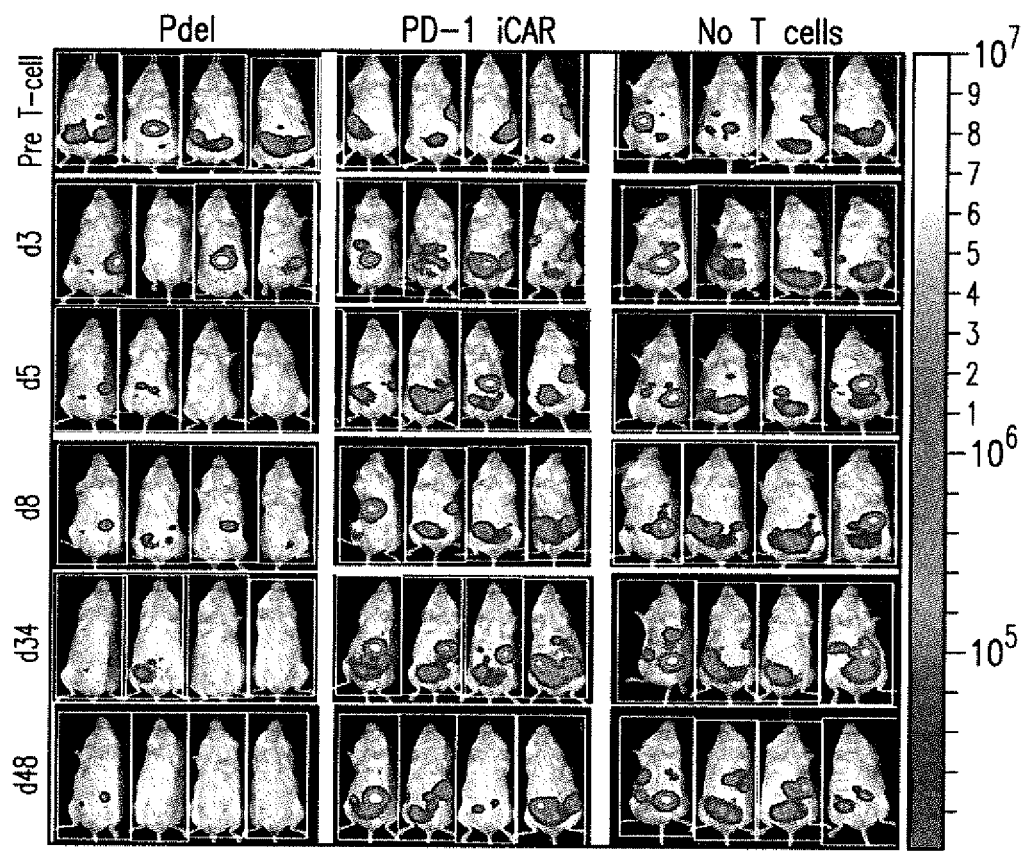
FIGS. 4A and 4B show that iCARs limited allogeneic responses in vivo. NOD/SCID/$\gamma_c^-$ mice were injected intraperitoneally with $1 \times 10^6$ iPS-derived fibroblasts expressing CBL/PSMA (iPS-fib-PSMA) and, 7 days later, were treated intraperitoneally with $5 \times 10^5$ PD-1 iCAR-P- or Pdel-transduced, sorted, alloreactive T cells. Untreated mice (no T cells) were used as control. (A) Survival of iPS-fib-PSMA was assessed by BLI before and at selected time points after T cell infusion. Images of four representative mice from each group are shown. (B) Total body flux (photons per second) for each mouse was quantified and averaged per group (n=5 per group). Error bars represent ±SEM. *P<0.05, **P<0.01 by ANOVA comparing to Pdel and post hoc analysis with multiple t tests corrected with the Holm-Sidak method. Raw data and P values are provided in the FIGS. 21A and 21B.
Figure 4B:
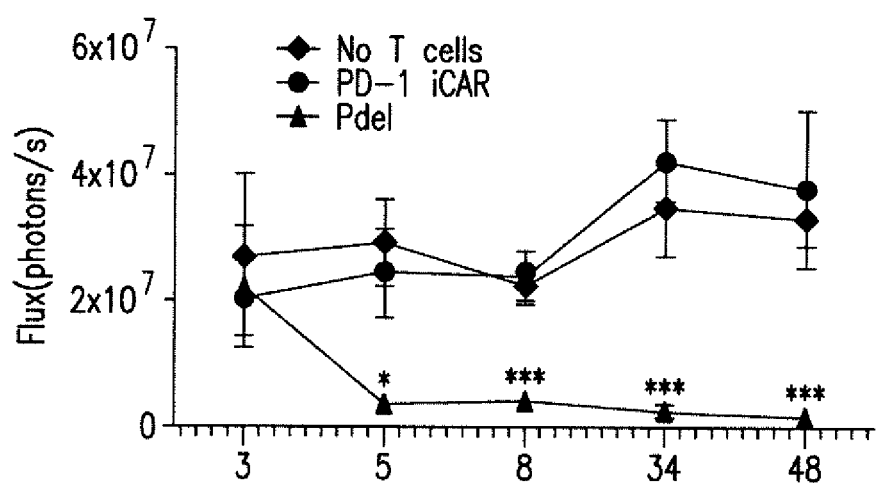

FIGS. 21A and 21B represent raw data and statistical significance testing for FIGS. 4A and 4B. (A) Bioluminescent imaging (BLI) of iPS-fib-PSMA before and at selected time points after T cell infusion. (B) Posthoc analysis was carried out using multiple t-tests corrected with the Holm-Sidak method.

Figure 5A:
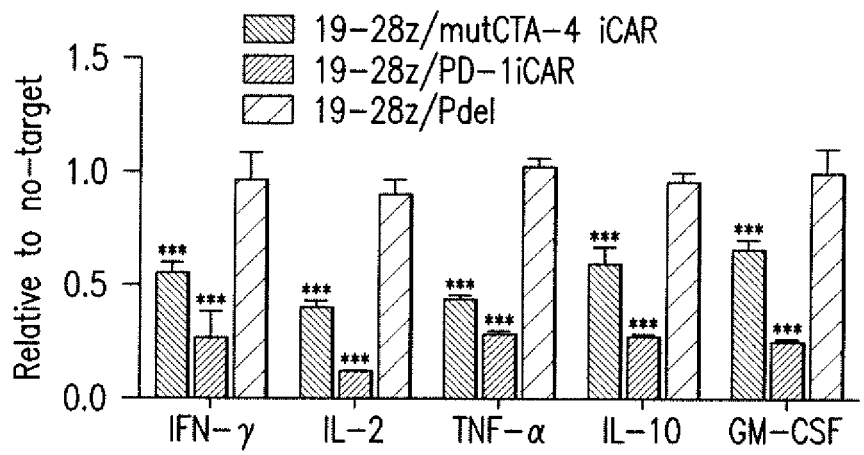
FIGS. 5A to 5F show that iCARs inhibited human T cell cytokine release, proliferation, and target cell elimination driven by 19-28z CAR. (A) Luminex multiplex cytokine analysis of culture supernatant 24 hours after seeding dual-sorted 19-28z/Pdel- or 19-28z/iCAR-transduced human T cells on 3T3-CD19 (target) or 3T3-CD19-PSMA (off-target) AAPCs. The data are represented as a ratio of off-target/target values and pooled from three independent experiments (n=6 wells per condition). Error bars represent ±SEM. P<0.01, *P<0.001 by ANOVA comparing iCARs to Pdel and post hoc analysis with multiple t tests corrected with the Holm-Sidak method. (B) Absolute counts of 19-28z/Pdel or 19-28z/iCAR T cells stimulated on days 0 and 7 with off-target AAPCs. No exogenous cytokines were added. Data are representative of six independent experiments. (C) Proliferation of 19-28z/Pdel or 19-28z/iCAR T cells stimulated on days 0 and 7 with offtarget AAPCs relative to proliferation on target AAPCs. No exogenous cytokines were added. Data are representative of six independent experiments. (D) T cells seeded at a 1:1 ratio on target and off-target mCherry+ AAPCs. Images at 38 hours and 5 days from one of five independent experiments are shown. Scale bars, 0.5 mm. (E and F) Quantification of mCherry signal from (D) against CD19 targets (E) or CD19-PSMA off-target cells (F), as described in Materials and Methods. Error bars represent ±SEM. **P<0.01.
Figure 5B:
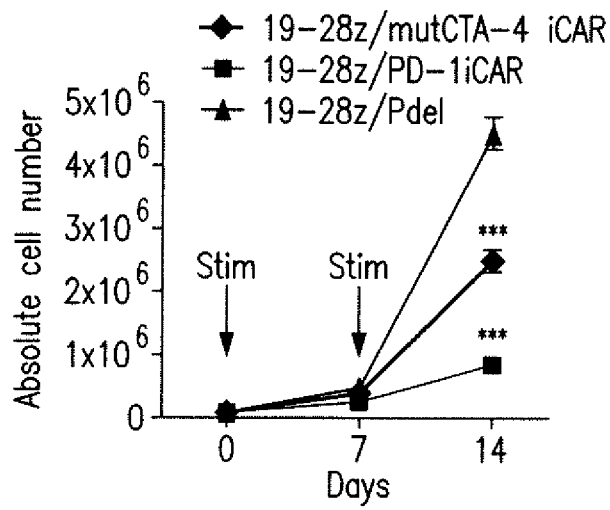

FIGS. 22A to 22C represent raw data and statistical significance testing for FIGS. 5A to 5F. (A) Luminex multiplex cytokine analysis of culture supernatant at 24 h, data are represented as a ratio of off-target/target values and pooled from three independent experiments (n=6 wells per condition). Posthoc analysis was carried out using multiple t-tests corrected with the Holm-Sidak method. (B) Posthoc analysis was carried out using multiple t-tests corrected with the Holm-Sidak method for FIG. 5B comparing the proliferation of 19-28z/Pdel and 19-28z/PD1 iCAR. (C) Quantification of mCherry signal against CD19 targets or CD19-PSMA off-target cells, as described in Methods. Posthoc analysis was carried out using multiple t-tests corrected with the Holm-Sidak method.

Figure 23:
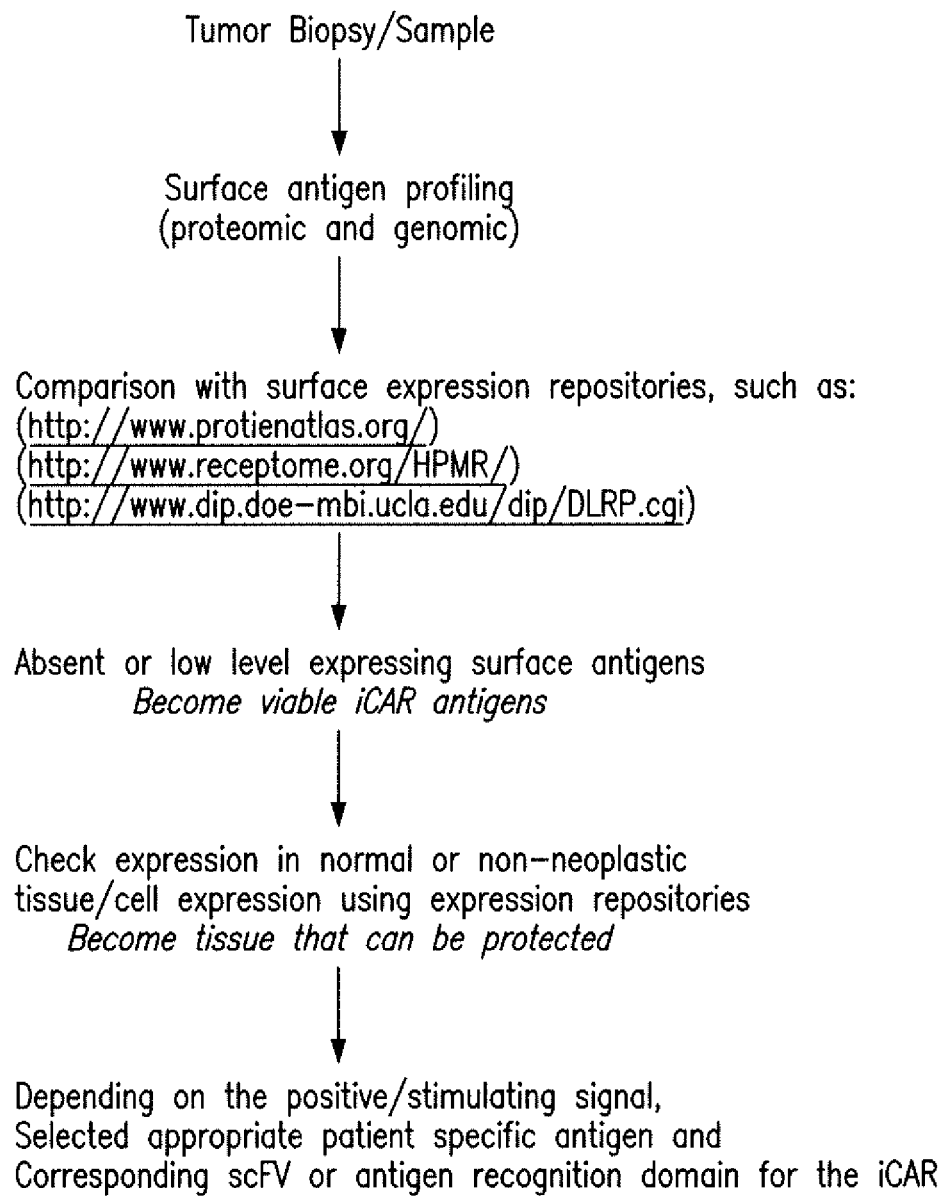

FIG. 23 is a schematic representation of a selection of target antigen for iCAR and CAR.

DETAILED DESCRIPTION OF THE INVENTION

The present invention generally provides cells, including genetically modified immunoresponsive cells (e.g., T cells (including all subsets such as CD4, CD8, memory, naïve, effector, T-reg etc.), cells of the innate immune system, Natural Killer (NK) cells, cytotoxic T lymphocytes (CTL) cells) expressing at least a combination of an antigen-recognizing receptor (e.g., TCR or CAR) and an inhibitory chimeric antigen receptor (iCAR) that selectively reduces or eliminates the immune activity of the immunoresponsive cell, and methods of using such cells for the treatment of neoplasia and other pathologies where reducing "off-target" immune responses is desired. The invention is based, at least in part, on the discovery that inhibitory chimeric antigen receptors (iCARs) that bind a target antigen (e.g., PSMA as shown herein) are useful for selectively inhibiting and suppressing an immunoreactive cell. In particular, the iCARs of the invention decrease or prevent activation of the immune response of an immunoreactive cell. The present approach provides selective immunogenicity for tumor eradication, while sparing non-tumor tissues from the immune response. Accordingly, T cells expressing an antigen recognizing receptor and an iCAR represents a significant advance over conventional adoptive T cell therapy.

The broad use of donor leukocyte infusion to treat cancer is hampered by the inability to separate the therapeutic efficacy of Graft-versus-tumor effect (GVT) from the potentially lethal effects of Graft-versus-host disease (GVHD). Two general approaches have been used to control T-cell therapy side effects. The first is the use of immunosuppressive drugs, which work non-specifically by blocking cell division (cytostatics) and broadly limit immune responses (glucocorticoids, immunophilins, etc), or targeting T-cells for clearance/death (antibodies). Although powerful, these approaches are nonspecific in terms of separating therapeutically functioning T-cells and ones causing deleterious side effects. Additionally, all these drugs cause significant long-term secondary side effects (susceptibility to infections, cardiac, kidney, and neurological damage).

The second approach engineers T-cells with suicide genes/kill switches. These are genetic approaches that cause the engineered cell to die once a proper cue is provided. Several of them are based on introducing selective enzymatic metabolizers of toxic agents, such as herpes simplex virus thymidine kinase (HSV-tk). Additionally, the use of on an inducible caspase-9 protein that is activated using a specific chemical inducer of dimerization has been a promising approach to actively induced broad cell death. The major limitations with these approaches are they induce cell death in all target cells (thereby eliminating beneficial cells). Like conventional immunosuppression, they usually require the appearance of symptoms before implementation (and therefore possible permanent damages to the patient).

In contrast, the iCAR strategy describe herein selectively filters T-cell actions, restricting activity at off-target sites, while sparing therapeutic functionality against the intended target. As shown herein, iCARs were capable of inhibiting human alloreactive T-cells from attacking a "host" tissue in a novel in vitro and in vivo model using iPS-derived human fibroblasts. Unique surface anti gens present in GVHD target tissues (e.g., CD33 for the myeloid lineage or organ-specific antigens) but absent from the targeted malignancy, are candidates for iCAR targets to differentiate GVHD from GVT. Similarly, the results described herein show that iCAR-mediated inhibition successfully restricts the "on-target but off-tissue" effects of CAR engineered T-cells, examples of which include B-cell aplasia in leukemia patients treated with T-cells expressing a CD19-specific CAR (Kalos et al., Science translational medicine, 2011. 3(95): 95ra73), fatal acute respiratory distress syndrome (ARDS) thought to result from anti-ERBB2 CART-cell cross reactivity on lung epithelium (Morgan et al., Mol. Ther., 2010. 18(4): 843-51), and fatalities from cardiac myonecrosis in melanoma and myeloma patients treated with Mage-A3 TCRs (June, Update on Immunotherapy Trials for HIV and Cancer, in Recombinant DNA Advisory Committee, 2012). Recognizing a surface antigen that is expressed on cardiac cells or lung epithelium but absent from tumor cells, iCARs could potentially be used to protect from Mage-A3 TCR or anti-ERBB2 CAR cross reactivity, thus resurrecting otherwise promising therapeutics. Alternatively, as many tumors actively down-regulate HLA molecules to escape immune recognition, HLA-targeted iCARs have the potential to provide concurrent protection to several tissues.

An important requirement for the clinical applicability of iCARs is the maintenance of T-cell functionality despite previous signaling of the iCAR. Interestingly, iCAR-transduced T-cells were found to still mount a response against a target antigen after exposure to an inhibitory antigen. This reversibility mimics natural killer cell behavior, in which the phosphorylation state of signaling molecules rather than transcriptional states control rapid functional responses such as cytotoxicity. Anti-PD-1 and anti-CTLA4 antibodies are able to reverse the impaired function of anergized or exhausted T-cells, again arguing for the ability to temporally regulate T-cell responses. Additionally, biochemical analyses of PD-1 and CTLA-4 effects on the TCR complex have been shown to depend on phosphorylation states, downstream kinases, and motility rather than apoptosis. Both the in vitro and in vivo results demonstrated inhibition in response to off-target cells with sustained therapeutic functionality, although a possibility exists that some of the cells may be anergized. In addition to functioning in T-cells, CTLA4 and PD-1 also operate in B cells, macrophages, and dendritic cells. Thus, iCARs have the potential to manipulate other immune phenomena as well.

The iCARs of the present invention can be used as a dampening tool to limit systemic cytokine storms or immune cell responses, e.g., by introducing the antigen to the iCAR such as a recombinant PSMA-Ig infused into a patient. The PSMA-Ig can bind and activate the iCAR, and can thus temporarily inhibit the T cell activation. This can temporarily break the cyclic spiral that causes cytokines storms and allow the T cells to activate with limited systemic side effects. The iCARs have this functionality, as shown by crosslinking the iCAR.

The present invention utilizes physiological mechanism to restrict T-cell side effects. This approach mimics the restriction of T-cell reactivity that occurs naturally, and thus does not require elimination of precious therapeutically viable cells. The present approach that takes advantage of the multi-faceted functionality of cells as drugs, by using synthetic receptors that guide and direct T-cells to perform only desired functions. In conclusion, antigen-specific inhibitory receptors successfully limited T-cell proliferation, cytokine secretion, and cytotoxicity upon engagement of specific cell-surface antigens, thus conferring protection to a normal tissue while retaining critical TCR or CAR mediated therapeutic functions. Thus, iCARs provide a novel strategy to establish safer and more efficacious T-cell therapies in both autologous and allogeneic settings.

Graft-Versus-Leukemia Effect (GVL) and Graft-Versus-Host-Disease (GVHD)

Since the first use of allogeneic bone marrow transplants, it has been appreciated that the eradication of leukemia was dependent on the donor-derived immune response. The Graft versus leukemia effect (GVL) was further elucidated and appreciated following the success of donor lymphocyte infusion following allogeneic bone marrow transplantation (BMT). Donor lymphocyte infusion (DLI) is the most established and widespread use of adoptive immunotherapy for malignancy. Unfortunately, the main source of morbidity and mortality following DLI is the occurrence of Graft-versus-host-disease (GVHD). Reducing its incidence and severity is an important limitation to wider and potentially curative use of DLI in solid and hematological tumors. The iCAR strategy aims to solve this problem by separating the beneficial effects of GVL from the hazardous consequences of GVHD. GVHD primarily affects the skin, liver, and intestinal tract, sites that possess unique antigens such as minor alia-antigens that can be absent from the target malignancy. Such occurrences support a possible role for iCARs to separate the effects of GVL and GVHD.

In adoptive therapy, retargeted T-cells have been shown to play a potential curative role in several malignancies. Still, this transformative approach is limited because of the cross reactivity and subsequent toxicity against critical normal tissues (heart, lung). Thus, a significant need exists for developing ways to control T-cell reactivity without dampening their therapeutic function, which the iCAR strategy sets out to do. Recognizing a surface antigen that is expressed on cardiac cells or lung epithelium but absent from tumor cells, iCARs could potentially be used to protect from Mage-A3 TCR or anti-ERBB2 CAR cross reactivity, thus reviving otherwise promising therapeutics. Alternatively, as many tumors actively down-regulate HLA molecules to escape immune recognition, HLA-targeted iCARs could potentially provide concurrent protection to several tissues.

In one embodiment, allogeneic lymphocytes (with a degree of immunological mismatch) are engineered to express an iCAR targeting HLA-I, an antigen universally expressed in different tissues for treatment of metastatic breast cancer (a type of cancer with extremely active HLA-I down regulation). The patient is infused with the cells. The iCAR protects all normal or non-neoplastic tissues that express HLA-I, while the tumor is eliminated due negative or extremely low HLA-I expression.

In another embodiment, a patient undergoes HSCT for the treatment of a hematological malignancy or as adjuvant treatment for a solid tumor. The patient relapses or has residual disease, which is analyzed to be HLA-I negative or down regulated. Donor lymphocytes are engineered with an iCAR targeting HLA-I. The patient is infused with the cells. The iCAR protects all normal or non-neoplastic tissues that express HLA-I, while the tumor is eliminated due to negative or extremely low HLA-I expression.

In yet another embodiment, a patient has a tumor originating at a site that is not related to skin, liver, or gut cells (the major sites of GVHD related mortality). Donor lymphocyte cells are engineered with iCARs that target antigens expressed on skin, liver, or gut or all three. For example, if the tumor has undergone epithelium to mesenchymal transition (EMT), as is found with tumor progression and metastatic tumors, E-cadherin and cytokeratin have shown to be down regulated as part of this process. E-cadherin is highly expressed in normal skin, liver, and gut (Tsuchiya et al., Arch, Histol. Cytol., 69(2): 135-145(2006)). Therefore donor lymphocytes expressing an iCAR against E-cadherin, react in a GVL manner against the tumor, but are restricted in their ability to attack skin, liver, or gut.

Selection of Target Antigen for iCAR and CAR

The invention provides a method and a set of novel reagents to control responses of T-cells or other immune modulatory cells by using synthetic receptors that utilize signaling domains of immune inhibitory receptors (the iCAR). An appropriate antigen for the iCARs will at times utilize a personalized medicine approach due to natural variation in tumors. At the same time, depending on the use and type of iCAR, several potential "classes" of antigens have the potential to provide protection for several tissues at the same time. These include: (1) Universally expressed immunogenic antigens that are down regulated by tumors but not normal tissues, such as human leukocyte antigens (HLAs). (2) Antigens down regulated in tumor progression especially the attainment of a metastatic phenotype, but maintained in certain normal tissues. Such antigens include: (3) cell surface EMT antigens (such as E-cadherin and cytokeratins); (4) cell surface tumor suppressor antigens, such as OPCML (Cui et al., PLoS ONE. 2008; 3(8): e2990); and (6) other similar antigens such as HYAL2, DCC, SMAR1, and the like. OPCML-v1 is widely expressed at varying levels in all normal adult and fetal tissues (except for placenta and peripheral blood mononuclear cells). (7) Cell surface carbohydrates, lipids, and posttranslational modifications, such as mucin-type O-glycans (core 3 O-glycans) (Lee and Fukuda, Methods Enzymol. 2010; 479:143-54; Suzuki-Anekoji et al., J Biol Chem. 2011 Sep. 16; 286(37): 32824-33; Bao and Fukuda, Methods Enzymol. 20 1 0; 479:387-96). (8) Additionally, there many other processes disrupted in tumors (metabolism, apoptosis, trafficking, differentiation, and the like) that each lead to down regulation of surface antigens, any of these could be used as potential iCAR antigen targets.

In general, the invention provides a personal approach that can be taken to each patient. As described herein, the iCAR antigen can be selected through an algorithmic process, after which the physician can order a specific receptor suited for the patient's tumor. This receptor is then introduced alongside a stimulating receptor (ie TCR or CAR or GVL signals) to provide protection against a select tissue.

It is important to note that the iCAR may bind the same antigen as the activating CAR. For example, there could be a situation in which no antigens are found that are binary in their expression between the tumor and a normal tissue (i.e., totally absent on one and present on the other). Still, if an antigen on the tumor is expressed at a much higher level than the normal tissue, both the stimulating CAR and the iCAR receptor could then target that same antigen. In the case of the tumor, since there is a great deal of antigen, the stimulatory CAR would dominate and cause the tumor to be eliminated. In the case of the normal tissue, since the level of antigen expression is low, the iCAR could provide adequate inhibition. This is true because levels of both/or a single the target antigen and the levels of the stimulating and the iCAR can affect the outcome response of the immunoresponsive cell (FIG. 23). Additionally, changing the affinity of each receptor can be used to modulate and fine-tune the response.

Antigen disparity between a target and off target tissue can be limited with differences primarily in the level of expression rather than the absolute absence of expression. Additionally, variable expression levels can be expected if several tissues are represented with one common antigen for protection using an iCAR. One such example is the expression of HLA molecules, which are broadly found on the majority of cell types, but often with different levels of expression. Interestingly, down regulation of HLA molecules represents a major mechanism of tumor escape from T-cell immune responses. In such a scenario, DLI T-cells engineered with an iCAR against an HLA molecule that is down regulated on the malignancy could provide broad protection for a variety of tissue types from GVHD while maintaining a GVL effect.

The combinatorial possibilities of such antigen selection are only limited by the available antibodies, tumor surface antigen profiling, and known tissue specific antigens.

Cytotoxic T-Lymphocyte Antigen 4 (CTLA-4)

CTLA-4 is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities.

CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif able to bind PI3K, PP2A and SHP-2 and one proline-rich motif able to bind SH3 containing proteins. One role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

CTLA-4 can have an amino acid sequence as set forth in SEQ ID NO:5.

```
1   MACLGFQRHK AQLNLATRTW PCTLLFFLLF IPVFCKAMHV AQPAVVLASS RGIASFVCEY

61  ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN
```

In accordance with the present invention, a CTLA-4 polypeptide can have an amino acid sequence that is at least 85%, 90%, 95%, 96%, 97%, 98%, 99% or 100% homologous to SEQ ID NO:5 (homology herein may be determined using standard software such as BLAST or FASTA). In non-limiting embodiments, a CTLA-4 polypeptide can have an amino acid sequence that is a consecutive portion of SEQ ID NO:5 which is at least 20, or at least 30, or at least 40, or at least 50, and up to 222 amino acids in length. Alternatively or additionally, in non-limiting various embodiments, the CTLA-4 polypeptide has an amino acid sequence of amino acids 1 to 223, 1 to 50, 50 to 100, 100 to 140, 141 to 161, 162 to 182, 183 to 223, 141 to 223, 162 to 223, or 183 to 223 of SEQ ID NO:5. In one embodiment, the CTLA-4 polypeptide has an amino acid sequence of amino acids 183 to 223 of SEQ ID NO:5. In certain embodiments, the intracellular signaling domain of the iCAR includes a CTLA-4 polypeptide having an amino acid sequence of amino acids 183 to 223 of SEQ ID NO:5. In certain embodiments, the transmembrane domain of the iCAR includes a CTLA-4 polypeptide having an amino acid sequence of amino acids 162 to 182 of SEQ ID NO:5.

In accordance with the present invention, a "CTLA-4 nucleic acid molecule" refers to a polynucleotide encoding a CTLA-4 polypeptide.

Programmed Cell Death Protein 1 (PD-1)

PD-1 is a negative immune regulator of activated T cells upon engagement with its corresponding ligands PD-L1 and PD-L2 expressed on endogenous macrophages and dendritic cells. PD-1 is a type I membrane protein of 268 amino acids. PD-1 has two ligands, PD-L1 and PD-L2, which are members of the B7 family. The protein's structure includes an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, that PD-1 negatively regulates TCR signals. SHP-I and SHP-2 phosphatases bind to the cytoplasmic tail of PD-1 upon ligand binding. Upregulation of PD-L1 is one mechanism tumor cells may evade the host immune system. In pre-clinical and clinical trials, PD-1 blockade by antagonistic antibodies induced anti-tumor responses mediated through the host endogenous immune system.

PD-1 can have an amino acid sequence as set forth in SEQ ID NO:6.

In accordance with the present invention, a PD-1 polypeptide can have an amino acid sequence that is at least 85%, 90%, 95%, 96%, 97%, 98%, 99% or 100% homologous to SEQ ID NO:6. In non-limiting embodiments, a PD-1 polypeptide can have an amino acid sequence that is a consecutive portion of SEQ ID NO:6 which is at least 20, or at least 30, or at least 40, or at least 50, and up to 287 amino acids in length. Alternatively or additionally, in non-limiting various embodiments, a PD-1 polypeptide has an amino acid sequence of amino acids 1 to 288, 1 to 50, 50 to 100, 100 to 144, 145 to 170, 171 to 191, 192 to 288, 145 to 288, 171 to 288, or 192 to 288 of SEQ ID NO:6. In one embodiment, the PD-1 polypeptide has an amino acid sequence of amino acids 192 to 288 of SEQ ID NO:6. In certain embodiments, the intracellular signaling domain of the iCAR includes a PD-1 polypeptide having an amino acid sequence of amino acids 192 to 288 of SEQ ID NO:6. In certain embodiments, the transmembrane domain of the iCAR includes a PD-1 polypeptide having an amino acid sequence of amino acids 171 to 191 of SEQ ID NO:6.

In accordance with the present invention, a "PD-1 nucleic acid molecule" refers to a polynucleotide encoding a PD-1 polypeptide.

Lymphocyte-Activation Gene 3 (LAG-3)

Lymphocyte-activation protein 3 (LAG-3) is a negative immune regulator of immune cells. LAG-3 belongs to the immunoglobulin (Ig) superfamily and contains 4 extracellular Ig-like domains. The LAG3 gene contains 8 exons. The sequence data, exon/intron organization, and chromosomal localization all indicate a close relationship of LAG3 to CD4. LAG3 has also been designated CD223 (cluster of differentiation 223).

LAG-3 can have an amino acid sequence as set forth in SEQ ID NO:7.

```
1   mqipqapwpv vwavlqlgwr pgwfldspdr pwnpptfspa llvvtegdna tftcsfsnts 61  esfvlnwyrm spsngtdkla afpedrsqpg qdcrfrvtgl pngrdfhmsv vrarrndsgt 121 ylcgaislap kagikeslra elrvterrae vptahspsp rpagqfgtlv vgvvggllgs 181 lvllvwvlav icsraargti garrtgqplk edpsavpvfs vdygeldfqw rektpeppvp 241 cvpegteyat ivfpsgmgts sparrgsadg prsaqplrpe dghcswpl
```

```
  1 mweagflgll flqplwvapv kplqpgaevp vvwaqegapa qlpcsptipl qdlsllrrag
 61 vtwqhqpdsg ppaaapghpl apgphpaaps swgprprryt vlsvgpgglr sgrlplqprv
121 qldergrqrg dfslwlrpar radageyraa vhlrdralsc rlrlrlgqas mtasppgslr
181 asdwvilncs fsrpdrpasv hwfrnrgqgr vpvresphhh laesflflpq vspmdsgpwg
241 ciltyrdgfn vsimynltvl glepptpltv yagagsrvgl pcrlpagvgt rsfltakwtp
301 pgggpdllvt gdngdftlrl edvsqaqagt ytchihlqeq qlnatvtlai itvtpksfgs
361 pgslgkllce vtpvsgqerf vwssldtpsq rsfsgpwlea qeaqllsqpw qcqlyggerl
421 lgaavyftel sspgaqrsgr apgalpaghl llflilgvls llllvtgafg fhlwrrqwrp
481 rrfsaleqgi hppqaqskie eleqepepep epepepepep epeql
```

In accordance with the present invention, a LAG-3 polypeptide can have an amino acid sequence that is at least 85%, 90%, 95%, 96%, 97%, 98%, 99% or 100% homologous to SEQ ID NO:7. In non-limiting embodiments, a LAG-3 polypeptide can have an amino acid sequence that is a consecutive portion of SEQ ID NO:7 which is at least 20, or at least 30, or at least 40, or at least 50, and up to 524 amino acids in length. Alternatively or additionally, in non-limiting various embodiments, a LAG-3 polypeptide has an amino acid sequence of amino acids 1 to 525, 1 to 50, 50 to 100, 100 to 150, 150 to 200, 200 to 250, 250 to 300, 300 to 350, 350 to 400, 400 to 420, 421 to 450, 451 to 471, 472 to 525, 421 to 525, 451 to 525, or 472 to 525 of SEQ ID NO:7. In one embodiment, the LAG-3 polypeptide has an amino acid sequence of amino acids 472 to 525 of SEQ ID NO:7. In certain embodiments, the intracellular signaling domain of the iCAR includes a LAG-3 polypeptide having an amino acid sequence of amino acids 472 to 525 of SEQ ID NO:7. In certain embodiments, the transmembrane domain of the iCAR includes a LAG-3 polypeptide having an amino acid sequence of amino acids 451 to 471 of SEQ ID NO:7.

In accordance with the present invention, a "LAG-3 nucleic acid molecule" refers to a polynucleotide encoding a LAG-3 polypeptide.

Natural Killer Cell Receptor 2B4 (2B4)

Natural Killer Cell Receptor 2B4 (2B4) mediates non-MHC restricted cell killing on NK cells and subsets of T cells. To date, the function of 2B4 is still under investigation, with the 2B4-S isoform believed to be an activating receptor, and the 2B4-L isoform believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

2B4 can have an amino acid sequence as set forth in SEQ ID NO:8.

In accordance with the present invention, a 2B4 polypeptide can have an amino acid sequence that is at least 85%, 90%, 95%, 96%, 97%, 98%, 99% or 100% homologous to SEQ ID NO:8. In non-limiting embodiments, a 2B4 polypeptide can have an amino acid sequence that is a consecutive portion of SEQ ID NO:8 which is at least 20, or at least 30, or at least 40, or at least 50, and up to 369 amino acids in length. Alternatively or additionally, in non-limiting various embodiments, a 2B4 polypeptide has an amino acid sequence of amino acids 1 to 370, 1 to 50, 50 to 100, 100 to 150, 150 to 215, 216 to 229, 230 to 250, 251 to 370, 216 to 370, 230 to 370, or 251 to 370 of SEQ ID NO:8. In one embodiment, the 2B4 polypeptide has an amino acid sequence of amino acids 251 to 370 of SEQ ID NO:8. In certain embodiments, the intracellular signaling domain of the iCAR includes a 2B4 polypeptide having an amino acid sequence of amino acids 251 to 370 of SEQ ID NO:8. In certain embodiments, the transmembrane domain of the iCAR includes a 2B4 polypeptide having an amino acid sequence of amino acids 230 to 250 of SEQ ID NO:8.

In accordance with the present invention, a "2B4 nucleic acid molecule" refers to a polynucleotide encoding a 2B4 polypeptide.

B- and T-Lymphocyte Aftermath (BTLA)

B- and T-lymphocyte attenuator (BTLA) expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumour necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human CD8+

```
  1 mlgqvvtlil llllkvyqgk gcqgsadhvv sisgvplqlq pnsiqtkvds iawkkllpsq
 61 ngfhhilkwe ngslpsntsn drfsfivknl sllikaaqqq dsglyclevt sisgkvqtat
121 fqvfvfesll pdkvekprlq gqgkildrgr cqvalsclvs rdgnvsyawy rgskliqtag
181 nltyldeevd ingthtytcn vsnpvswesh tlnltqdcqn ahqefrfwpf lviivilsal
241 flgtlacfcv wrrkrkekqs etspkeflti yedvkdlktr rnheqeqtfp gggstiysmi
301 qsqssaptsq epaytlysli qpsrksgsrk rnhspsfnst iyevigksqp kaqnparlsr
361 kelenfdvys
``` cancer-specific T cells. BTLA has also been designated as CD272 (cluster of differentiation 272).

BTLA can have an amino acid sequence as set forth in SEQ ID NO:9.

```
  1 MKTLPAMLGT GKLFWVFFLI PYLDIWNIHG KESCDVQLYI KRQSEHSILA GDPFELECPV

61 KYCANRPHVT WCKLNGTTCV KLEDRQTSWK EEKNISFFIL HFEPVLPNDN GSYRCSANFQ

121 SNLIESHSTT LYVTDVKSAS ERPSKDEMAS RPWLLYRLLP LGGLPLLITT CFCLFCCLRR

181 HQGKQNELSD TAGREINLVD AHLKSEQTEA STRQNSQVLL SETGIYDNDP DLCFRMQEGS

241 EVYSNPCLEE NKPGIVYASL NHSVIGPNSR LARNVKEAPT EYASICVRS
```

In accordance with the present invention, a BTLA polypeptide can have an amino acid sequence that is at least 85%, 90%, 95%, 96%, 97%, 98%, 99% or 100% homologous to SEQ ID NO:9. In non-limiting embodiments, a BTLA polypeptide can have an amino acid sequence that is a consecutive portion of SEQ ID NO:9 which is at least 20, or at least 30, or at least 40, or at least 50, and up to 288 amino acids in length. Alternatively or additionally, in non-limiting various embodiments, a BTLA polypeptide has an amino acid sequence of amino acids 1 to 289, 1 to 50, 50 to 100, 100 to 134, 135 to 157, 158 to 178, 179 to 289, 135 to 289, 158 to 289, or 179 to 289 of SEQ ID NO:9. In one embodiment, the BTLA polypeptide has an amino acid sequence of amino acids 179 to 289 of SEQ ID NO:9. In certain embodiments, the intracellular signaling domain of the iCAR includes a BTLA polypeptide having an amino acid sequence of amino acids 179 to 289 of SEQ ID NO:9. In certain embodiments, the transmembrane domain of the iCAR includes a BTLA polypeptide having an amino acid sequence of amino acids 158 to 178 of SEQ ID NO:9.

In accordance with the present invention, a "BTLA nucleic acid molecule" refers to a polynucleotide encoding a BTLA polypeptide.

Hematopoietic Cell Lineages

Mammalian hematopoietic (blood) cells provide a diverse range of physiologic activities. Hematopoietic cells are divided into lymphoid, myeloid and erythroid lineages. The lymphoid lineage, comprising B, T and natural killer (NK) cells, provides for the production of antibodies, regulation of the cellular immune system, detection of foreign agents in the blood, detection of cells foreign to the host, and the like. The term "T cells" as used herein refers to lymphocytes that mature in the thymus and are chiefly responsible for cell-mediated immunity. T cells are involved in the adaptive immune system. The term "natural killer (NK) cells" as used herein refers to lymphocytes that are part of cell-mediated immunity and act during the innate immune response. They do not require prior activation in order to perform their cytotoxic effect on target cells. Cytotoxic T cells (CTL or killer T cells) are a subset of T lymphocytes capable of inducing the death of infected somatic or tumor cells.

Cells for Use in the Methods of the Invention

The present invention provides cells expressing a combination of an antigen-recognizing receptor that activates an immunoresponsive cell (e.g., TCR, CAR) and an inhibitory chimeric antigen receptor (iCAR), and methods of using such cells for the treatment of a disease that requires an enhanced immune response. In one approach, tumor antigen-specific T cells (all subsets including CD4, CD8, memory, naïve, effector, T-reg etc), cells of the innate immune system, NK cells, CTL cells or other immunoresponsive cells are used to express an iCAR that binds an antigen on non-tumor tissue, for the treatment or prevention of neoplasia. For example, a T cell expressing a chimeric antigen receptor 19-28z that recognizes CD19 is co-expressed in a T cell that expresses an iCAR that binds CD33. Such cells are administered to a human subject in need thereof for the treatment or prevention of blood cancers (e.g. leukemias, lymphomas, and myelomas). In another approach, viral antigen-specific T cells, NK cells, CTL cells can be used for the treatment of viral diseases. The cells can express a recombinant or an endogenous antigen receptor, which can be 19-28z that is specific for CD19, P28z that is specific for PSMA, M28z that is specific for Mesothelin, or 56-28z that is specific for CD56.

A patient's own T cells may be genetically modified to target tumors through the introduction of genes encoding artificial T cell receptors termed chimeric antigen receptors (CARs). CARs include CARs that activate an immune response and iCARs that suppress an immune response.

Tumor Antigen-Specific T Lymphocytes (and NK Cells)

Types of tumor antigen-specific human lymphocytes that can be used in the methods of the invention include, without limitation, peripheral donor lymphocytes genetically modified to express chimeric antigen receptors (CARs) (Sadelain, M., et al. 2003 Nat Rev Cancer 3:35-45), peripheral donor lymphocytes genetically modified to express a full-length tumor antigen-recognizing T cell receptor complex comprising the a and heterodimer (Morgan, R. A., et al. 2006 Science 314:126-129), lymphocyte cultures derived from tumor infiltrating lymphocytes (TILs) in tumor biopsies (Panelli, M. C., et al. 2000 J Immunol 164:495-504; Panelli, M. C., et al. 2000 J Immunol 164:4382-4392), and selectively in vitro-expanded antigen-specific peripheral blood leukocytes employing artificial antigen-presenting cells (AAPCs) or pulsed dendritic cells (Dupont, J., et al. 2005 Cancer Res 65:5417-5427; Papanicolaou, G. A., et al. 2003 Blood 102: 2498-2505). The T cells may be autologous, non-autologous (e.g., allogeneic), or derived in vitro from engineered progenitor or stem cells. T cells may prepared in bolk as commonly performed with Peripheral blood lymphocytes (PBL), or tumor infiltrating lymphocytes (TILs), T cells may be purified by using, e.g. CD4, CD8, CD62L.

Any suitable tumor antigen (antigenic peptide) is suitable for use in the tumor-related embodiments described herein. Sources of immune response activating antigens include, but are not limited to cancer proteins. The antigen can be expressed as a peptide or as an intact protein or portion thereof. The intact protein or a portion thereof can be native or mutagenized. Suitable immune response activating antigens include prostate specific membrane antigen (PSMA) and prostate stem cell anti gen (PCSA).

Viral Antigen-Specific T Lymphocytes (and NK Cells)

Suitable antigens for use in the treatment of pathogen infection or other infectious disease, for example, in an immunocompromised subject include, without limitation, viral antigens present in Cytomegalovirus (CMV), Epstein Barr Virus (EBV), Human Immunodeficiency Virus (HIV), and influenza virus.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. mAbs are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing d yes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

Accordingly, the invention generally provides an immunoresponsive cell, such as a virus specific or tumor specific T cell comprising a receptor that binds a first antigen and activates the immunoresponsive cell and a receptor that binds a second antigen and inhibits the immunoresponsive cell.

Vectors

Genetic modification of immunoresponsive cells (e.g., T cells, CTL cells, NK cells) can be accomplished by transducing a substantially homogeneous cell composition with a recombinant DNA or RNA construct. Preferably, a retroviral vector (either gamma retroviral or lentiviral) is employed for the introduction of the DNA or RNA construct into the host cell genome. For example, a polynucleotide encoding a receptor that binds an antigen (e.g., a tumor antigen, or a variant, or a fragment thereof), can be cloned into a retroviral vector and expression can be driven from its endogenous promoter, from the retroviral long terminal repeat, or from an alternative internal promoter. Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide tumor or viral antigen-specific cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a co-stimulatory ligand in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263 267, 1996; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:778-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the expression of a protein in cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1 α enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

Polypeptides and Analogs

Also included in the invention are αCD19, αPSMA, CD28, CD3ζ, CTLA-4, PD-1, and 19-28z polypeptides or fragments thereof that are modified in ways that enhance their anti-neoplastic activity (e.g., a humanized monoclonal antibody) or inhibit their cytotoxic activity (e.g., an iCAR) when expressed in an immunoresponsive cell. The invention provides methods for optimizing an amino acid sequence or nucleic acid sequence by producing an alteration in the sequence. Such alterations may include certain mutations, deletions, insertions, or post-translational modifications. The invention further includes analogs of any naturally-occurring polypeptide of the invention. Analogs can differ from a naturally-occurring polypeptide of the invention by amino acid sequence differences, by post-translational modifications, or by both. Analogs of the invention will generally exhibit at least 85%, 90%, 91%, 92%, 93%, 94%, 95%, 96%, 97%, 98%, 99% or more identity with all or part of a naturally-occurring amino, acid sequence of the invention. The length of sequence comparison is at least 5, 10, 15 or 20 amino acid residues, preferably at least 25, 50, or 75 amino acid residues, and more preferably more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., .beta. or .gamma. amino acids.

In addition to full-length polypeptides, the invention also provides fragments of any one of the polypeptides or peptide domains of the invention. As used herein, the term "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80, 100, 200, 300 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the invention. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference poly peptide. Preferably, the protein analogs are relatively resistant to in vivo degradation, resulting in a more prolonged therapeutic effect upon administration. Assays for measuring functional activity include, but are not limited to, those described in the Examples below.

Co-Stimulatory Ligands

The interaction with at least one co-stimulatory ligand provides a non-antigen-specific signal important for full activation of an immune cell (e.g., T cell). Co-stimulatory ligands include, without limitation, tumor necrosis factor (TNF) ligands, cytokines (such as IL-2, IL-12, IL-15 or IL21), and immunoglobulin (Ig) superfamily ligands. Tumor necrosis factor (TNF) is a cytokine involved in systemic inflammation and stimulates the acute phase reaction. Its primary role is in the regulation of immune cells. Tumor necrosis factor (TNF) ligands share a number of common features. The majority of the ligands are synthesized as type II transmembrane proteins (extracellular C-terminus) containing a short cytoplasmic segment and a relatively long extracellular region. TNF ligands include, without limitation, nerve growth factor (NGF), CD40L (CD40L)/CD154, CD1137L/4-1BBL, tumor necrosis factor alpha (TNFα), CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Biys/THANK/Tall-1, glucocorticoid-induced TNF Receptor ligand (GITRL), and TNF-related apoptosis-inducing ligand (TRAIL), LIGHT (TNFSFI4). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, without limitation, CD80, CD86 and ICOS, both ligands for CD28.

Administration

Compositions comprising genetically modified immunoresponsive cells of the invention (e.g., T cells, cells of the innate immune system, NK cells, CTL cells, or their progenitors) can be provided systemically or directly to a subject for the treatment of a neoplasia, pathogen infection, or infectious disease. In one embodiment, cells of the invention are directly injected into an organ of interest (e.g., an organ affected by a neoplasia). Alternatively, compositions comprising genetically modified immunoresponsive cells are provided indirectly to the organ of interest, for example, by administration into the circulatory system (e.g., the tumor vasculature). Expansion and differentiation agents can be provided prior to, during or after administration of the cells to increase production of T cells, cells of the innate immune system, NK cells, or CTL cells in vitro or in vivo.

The modified cells can be administered in any physiologically acceptable vehicle, normally intravascularly, although they may also be introduced into bone or other convenient site where the cells may find an appropriate site for regeneration and differentiation (e.g., thymus). Usually, at least $1\times10^5$ cells will be administered, eventually reaching $1\times10^{10}$ or more. Genetically modified immunoresponsive cells of the invention can comprise a purified population of cells. Those skilled in the art can readily determine the percentage of genetically modified immunoresponsive cells in a population using various well-known methods, such as fluorescence activated cell sorting (FACS). Preferable ranges of purity in populations comprising genetically modified immunoresponsive cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Dosages can be readily adjusted by those skilled in the art (e.g., a decrease in purity may require an increase in dosage). The cells can be introduced by injection, catheter, or the like. If desired, factors can also be included, including, but not limited to, interleukins, e.g. IL-2, IL-3, IL 6, IL-11, IL7, IL12, IL15, IL21, as well as the other interleukins, the colony stimulating factors, such as G-, M- and GM-CSF, interferons, e.g. gamma.-interferon and erythropoietin.

Compositions of the invention include pharmaceutical com positions comprising genetically modified immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells of the invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition containing a genetically modified immunoresponsive cell), it will generally be formulated in a unit dosage injectable form (solution, suspension, emulsion).

Formulations

Compositions of the invention comprising genetically modified immunoresponsive cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified immunoresponsive cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the genetically modified immunoresponsive cells or their progenitors.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the genetically modified immunoresponsive cells as described in the present invention. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of genetically modified immunoresponsive cells of the invention is the quantity of cells necessary to achieve an optimal effect. The quantity of cells to be administered will vary for the subject being treated. In a one embodiment, between $10^4$ to $10^{10}$ between $10^5$ to $10^9$ or between $10^6$ and $10^8$ genetically modified immunoresponsive cells of the invention are administered to a human subject. More effective cells may be administered in even smaller numbers. In some embodiments, at least about $1\times10^8$, $2\times10^8$, $3\times10^8$, $4\times10^8$, and $5\times10^8$ genetically modified immunoresponsive cells of the invention are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the invention. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Methods of Treatment

Provided herein are methods for treating neoplasia in a subject. Also contemplated herein are methods for treating a pathogen infection or other infectious disease in a subject, such as an immunocompromised human subject. The methods comprise administering a T cell, a cell of the innate immune system, NK cell, or CTL cell of the invention in an amount effective to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art.

Several factors are typically taken into account when determining an appropriate dosage to achieve an effective amount. These factors include age, sex and weight of the subject, the condition being treated, the severity of the condition and the form and effective concentration of the antigen-binding fragment administered.

For adoptive immunotherapy using antigen-specific T cells, cell doses in the range of $10^6$-$10^{10}$ (e.g., $10^9$) are typically infused. Upon administration of the genetically modified cells into the host and subsequent differentiation, T cells are induced that are specifically directed against the specific antigen. "Induction" of T cells can include inactivation of antigen-specific T cells such as by deletion or anergy. Inactivation is particularly useful to establish or reestablish tolerance such as in autoimmune disorders. The modified cells can be administered by any method known in the art including, but not limited to, intravenous, subcutaneous, intranodal, intratumoral, intrathecal, intrapleural, intraperitoneal and directly to the thymus.

Therapeutic Methods

The invention provides methods for increasing an immune response in a subject in need thereof. In one embodiment, the invention provides methods for treating or preventing a neoplasia in a subject. The invention provides therapies that are particularly useful for the treatment of subjects having blood cancers (e.g. leukemias, lymphomas, and myelomas) or ovarian cancer, that are not amenable to conventional therapeutic interventions. Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in this invention is administered to these subjects to elicit an anti-tumor response, with the objective of palliating their condition. Ideally, reduction in turn or mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of neoplasia, but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor has invaded neighboring tissues, or who show involvement of lymph nodes.

Another group have a genetic predisposition to neoplasia but have not yet evidenced clinical signs of neoplasia. For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

Human neoplasia subjects having any of the following neoplasias: glioblastoma, melanoma, neuroblastom a, adenocarcinoma, glioma, soft tissue sarcoma, and various carcinomas (including prostate and small cell lung cancer) are especially appropriate subjects. Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma. seminoma. embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Accordingly, the invention provides a method of treating or preventing a neoplasia in a subject, the method comprising administering an effective amount of an immunoresponsive cell comprising a receptor that binds a tumor antigen and activates the immunoresponsive cell (e.g., TCR, CAR) and a vector encoding an inhibitory chimeric antigen receptor (iCAR) that binds a target antigen and suppresses the immunoresponsive cell. As a consequence of surface expression of a receptor that binds a tumor antigen and activates the immunoresponsive cell (e.g., TCR, CAR) and a vector encoding an inhibitory chimeric antigen receptor (iCAR) that binds a target antigen and suppresses the immunoresponsive cell, adoptively transferred human T or NK cells are endowed with selective cytolytic activity.

In one embodiment, the neoplasia is selected from the group consisting of blood cancers (e.g. leukemias, lymphomas, and myelomas), ovarian cancer, sarcoma, and acute myeloid leukemia (AML), prostate cancer, breast cancer, bladder cancer, brain cancer, colon cancer, intestinal cancer, liver cancer, lung cancer, pancreatic cancer, prostate cancer, skin cancer, stomach cancer, glioblastoma, and throat cancer. In another embodiment, the tumor antigen is one or more of carbonic anhydrase IX (CA1X), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Ra2), K-light chain, kinase insert domain receptor (KDR), Lewis Y (LeY), L1 cell adhesion molecule (L1CAM), melanoma antigen family A, 1 (MAGE-Al), Mucin 16 (Muc-16), Mucin 1 (Muc-1), Mesothelin (MSLN), NKG2D ligands, cancer-testis antigen NY-ESO-1, on cofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), or Wilms tumor protein (WT-1).

In other embodiments, the invention provides methods for treating subjects with a pathogen infection (e.g., viral infection, bacterial infection, fungal infection, parasite infection, or protozoal infection). The invention is particularly useful for enhancing an immune response in an immunocompromised subject. Exemplary viral infections susceptible to treatment using a method of the invention include, but are not limited to, Cytomegalovirus (CMV), Epstein Barr Virus (EBV), Human Immunodeficiency Virus (HIV), and influenza virus infections. Accordingly, the invention provides a method of treating or preventing a pathogen infection in a subject, the method comprising administering an effective amount of an immunoresponsive cell as described herein.

Kits

The invention provides kits for the treatment or prevention of a neoplasia, pathogen infection, immune disorder or allogeneic transplant. In one embodiment, the kit includes a therapeutic or prophylactic composition containing an effective amount of an immunoresponsive cell comprising an activating antigen receptor and an inhibitory chimeric antigen receptor (iCAR) in unit dosage form. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired the immunoresponsive cell is provided together with instructions for administering the cell to a subject having or at risk of developing a neoplasia, pathogen infection, immune disorder or allogeneic transplant. The instructions will generally include information about the use of the composition for the treatment or prevention of neoplasia, pathogen infection, immune disorder or allogeneic transplant. In other embodiments, the instructions include at least one of the following: description of the therapeutic agent; dosage schedule and administration for treatment or prevention of a neoplasia, pathogen infection, immune disorder or allogeneic transplant or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, I 996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1

Inhibitory Chimeric Antigen Receptor (iCAR) Divert Off-Target Responses

Summary

T cell therapies have demonstrated long-term efficacy and curative potential for the treatment of some cancers. However, their use is limited by damage to bystander tissues, as seen in graft-versus-host disease after donor lymphocyte infusion, or "on-target, off-tumor" toxicities incurred in some engineered T cell therapies. Non-specific immunosuppression and irreversible T cell elimination are currently the only means to control such deleterious responses, but at the cost of abrogating therapeutic benefits or causing secondary complications. On the basis of the physiological paradigm of immune inhibitory receptors, antigen-specific inhibitory chimeric antigen receptors (iCARs) were designed to preemptively constrain T cell responses. The results as presented below demonstrate that CTLA-4- or PD-1-based iCARs can selectively limit cytokine secretion, cytotoxicity, and proliferation induced through the endogenous T cell receptor or an activating chimeric receptor. The initial effect of the iCAR is temporary, thus enabling T cells to function upon a subsequent encounter with the antigen recognized by their activating receptor. iCARs thus provide a dynamic, self-regulating safety switch to prevent, rather than treat, the consequences of inadequate T cell specificity.

Introduction

T cell therapies have shown clinical efficacy in bone marrow and organ transplantation, cancer immunotherapy, viral infections, and autoimmune diseases (1-6). Unfortunately, T cells may also engage in deleterious side effects. "On-target but off-tumor" adverse events have been reported in cancer immunotherapy clinical trials using both T cell receptor (TCR)- and chimeric antigen receptor (CAR)-engineered T cells. These include B cell aplasia in chronic lymphocytic leukemia patients treated with T cells expressing anti-CD19 CAR (7-9), fatal acute respiratory distress syndrome after anti-ERBB2 CAR T cell infusion thought to result from cross-reactivity on lung epithelium (10), and TCR-induced fatalities from cardiac myonecrosis or neurological toxicity incurred in patients treated with TCRs recognizing cancer-testis antigens (11-13). Similarly, the curative gains of donor lymphocyte infusion (DLI) in allogeneic bone marrow transplantation are hampered by the induction of both acute and chronic graft-versus-host disease (GVHD) and bone marrow aplasia (14). Strategies to separate the beneficial effects of graft versus tumor (GVT) from GVHD have met with limited success to date (15).

The current approach to curb T cell-mediated toxicities relies on the use of immunosuppressive regimens such as high-dose corticosteroid therapy, which exert cytostatic or cytotoxic effects on T cells, to restrain immune responses (16). Although effective, this approach fails to discriminate between beneficial and deleterious T cell functions. Additionally, immunosuppressive drugs cause substantial secondary side effects, such as susceptibility to infections, and cardiac, kidney, and neurological damage (14). Suicide gene engineering strategies, which may use selective enzymatic metabolizers of toxic agents, such as herpes simplex virus thymidine kinase (17) or inducible caspase-9 (18), or antibody-mediated depletion strategies targeting ectopic epitopes engineered into T cells (19, 20), also eliminate T cells indiscriminately of their therapeutic efficacy. Furthermore, these approaches are reactive because they are implemented after observing deleterious side effects. Strategies that prevent unwanted T cell reactivity are thus highly desirable.

Physiological regulation of T cell activation is accomplished by several mechanisms that include immune inhibitory receptors, which play a pivotal role in attenuating or terminating T cell responses (21, 22). Inhibitory receptors can be upregulated during T cell priming to taper immune responses or basally expressed to regulate activation thresholds. Thus, mice deficient for the inhibitory receptor CTLA-4 display massive T cell activation and proliferation and eventually succumb to severe systemic autoimmune disease with infiltration of activated T cells (23). Similarly, loss of PD-1, another inhibitory receptor specifically expressed on activated T cells, causes progressive arthritis and glomerulonephritis in C57BL/6 mice and accelerated insulitis in nonobese diabetic (NOD) mice (24, 25). Modulation of these receptors and their downstream signaling pathways has substantial influence on T cell functions. In vitro ligation of CTLA-4 or PD-1 during T cell stimulation blocks activation, cytokine release, and proliferation (26). Notably, anti-CTLA-4 and anti-PD-1 antibodies have shown clinical promise by derepressing anti-T cell responses in some patients with melanoma, lung, and renal cancer (22, 27, 28). Blockade of both CTLA-4 and PD-1 is also being actively investigated for reversing immune dysfunction and viral persistence in chronic hepatitis B and HIV infection (29, 30). However, similar to nonspecific immunosuppression, antibody-mediated inhibitory receptor checkpoint blockade is not antigen-specific and therefore does not discern between beneficial and deleterious T cell populations.

A genetic engineering strategy was used to harness the natural T cell inhibition physiology and regulate T cell responses in an antigen-selective manner. An inhibitory chimeric antigen receptor (CAR (iCAR)) having a surface antigen recognition domain combined with a powerful acute inhibitory signaling domain to limit T cell responsiveness despite concurrent engagement of an activating receptor was designed (FIG. 1A). As shown below, in human primary T cells, that PD-1- and CTLA-4-based iCARs reversibly restrict critical TCR or activating CAR functions, and thus allow for discrimination between target and off-target cells in vitro and in vivo.

Materials and Methods

Study Design

The purpose of this study was to create a synthetic receptor that could limit T cell toxicity toward a target cell in an antigen-dependent and reversible manner. Two such receptors using intracellular tails of CTLA-4 or PD-1 and an scFv targeting domain (against PSMA) were designed and were analyzed whether they could block (i) TCR- or (ii) CAR-driven T cell functionality in vitro and in vivo. In vitro, the focus was on analyzing (i) cytotoxicity, (ii) cytokine secretion, and (iii) T cell proliferation. In vivo experiments analyzed the integrated ability of the iCAR to protect a cellular target using live imaging and endpoint analysis (dictated by the untreated group of mice). The experimental procedures were approved by the Institutional Animal Care and Use Committee of Memorial Sloan-Kettering Cancer Center (MSKCC). The general design of the experiments was to expose T cells (expressing iCARs or the control Pdel receptor) to target cells (that expressed or lacked PSMA) and compare the groups trying to interrogate iCAR function, always in the presence of internal controls. T cells lacking iCARs were limited from contaminating the results by sorting T cells to be iCAR or iCAR/CAR double-positive (using reporter genes). Each experiment was performed multiple times using different donor T cells (T cells were never pooled). In most cases, data using a representative experiment (with sample replicates of more than three) were presented to avoid confounding variables such as differences due to transduction and sorting efficiencies, donor-related variability, and E/T ratios.

Inhibitory Chimeric Antigen Receptor (iCAR) Design

Each Inhibitory Chimeric Antigen Receptor (iCAR) was designed with the UniProt sequence annotation using two approaches. First, using commercial gene synthesis or cDNAs, the intracellular domain of each receptor was cloned in place of the CD28/CD3ζ domain of the previously described Pz1 receptor (Stephan et al., Nature medicine, 2007. 13(12): 1440-9), thus utilizing the CD8 transmembrane and hinge domains. A CD8 polypeptide can have an amino acid sequence as set forth below:

[SEQ ID NO: 11]
MALPVTALLLPLALLLHAARPSQFRVSPLDRTWNLGETVELKCQVLLSNP

TSGCSWLFQPRGAAASPTFLLYLSQNKPKAAEGLDTQRFSGKRLGDTF

VLTLSDFRRENEGYYFCSALSNSIMYFSHFVPVFLPAKPTTTPAPRPPTP

APTIASQPLSLRPEACRPAAGGAVHTRGLDFACDIYIWAPLAGTCGVLLL

SLVITLYCNHRNRRRVCKCPRPVVKSGDKPSLSARYV

The CD8 transmembrane and hinge domains can have an amino acid sequence of amino acids 137 to 209 of SEQ ID NO: 11. Alternatively or additionally, CD4 transmembrane and hinge domains may also be used and were tested. Nucleic acid sequences and amino acid sequences of iCAR constructs are provided at Appendix A. Alternatively, the transmembrane domains and the amino acids up to the first annotated extracellular topological domain (for PD-1 amino acids 145 to 288: for CTLA4 amino acids 161 to 223) were included, so as to utilize the endogenous hinge region of each receptor. These constructs were cloned into the P28z vector after the PSMA scFv. No significant functional differences were observed between the receptors generated by the two approaches. Additionally, versions of each iCAR were created that lacked any targeting domain, but retained the transmembrane and intracellular portions of each receptor, were created. The control Pdel receptor was designed by excising the CD28/CD3ζ domain of P-28z(34). iCARs should be clearly distinguished from CARs, all of which trigger T cell activation, in stark contrast to iCARs. The nucleic acid sequence of the PSMA scFv is provided below:

[SEQ ID NO: 12]
atggCTCTCCCAGTGACTGCCCTACTGCTTCCCCTAGCGCTTCTCCTGCA

TGCAGAGGTGCAGCTGCAGcagtcaggacctgaactggtgaagcctggga cttcagtgaggatatcctgcaagacttctggatacacattcactgaatat accatacactgggtgaagcagagccatggaaagagccttgagtggattgg aaacatcaatcctaacaatggtggtaccacctacaatcagaagttcgagg acaaggccacattgactgtagacaagtcctccagtacagcctacatggag ctccgcagcctaacatctgaggattctgcagtctattattgtgcagctgg ttggaactttgactactggggccaagggaccacGGTCACCgtctcctcag gtggaggTggAtcaggTggaggtggAtctggTggAggTggatcTGACATT

GTGATGACCCAGTCTCACAAATTCATGTCCACATCAGTAGGAGACAGGGT

CAGCATCATCTGTAAGGCCAGTCAAGATGTGGGTACTGCTGTAGACTGGT

ATCAACAGAAACCAGGACAATCTCCTAAACTACTGATTTATTGGGCATCC

ACTCGGCACACTGGAGTCCCTGATCGCTTCACAGGCAGTGGATCTGGGAC

AGACTTCACTCTCACCATTACTAATGTTCAGTCTGAAGACTTGGCAGATT

ATTTCTGTCAGCAATATAACAGCTATCCCCTCACGTTCGGTGCTGGGACC

ATGCTGGACCTGAAACGGgcggccgcA

The amino acid sequence of the PSMA scFv is provided below.

[SEQ ID NO: 13]
MALPVTALLLPLALLLHAEVQLQQSGPELVKPGTSVRISCKTSGYTFTEY

TIHWVKQSHGKSLEWIGNINPNNGGTTYNQKFEDKATLTVDKSSSTAYME

LRSLTSEDSAVYYCAAGWNFDYWGQGTTVTVSSGGGGSGGGGSGGGGSDI

VMTQSHKFMSTSVGDRVSIICKASQDVGTAVDWYQQKPGQSPKLLIYWAS

TRHTGVPDRFTGSGSGTDFTLTITNVQSEDLADYFCQQYNSYPLTFGAGT

MLDLKRAAA

The receptors, e.g., PD-1, CTLA-4, 2B4, LAG-3 and BTLA-4, were also tested with a CD19 target scFV. The nucleic acid sequence of the CD19 scFV is provided below:

[SEQ ID NO: 14]
ATGGCTCTCCCAGTGACTGCCCTACTGCTTCCCCTAGCGCTTCTCCTGC

ATGCAGAGGTGAAGCTGCAGCAGTCTGGGGCTGAGCTGGTGAGGCCTGG

GTCCTCAGTGAAGATTTCCTGCAAGGCTTCTGGCTATGCATTCAGTAGC

TACTGGATGAACTGGGTGAAGCAGAGGCCTGGACAGGGTCTTGAGTGGA

TTGGACAGATTTATCCTGGAGATGGTGATACTAACTACAATGGAAAGTT

CAAGGGTCAAGCCACACTGACTGCAGACAAATCCTCCAGCACAGCCTAC

```
-continued
ATGCAGCTCAGCGGCCTAACATCTGAGGACTCTGCGGTCTATTTCTGTG

CAAGAAAGACCATTAGTTCGGTAGTAGATTTCTACTTTGACTACTGGGG

CCAAGGGACCACGGTCACCGTCTCCTCAGGTGGAGGTGGATCAGGTGGA

GGTGGATCTGGTGGAGGTGGATCTGACATTGAGCTCACCCAGTCTCCAA

AATTCATGTCCACATCAGTAGGAGACAGGGTCAGCGTCACCTGCAAGGC

CAGTCAGAATGTGGGTACTAATGTAGCCTGGTATCAACAGAAACCAGGA

CAATCTCCTAAACCACTGATTTACTCGGCAACCTACCGGAACAGTGGAG

TCCCTGATCGCTTCACAGGCAGTGGATCTGGGACAGATTTCACTCTCAC

CATCACTAACGTGCAGTCTAAAGACTTGGCAGACTATTTCTGTCAACAA

TATAACAGGTATCCGTACACGTCCGGAGGGGGACCAAGCTGGAGATCA

AACGGgcggccgcA
```

The amino acid sequence of the CD19 scFV is provided below:

```
                                              [SEQ ID NO: 15]
MALPVTALLLPLALLLHAEVKLQQSGAELVRPGSSVKISCKASGYAFSSY

WMNWVKQRPGQGLEWIGQIYPGDGDTNYNGKFKGQATLTADKSSSTAYMQ

LSGLTSEDSAVYFCARKTISSVVDFYFDYWGQGTTVTVSSGGGGSGGGGS

GGGGSDIELTQSPKFMSTSVGDRVSVTCKASQNVGTNVAWYQQKPGQSPK

PLIYSATYRNSGVPDRFTGSGSGTDFTLTITNVQSKDLADYFCQQYNRYP

YTSGGGTKLEIKRAAAMALPVTALLLPLALLLHAEVKLQQSGAELVRPGS

SVKISCKASGYAFSSYWMNWVKQRPGQGLEWIGQIYPGDGDTNYNGKFKG

QATLTADKSSSTAYMQLSGLTSEDSAVYFCARKTISSVVDFYFDYWGQGT

TVTVSSGGGGSGGGGSGGGGSDIELTQSPKFMSTSVGDRVSVTCKASQNV

GTNVAWYQQKPGQSPKPLIYSATYRNSGVPDRFTGSGSGTDFTLTITNVQ

SKDLADYFCQQYNRYPYTSGGGTKLEIKRAAA
```

The PSMA target scFV and the CD19 target scFV can be exchanged due to the modular nature of the iCARs, as long as appropriate structural consideration are appreciated.

Conjugation Assay, Western Blots, and GAM Staining.

Cell-surface expression of each iCAR was analyzed using a previously described goat anti mouse stain protocol (Markley et al., Blood, 2010. 115(17): 3508-19). Cellular conjugation assay was performed as previously described (Burshtyn and Davidson, Natural killer cell conjugate assay using two-color flow cytometry. Methods in molecular biology, 2010. 612: 89-96). Briefly, EL4 or EL4-PSMA cells were labeled with the lipophilic DiD dye (Invitrogen) and mixed at a 1:1 ratio with T-cells in FACS tubes, incubated at 37° C. for 5 minutes, and analyzed on a flow cytometer. Western blot analysis was performed using standard protocols with a Bio-rad Mini-PROTEAN Tetra system. Intracellular tail of CTLA-4 was detected using polyclonal antibody C-19 that recognizes the CTLA-4 terminus (Santa Cruz Biotechnology).

Retroviral Vectors and Viral Production

Plasmids encoding the SFG oncoretroviral vector were prepared using standard molecular biology techniques. Synthesis of 19-28z-IRES-LNGFR, CD19, PSMA, GFP, mCherry and click-beetle-luciferase (CBL) vectors have been described (Markley et al., Blood, 2010. 115(17): 3508-19; Stephan et al., Nature medicine, 2007. 13(12): 1440-9; Brentjens et al., Clin. Cancer Res., 2007. 13(18:1): 5426-35). Retroviral producers were prepared from plasmid-transfected 1129 cell supernatant (Stephan et al., Nature medicine, 2007. 13(12): 1440-9).

Cell Lines

EL4-CD19, EL4-PSMA and the artificial antigen presenting cells (AAPC) NIH3T3-CD19 and NIH3T3-PSMA have been described (Gade (2005); Stephan et al., Nature medicine, 2007. 13(12): 1440-9; Maher et al., Nature Biotechnology, 2002. 20(1): 70-75; Markley et al., Blood, 2010. 115(17): 3508-19; Brentjens et al., Clin. Cancer Res., 2007. 13(18:1): 5426-35). NIH3T3-CD19-PSMA, NIH3T3-CD19-mCherry, NIH3T3-CD19-GFP, and NIH3T3-CD19-CBL as well as NALM/6-CBL and NALM/6-PSMA-CBL were obtained after transduction with respective retroviral supernatants of H29 producer cells. All comparative groups of cell lines were sorted for equivalent expression of CD19, GFP, or mCherry using a MoFlo sorter.

Peripheral Blood Leukocyte (PBL) Collection and Retroviral Transduction

Peripheral blood was obtained from healthy donors after informed consent under a protocol approved by the Memorial Sloan-Kettering Cancer Center (MSKCC) institutional review board. PBLs were isolated using Ficoll-Paque and activated with phytohemagglutinin (PHA) for 48 hr. Activated T-cells were transduced on three consecutive days by centrifugation in retronectin-coated (Takara), retroviral vector-bound plates. Cells were fed every 3 days with RPMI media supplemented with 20 U of IL-2. Ten days post-transduction, FACS selection based on enhanced GFP (marking the iCARs) and LNGFR (marking 19-28z) was used to isolate positive cells on a MoFlo sorter. Post-sort analysis was carried out to ensure equivalent expression of both reporters.

Generation of iPS Derived, Fibroblasts

Peripheral blood lymphocytes were activated with PHA, transduced with retroviral supernatants (f-citrine-P2A-Myc-E2A-Sox2 and f-vexGFP-P2A-Okt4-T2A-Klf4), and plated after 24 hours on MEF feeder cells (Themeli (2013)). Medium was changed to human ES Medium with fibroblast growth factor (FGF) (8 ng/ml) at day 5 after transduction and half media changed was performed daily after that. T-iPS colonies appeared at approximately 22-25 days after transduction. A subcutaneous xenograft teratoma assay was performed using the T-iPS-1.10 cell line. At three months, the teratoma was removed and treated with 100 U/ml of collagenase (Invitrogen) and 2 U/ml of dispase (Invitrogen) for two hours at 37° C. to generate a single cell suspension. The cells were sorted for HLA-ABC-positive cells, and after one week in culture in RPMI supplemented with 1% L-glutamine, 1% penicillin, 1% streptomycin and 10% fetal bovine serum (FBS), they reproducibly spontaneously generated the iPS-fib.

Flow Cytometry

All flow cytometry analysis was done on a LSRII cytometer (BD Biosciences) and analyzed on FlowJo software, Ver. 9.6 (TreeStar). Anti-human LNGFR, CD45, CD140b, CD10, HLA-ABC, HLA-DR, CD80, CD86, and CD62L were obtained from BD Biosciences; anti-human CD4, CD8, CD3, CD19, CD90, and 4',6-diamidino-2-phenylindole (DAPI) were obtained from Invitrogen; anti-human PSMA was obtained from Medical & Biological Laboratories; anti-human CCR7 was obtained from R&D; anti-human Foxp3 (236A/E7), and Foxp3 isotype were obtained from eBioscience.

In Vitro T-Cell Assays

In general for proliferation, effector cytokine production assays, and cytotoxicity assays, serial dilutions of sort purified T-cells were seeded on respective AAPCs (irradiated with 40-50Gy and seeded 24 hours earlier at $3\times10^4$/well) in 96-well flat-bottom plates (with outside wells of the plate containing media only to minimize effects of evaporation). iPS-Fibroblasts were not irradiated when used as targets. Fresh medium was added every 3-4 days or upon medium color changes. Cytokine production was quantified either by enzyme-linked immunosorbent assay (ELISA) kits (eBioscience) or Luminex assays (Invitrogen) as stated in the text according to manufacturer instructions. T-cell counts calculated using viable cell number (DAPI) and CountBright beads (Invitrogen) on a LSR II flow cytometer (BD) by collecting whole wells. All in vitro culture experiments were done in RPMI supplemented with 1% L-glutamine, 1% penicillin, 1% streptomycin and 10% FBS. No exogenous cytokines were administered at any time unless explicitly stated.

Luciferase CTL Assay

Cytotoxic T lymphocyte (CTL) assays using bioluminescence as the readout were performed as previously described (Fu et al., PloS one, 2010. 5(7): e11867). Briefly, all in vitro luciferase assays were performed with the Bright-Glo Luciferase Assay System (Promega) and 96-well Optical Bottom Black Microplates (Nuns), and were conducted according to the manufacturer's protocol with minor adjustments. All targets cells were engineered to express CBL with aGFP reporter to ensure equivalent levels of expression. Culture media was removed to 50 µl per well, 50 µl of prepared luciferase reagent was added to each well of the 96-well plates and the plates were incubated for 5 minutes to completely lyse the cells. Measurements were carried out with the IVIS Imaging System 100 Series (Xenogen). Living Image software version 2.6 (Xenogen) was used to quantify photon emission intensities.

Time Lapse and Fluorescence Microscopy CTL

All microscopy imaging was performed using a Zeiss AxioVert 200M equipped with a live imaging system. Time-lapse videos were acquired and compiled using Multi-Dimensional Acquisition in MetaMorph software (Molecular Devices). For CTL experiments, the signal from mCherry-positive AAPCs was quantitated using the Integrated Morphometric Analysis function in MetaMorph.

moDCs and Priming

Monocyte derived dendritic cells were generated using the Mo-DC Generation Tool Box (Miltenyi) from the same donor as the T-iPS cells. The moDCs were pulsed for 24 hours at the immature stage (Day 5-6) with lysates from iPS-Fib, which were generated through six freeze-thaw cycles. The maturation of the DCs was confirmed by flow cytometry of CD8O, CD86 and HLA-DR. Priming was performed as previously described (Yuan et al., Journal of immunology, 2005. 174(2): 758-66). Briefly, first round of priming was done using 1:30 T-cell/moDC ratio, with the second round using 1:10 to 1:30 ratio. RPMI supplemented with 1% L-glutamine, 1% penicillin, 1% streptomycin, 10% human AB serum (CellGro) and 5 ng/ml human IL-15 (R&D Systems) was used. On day three, 20 U/ml of IL-2 was added.

Proteome Profiler Array

T cells were exposed to AAPCs at an E/T ratio of 4:1 for 60 min, washed, lysed, and incubated (100 µg) on the Human Phospho-Immunoreceptor Array according to the manufacturer's protocol (R&DSystems). All blots were detected using chemiluminescence on the same x-ray film to standardize exposure levels. Scanned x-ray film images were analyzed with image analysis software. All pixel density was normalized on each array with internal pY controls.

Mouse Models and Quantitative Bioluminescence

For the NALM/6 studies, 6-12 week-old male NOD/SCID/$\gamma_c^-$ mice (Jackson Laboratory) were inoculated intravenously with $5\times10^5$ tumor cells (same dose for either single tumor or mixed tumor experiments). NALM/6 cells were engineered to express CBL with a GFP reporter. Four days later, $3\times10^5$ sorted T-cells were infused intravenously; cell dose was based on the percent GFP$^+$ 19-28z$^+$ as confirmed by post-sort analysis. Mice were sacrificed at 21 days (no T-cells controls display hind limb paralysis). For iPS-fibs studies, 6-12 week old male NOD/SCID/$\gamma_c$ (null) mice were inoculated intraperitoneally with $1\times10^6$ cells prepared in a 1:1 mixture of ice cold RPMI and Matrigel mixture (BD Biosciences). Eight days later, $5\times10^5$ twice moDC primed GFP sorted T-cells were infused intraperitoneally; cell dose was based on the percent GFP$^+$ as confirmed by post-sort analysis. Additionally, an in vitro luciferase CTL assay was performed to establish equivalent allogeneic reactivity in all groups using iPS-Fib as a target. In both models D-luciferin (Xenogen, 150 mg/kg intraperitoneally) was used as a substrate for click beetle luciferase, and bioluminescence images were collected on an IVIS 100 Imaging System. Living Image software Version 2.6 was used to acquire and quantify the bioluminescence imaging datasets as described before (Markley et al., Blood, 2010. 115(17): 3508-19). Mice were cared for in accordance with the institutional guidelines of Memorial Sloan-Kettering Cancer Center (MSKCC).

Statistical Methods

Data are presented as the mean±standard deviation/standard error of the mean as stated in the txt. Results were analyzed by unpaired Student's t-test (twotailed) or by ANOVA as stated in the text and statistical significance was defined as p<0.05. Pairwise multiple comparisons were performed using multiple t tests corrected for multiple comparisons with the Holm-Sidak method. All exact P values are provided. All statistical analyses were done on Prism software version 6.0 (GraphPad).

Results 1. iCARs are Well Expressed on the Cell Surface of Primary Human T Cells Without being bound to a particular theory, it was hypothesized that a single-chain variable fragment (scFv) or Fab specific for an antigen fused to the signaling domains of immunoinhibitory receptors (CTLA-4, PD-1, LAG-3, 2B4, or BTLA) via a transmembrane regino would inhibit T-cell function specifically upon antigen recognition. These receptors are termed iCARs, as they have immune cell inhibitory potential, chimeric receptors that bind a specific antigen and are distinct from CARs, a term used to describe receptors with immune cell activating potential.

An scFv specific for human prostate-specific membrane antigen (PSMA) was used as a model surface antigen (31). This scFv has been extensively studied and is being investigated in phase I trials for immunotherapy of prostate cancer (32). PSMA is overexpressed in metastatic prostate cancer but is also found in normal kidney, liver, colon, and brain astrocytes (33). Five different iCARs specific for PSMA (referred to as iCAR-P) were generated having CTLA-4, PD-1, LAG-3, 2B4, and BTLA intracellular domains, respectively. A control receptor, Pdel, was generated which possessed only the targeting scFv and a transmembrane domain but lacking a cytoplasmic domain (FIG.

Figure 1B:
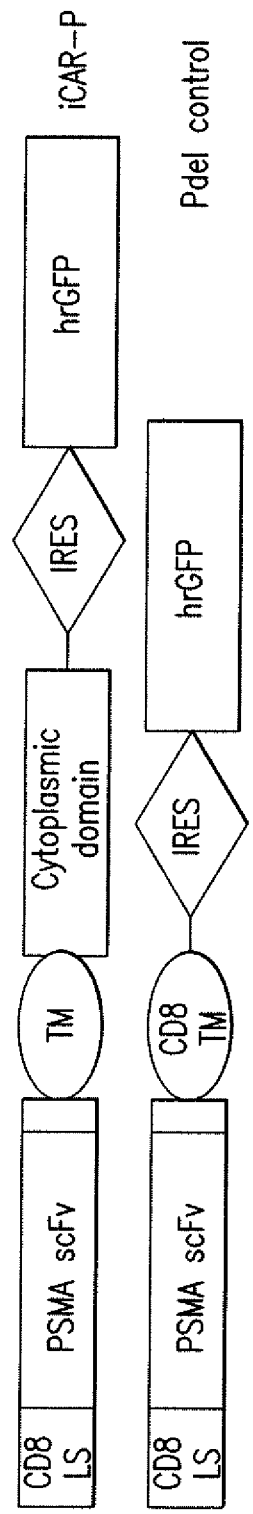
Figure 1C:
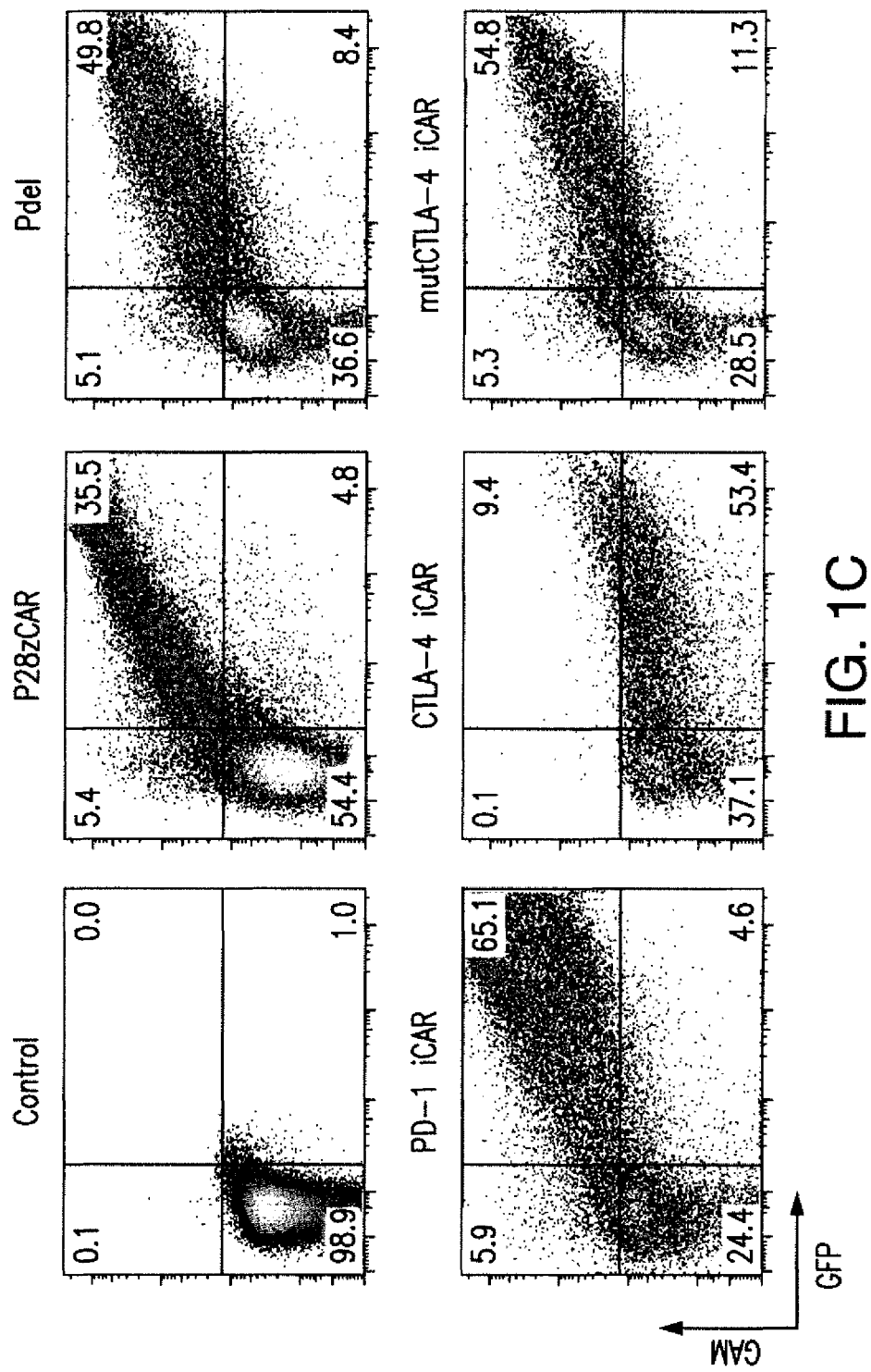
Figure 1D:
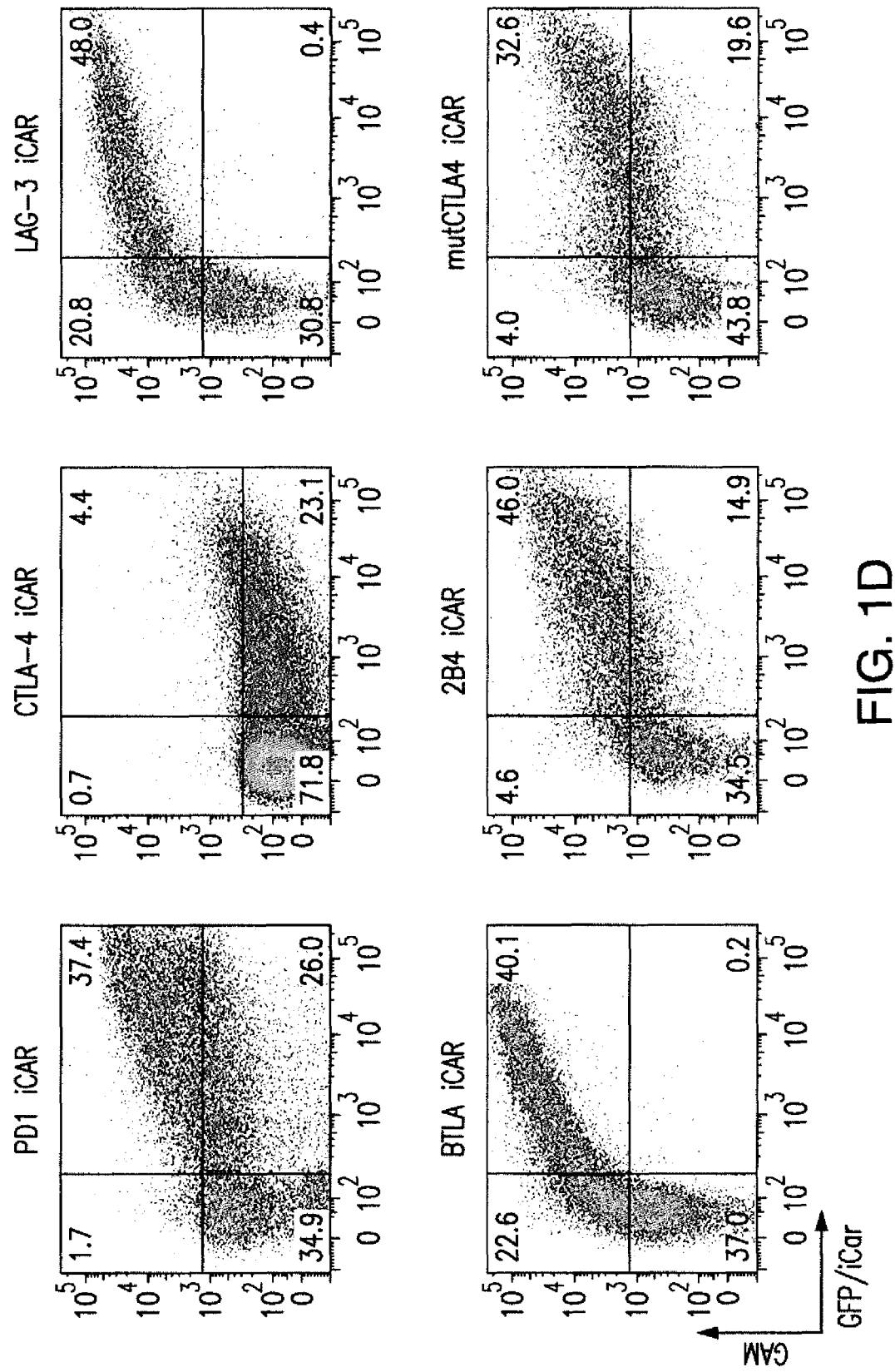

(1B). Each iCAR was cloned into a bicistronic retroviral vector with an IRES-GFP reporter module (FIG. 1B). Upon transduction of human primary T cells from peripheral blood mononuclear cells, the CTLA4-iCAR were well expressed on the cell surface, and the PD-1-iCAR-P and Pdel were expressed on the cell surface at similar levels to the P28z receptor (34), a CD28/CD3ζ-based, dual-signaling PSMAspecific receptor that is currently used in a clinical trial (FIGS. 1C and 1D). Phospho-arrays were used to investigate if the PD1-iCAR was transducing a signal upon receptor engagement. The state of phosphorylation was analyzed using the RnD human Phospho-Immunoreceptor array upon exposure to 3t3-D vs 3T3-S targets. 1928z-P-PD1 cells were incubated with either 3T3 WT, 3T3-S, or 3T3-D cells. Two hours were allowed for receptor engagement, and then cell lysates for the phospho-state were analyzed. Cells exposed to 3T3-D had significant increases in the phosphorylation of SHP-1, SHP-2, as well as 2B4 all downstream targets of PD1 signaling, importantly in the case of exposure 3t3-S all three showed a decrease in signal strength (FIG. 18). In the case of the CTLA4-iCAR, robust intracellular expression was observed by Western blot and intracellular flow cytometry, but limited cell surface expression (FIGS. 1C, 1D and 9A-C). Surface expression was restored using a Y165G mutant CTLA4-tail, a key residue for cell surface trafficking, to construct a mutCTLA4-iCAR (FIGS. 1C, 1D and 9A-C). This finding is consistent with the physiological trafficking of CTLA-4, which is constitutively internalized in resting T cells and degraded through interaction with the endocytic adaptor complex AP-2 via its tyrosine motif YVKM (35). Indeed, upregulation of the CTLA-4-iCAR-P to the cell surface after T cell activation was found (FIG. 9C), and restored constitutive surface expression using a tyrosinemotif Y165G mutant to construct mutCTLA-4-iCAR-P, which exhibited cell surface expression in resting cells (FIG. 1C). PSMA recognition by iCARs was demonstrated using a cellular conjugation assay in which iCARexpressing T cells bound mouse thymoma EL4 cells expressing PSMA (FIG. 10A).

2. iCARs Limit TCR Responses in an Antigen-Restricted Manner

Figure 11D:
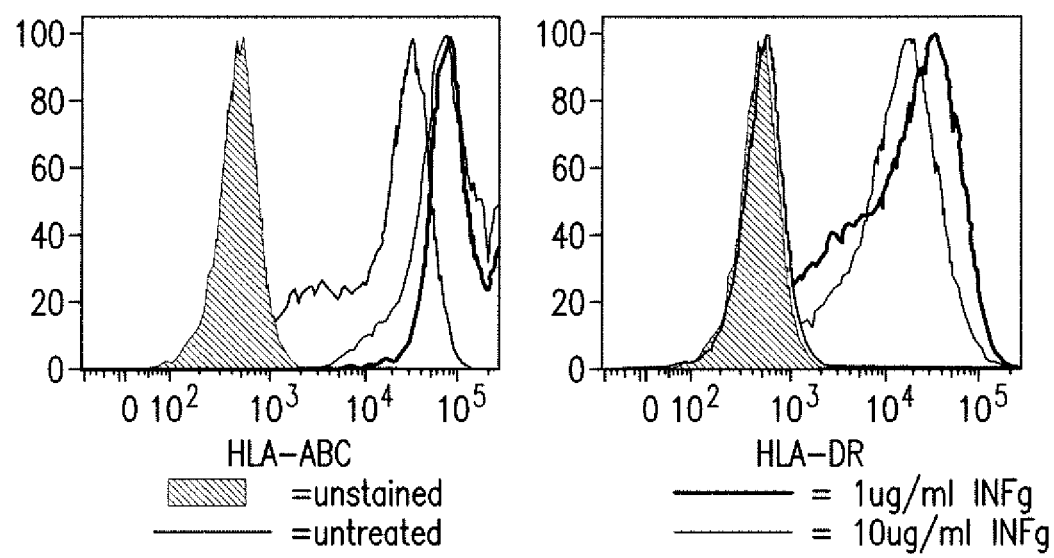

In addition to their use on autologously targeted T cells, iCARs have potential utility for the prevention of GVHD in post-transplantation donor lymphocyte infusion. Therefore, the efficacy of iCARs was assessed in protecting a non-transformed surrogate normal tissue in the context of alloreactivity, a powerful immune response that underlies graft rejection, GVHD and therapeutic graft-versus-tumor (GVT) responses. In addition, to study the effect of iCARs on endogenous TCR-driven primary human T cell responses, an alloreactivity model (FIG. 11A) using allogeneic dendritic cells (DCs) as priming antigen-presenting cells and fibroblasts isogenic to the DCs as the targets was established (FIG. 11A). In this model, the iCAR- or Pdel-engineered T cells were primed with monocyte-derived dendritic cells (moDCs), which is an extremely potent stimulator of the endogenous T-cell receptor (TCR), and then evaluated against fibroblasts expressing the PSMA antigen or not. To obtain replenishable fibroblasts isogenic to the DCs without requiring iterative skin biopsies, induced pluripotent stem cells (iPSCs) were established, stable fibroblast cell lines, termed iPS-fib were derived from iPSCs (FIGS. 11B-D). The iPS-fib displayed replicative senescence and contact inhibition, and could be easily transduced, passaged, and implanted in NOD/severe combined immunodeficient (SCID)/$\gamma_c^-$ mice wherein they persisted for weeks without forming tumors. To acquire potent alloreactive T cells with endogenous TCR specificity against the iPS-fib, moDCs with lysates from the isogenic iPS-fib were pulsed. This priming culture system stimulated robust cytotoxicity and cytokine secretion from several T cell donors, producing both CD4- and CD8-driven responses (FIGS. 12A-C).

Figure 2A:
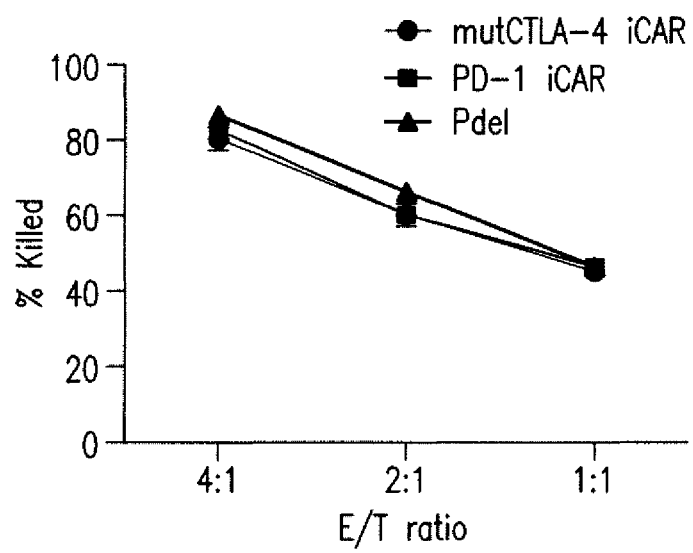
Figure 2B:
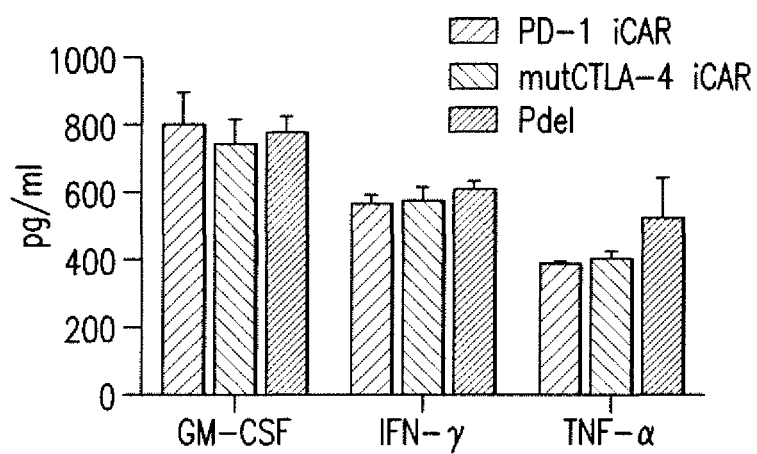
Figure 2D:
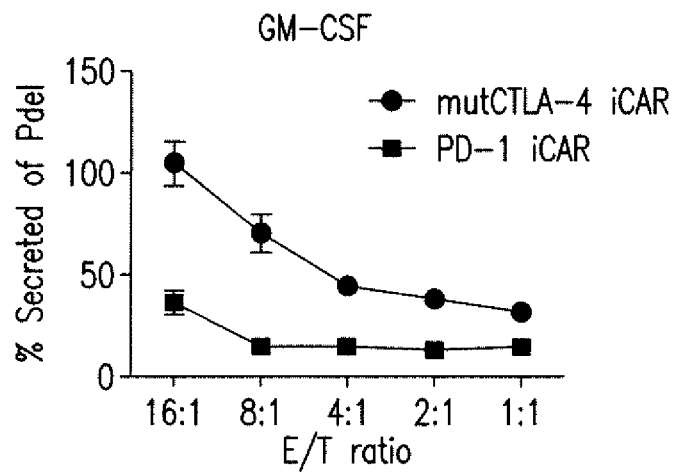
Figure 2E:
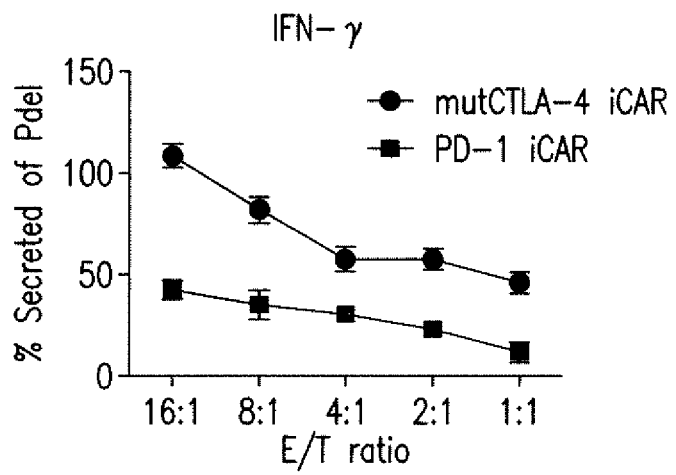
Figure 2F:
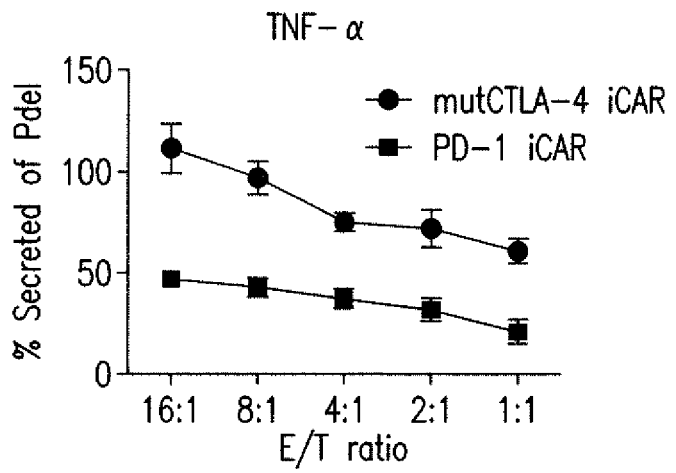

To investigate the ability of the iCARs to restrict alloreactivity against PSMA$^+$ cells, iCAR- or Pdel-expressing T cells primed with two rounds of pulsed moDCs were sorted and then were co-incubated with iPS-fib or iPS-fib expressing PSMA (FIG. 13A) (36). All groups of T cells efficiently killed iPS-fib, demonstrating allogeneic cytotoxicity (FIGS. 2A and 2B), but the iCAR-positive T cells were significantly inhibited in their ability to kill iPS-fib-PSMA$^+$ cells (FIG. 2C). Cytotoxicity by T cells expressing the PD-1-based iCAR was reduced by up to 95% at low effectorto-target (E/T) ratios. Because cytotoxicity occurs rapidly and has a low activation threshold relative to other T cell responses, cytokine secretion were also analyzed. The PD-1 iCAR produced the stronger inhibition of cytokine secretion (79 to 88% reduction), whereas the mutCTLA-4 iCAR elicited 55 to 71% reduction (FIG. 2D-F). These results suggested that iCARs could limit reactivity in an antigen-dependent manner.

3. iCARs Function in a Stoichiometric Manner

Figure 3A:
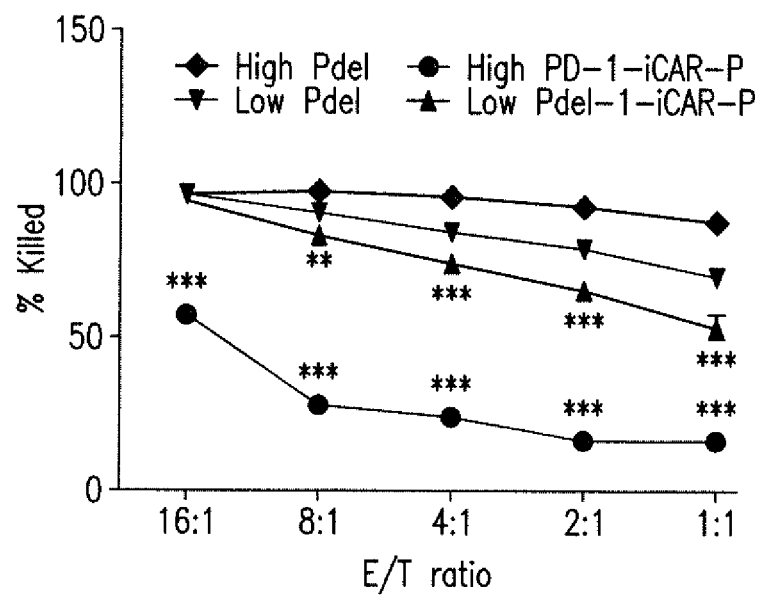
FIGS. 3A to 3D show that iCARs functioned in a stoichiometric manner. (A) Pdel- or PD-1 iCAR-P-transduced alloreactive T cells were sorted for high or low expression of each respective receptor, as shown in FIG. 13A, and were seeded on iPS-fib-PSMA-expressing CBL. Killing of iPS-fib-PSMA relative to untreated cells was assessed with the Bright-Glo assay system (n=3 for each condition). (B) Cytokine secretion, measured at 24 hours in the cell culture supernatant from (A) at 4:1 E/T ratio. (C) PD-1 iCAR-P-transduced alloreactive T cells were incubated with iPS-fib-PSMA sorted for high or low levels of PSMA expression as shown in FIG. 13B. Killing of each population relative to untreated cells was quantified with the Bright-Glo assay system (n=3 per condition). D) Cytokines from (C) were assessed at 24 hours. Error bars represent ±SEM. ***P<0.001 by Student's t test. Error bars represent ±SEM. *P<0.01, ***P<0.001 by ANOVA comparing to high Pdel group and post hoc analysis with multiple t tests corrected with the Holm-Sidak method. Raw data and P values are provided in the FIGS. 20A and 20B.
Figure 3B:
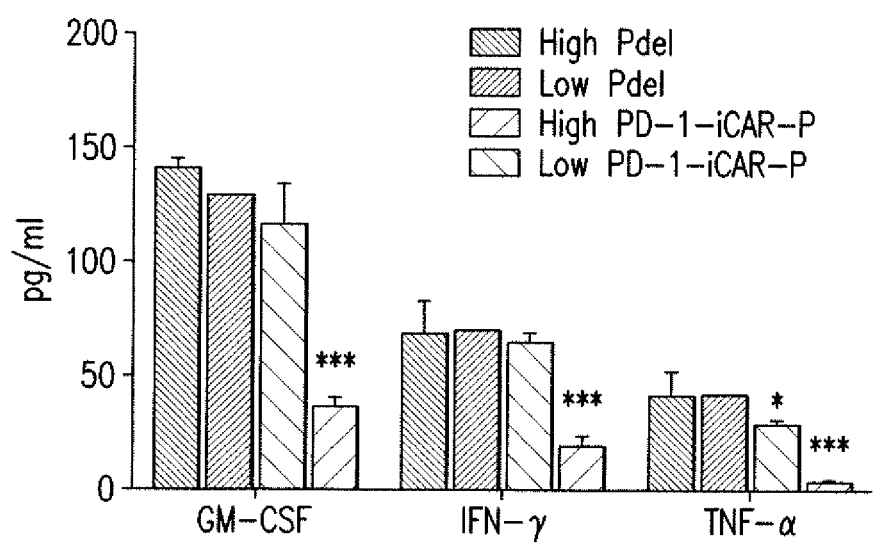
Figure 3C:
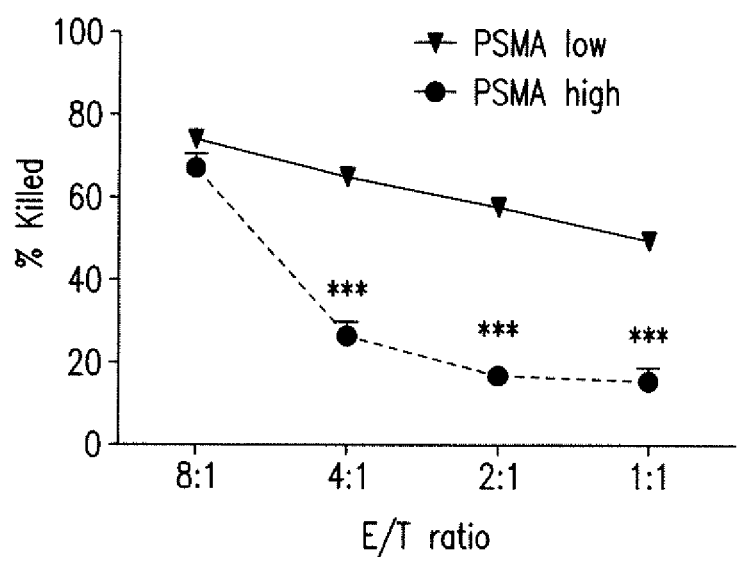
Figure 3D:
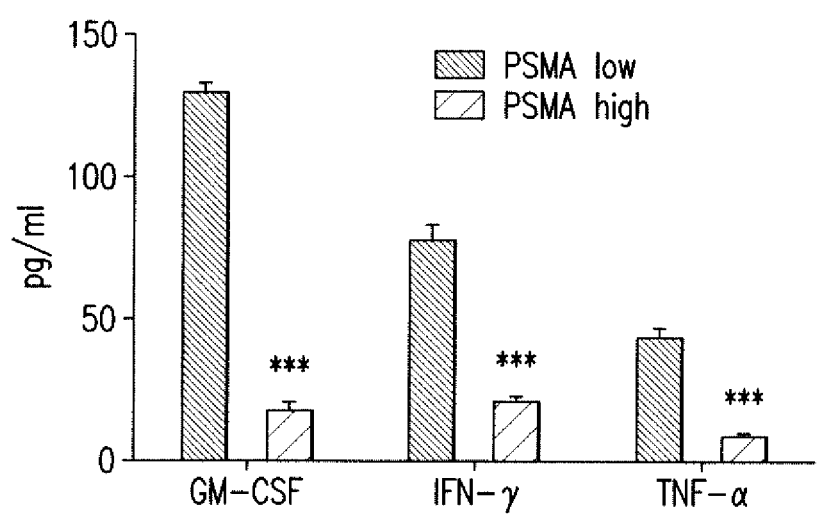

Whether the PD-1 iCAR-P could provide differential levels of inhibition depending on its level of expression or that of the target antigen were investigated. Primed T cells for high or low levels of PD-1 iCAR-P or Pdel expression were sorted and were exposed to iPS-fib-PSMA (FIG. 14A). A stoichiometric relationship between T cell killing, cytokine release, and the level of iCAR expressed was found. T cells sorted for low levels of expression of the PD-1 iCAR-P could provide 50% inhibition only up to E/T ratios of 1:1, but high levels of PD-1 iCAR-P expression allowed 80% inhibition up to E/T ratios of 8:1 and even 50% inhibition at 16:1 (FIGS. 3A and 3B). To examine the impact of the iCAR antigen expression level, iPS-fib for high or low PSMA expression were sorted and were exposed to sorted PD-1 iCAR-P T cells (FIG. 14B). iPS-fib with high PSMA expression inhibited at least 80% of the killing and cytokine secretion of PD-1 iCAR-P T cells across a range of E/T ratios (1:1 to 4:1), whereas iPS-fib with low PSMA expression failed to provide the same level inhibition (FIGS. 3C and 3D).

4. iCARs Limit Allogeneic Responses In Vivo

To investigate whether an iCAR could protect a tissue from T cell-mediated elimination in vivo, iPS-fib-PSMA$^+$ cells (which also expressed CBL) were injected intraperitoneally into NOD/SOD/γc$^-$ mice (FIG. 14B). The cells established nodules that could bemonitored by bioluminescence imaging (BLI). Five days after injection of 1×10$^6$ iPS-fib-PSMA$^+$ cells, the mice were treated with 5×10$^5$ moDC-primed Pdel- or PD-1-iCAR-P-expressing T cells. The Pdel group eliminated the iPS-fib-PSMA$^+$ cells with a significant decrease in the BLI signal (7- to 22-fold), whereas the PD-1-iCAR-P group was unable to clear the nodules with BLI similar to control mice not treated with T cells (FIGS. 4A and 4B). These results provide evidence that an iCAR can limit a TCR-driven response in an antigen-specific fashion in vivo.

5. iCARs can Inhibit Activating Chimeric Antigen Receptors

Figure 15A:
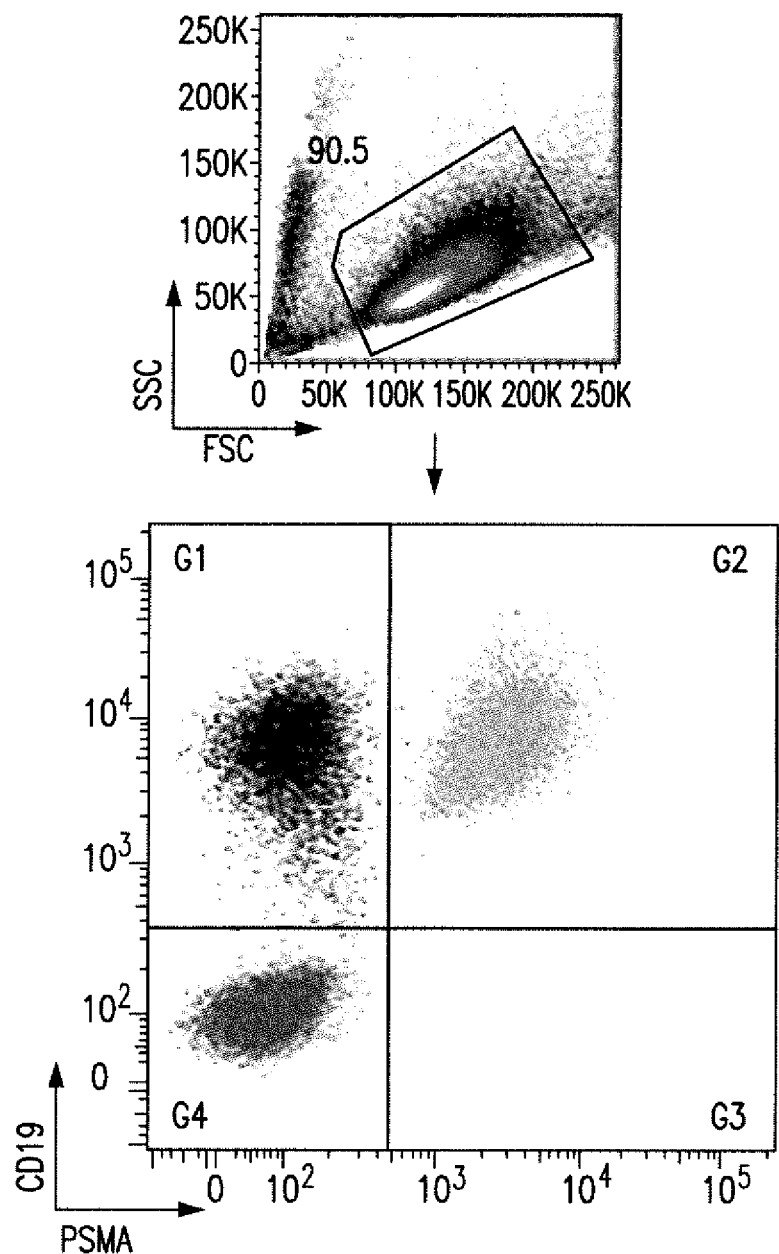
Figure 15B:
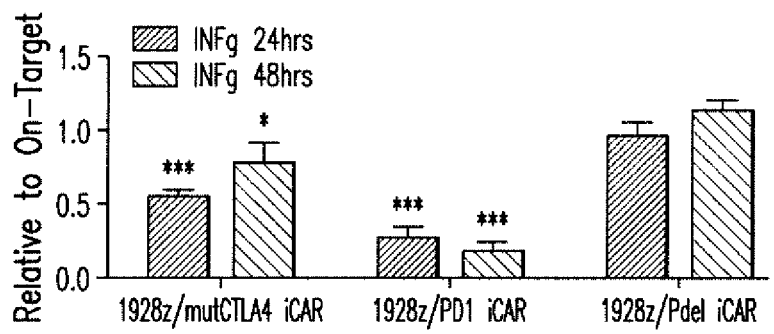

To study the effect of iCARs on modulating activating CARs, 19-28z, an extensively characterized second-generation CAR currently used in clinical trials, was used; 19-28z provides activation and CD28 costimulation in response to the CD19 antigen (9, 34). Primary T cells were transduced with 19-28z CAR and the iCAR-P receptors, sorted for dual expression, and seeded on previously reported artificial antigenpresenting cells (AAPCs) expressing CD19 or both CD19 and PSMA, respectively, modeling target and off-target tissues (FIGS. 13B and 15A). The 19-28z chimeric antigen receptor (CAR), an extensively characterized second-generation CAR currently in clinical trials, was utilized to provide activation and costimulation signals in response to the CD19 antigen (Brentjens et al., Blood, 2011. 118(18): 4817-28; Maher et al., Nature Biotechnology, 2002. 20(1): 70-75). Although the T cells from the control groups (19-28z alone or 19-28z/Pdel) showed similar cytokine secretion on both AAPCs, the iCAR-expressing T cells showed a marked decrease in cytokine secretion when exposed to off-target cells relative to on-target cells (FIGS. 5A and 5B). PD-1 iCAR-P produced the strongest reduction of cytokine levels (71 to 89%), whereas mutCTLA-4 iCAR-P elicited a lesser reduction (48 to 67%), and LAG-3-, BTLA-, and 2B4 iCAR-P elicited 30% inhibition.

Figure 5C:
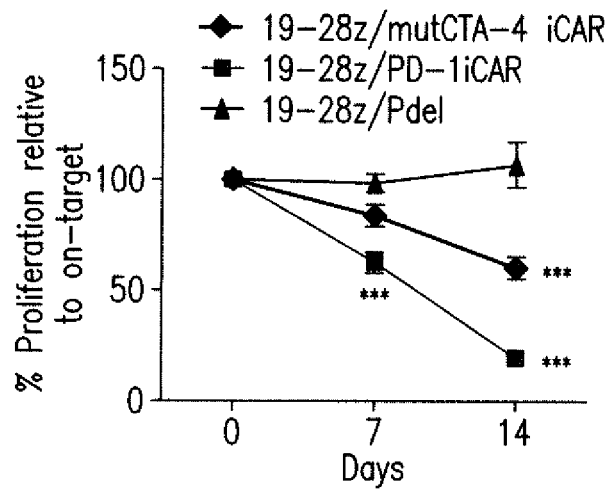
Figure 5D:
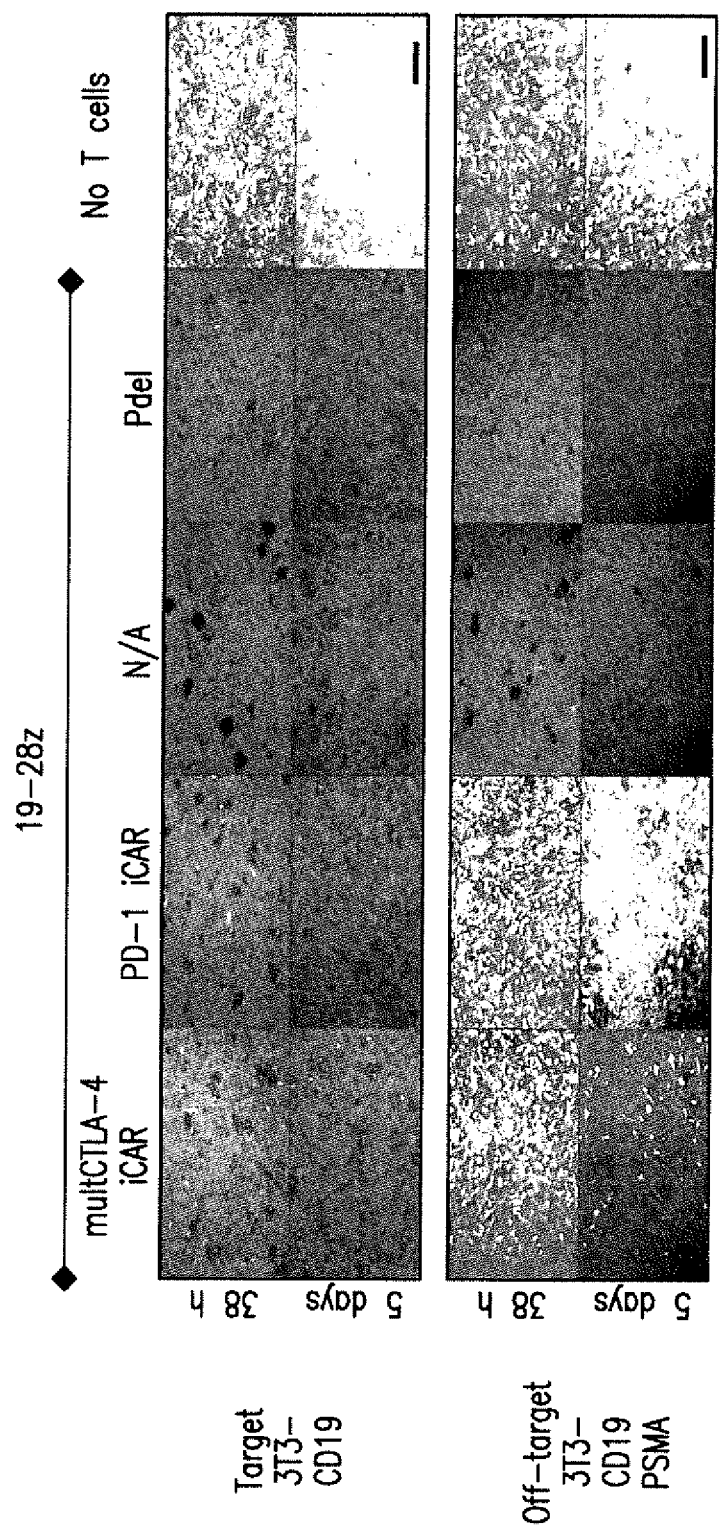
Figure 5E:
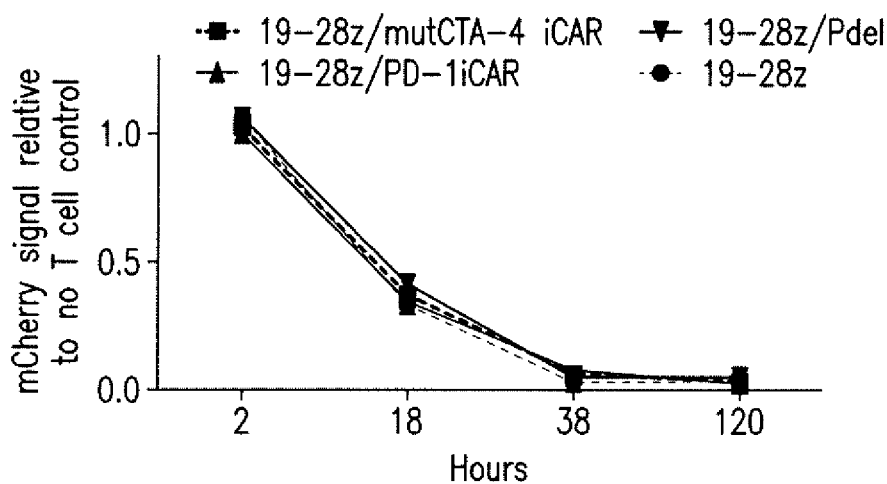
Figure 5F:
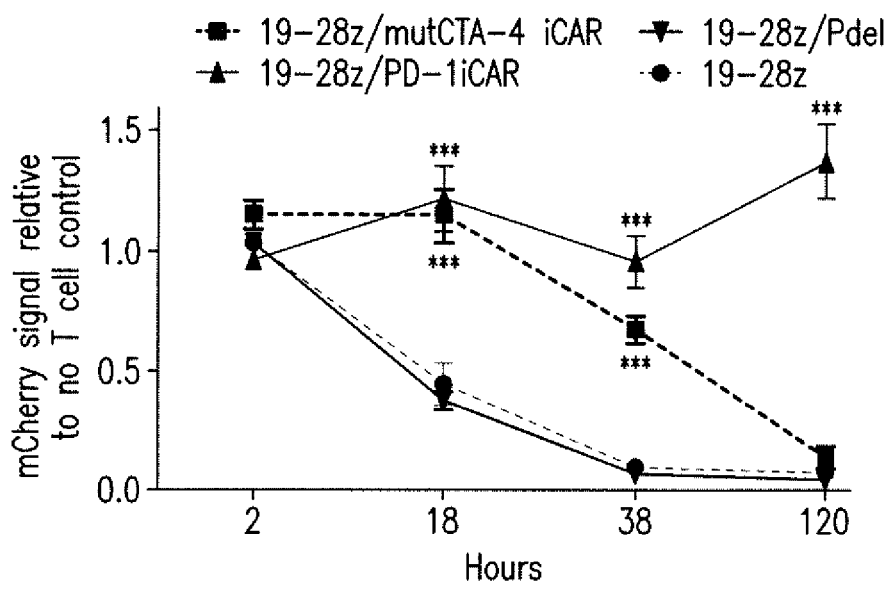
Figure 15C:
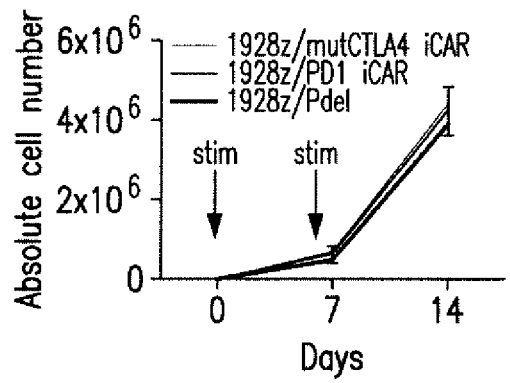

19-28z provides a potent proliferation signal, induced by CD19-expressing AAPCs. Although 19-28z/Pdel T cells expanded similarly on either AAPCs, T cells expressing mutCTLA-4 or PD-1 iCARs showed reduced accumulation in the presence of the off-target AAPCs, with the PD-1 iCAR-P causing a cumulative 90% decrease in T cell accumulation after the second AAPC stimulation (FIGS. 5B, 5C and 15C). As the ability of the iCARs to block T-cell cytokine secretion and proliferation was demonstrated, iCARs were assessed for their effect on cytotoxicity, which occurs rapidly and has a lower activation threshold than other T-cell functions. In this coculture system, quantitative microscopy the fate of these AAPCs, were examined, which was modified to additionally express mCherry (FIG. 5D). Within 38 hours, all groups of 19-28z/iCAR-P and control double-positive T cells lysed the target cells (FIG. 5E). When exposed to CD19$^+$PSMA$^+$ off-target cells, the mutCTLA-4- and PD-1-based iCARs caused a 67 and 91% reduction in cytotoxicity, respectively (FIG. 5F). In the case of PD-1, AAPCs persisted for 5 days, whereas the effect of the mutCTLA-4 iCAR was more limited (FIG. 5D). Therefore, the PD-1-based iCAR was selected for further in vivo evaluation.

Figure 6A:
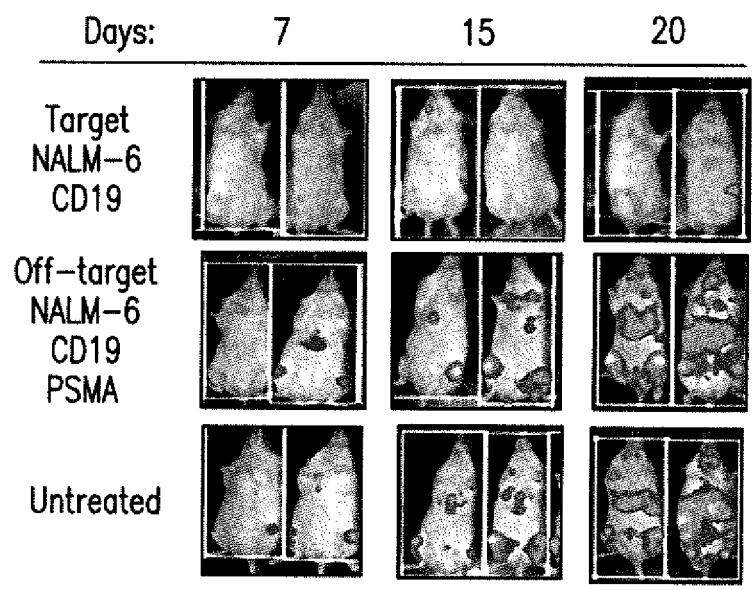
Figure 6B:
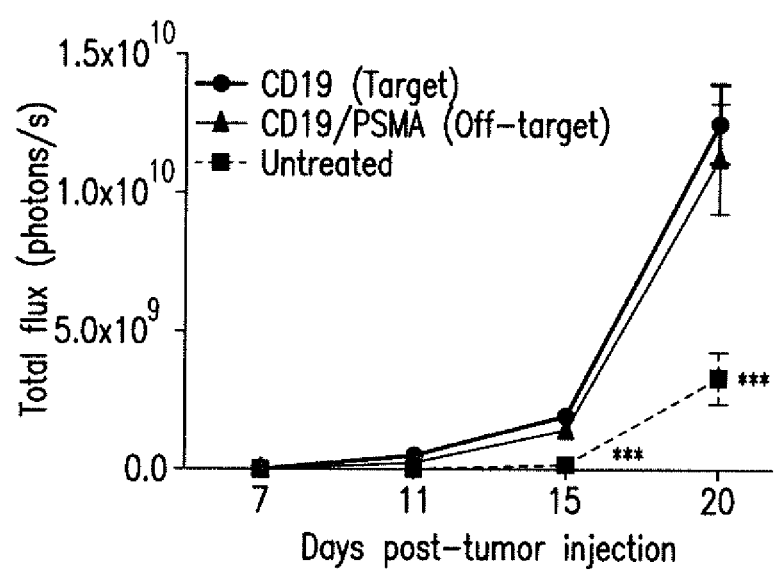
Figure 6C:
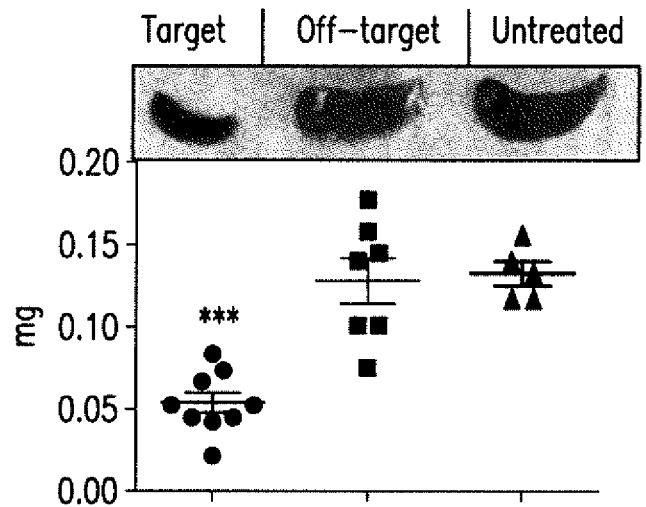
Figure 6D:
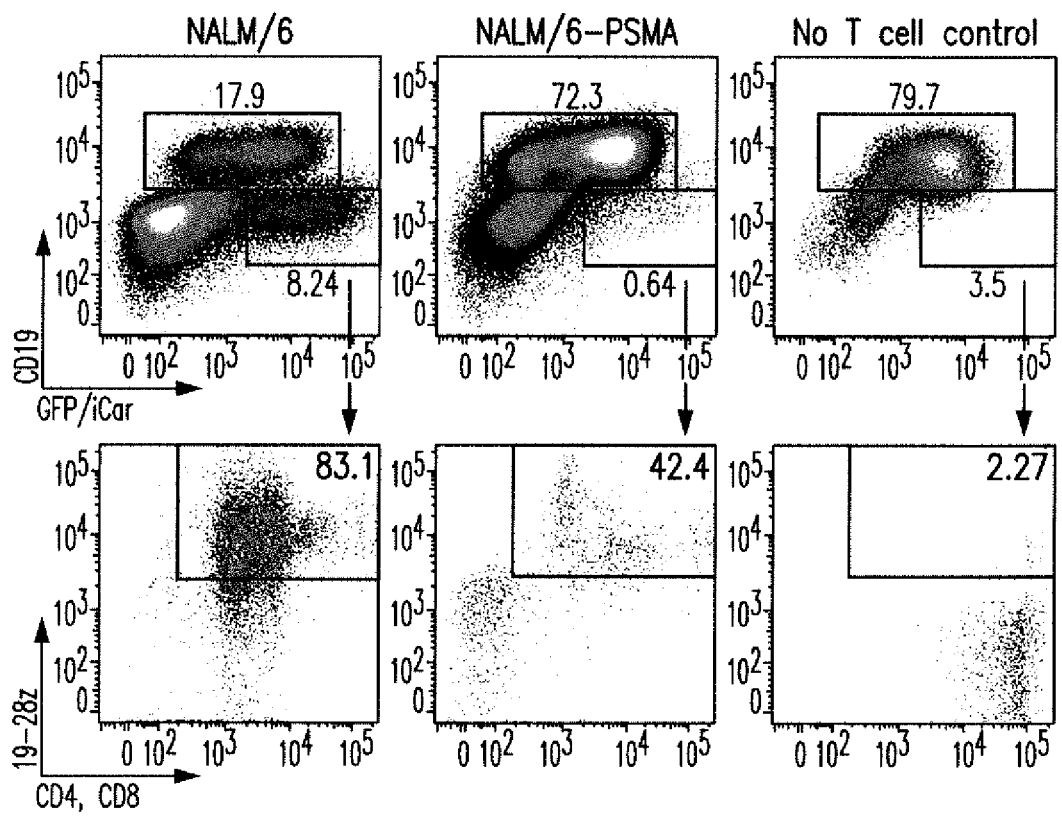
Figure 6E:
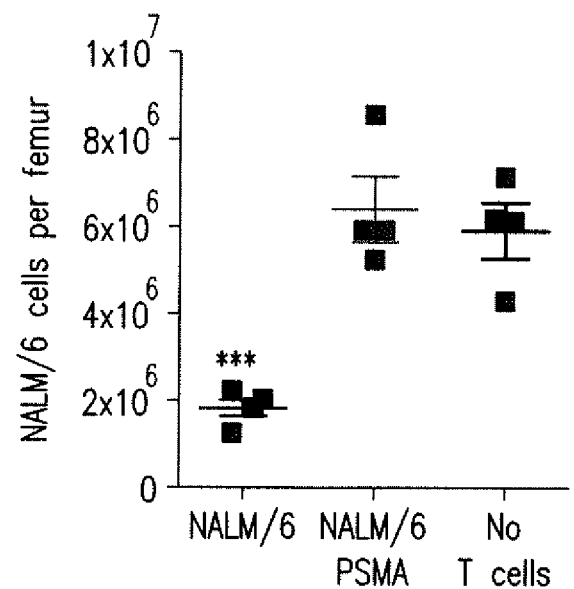
Figure 6F:
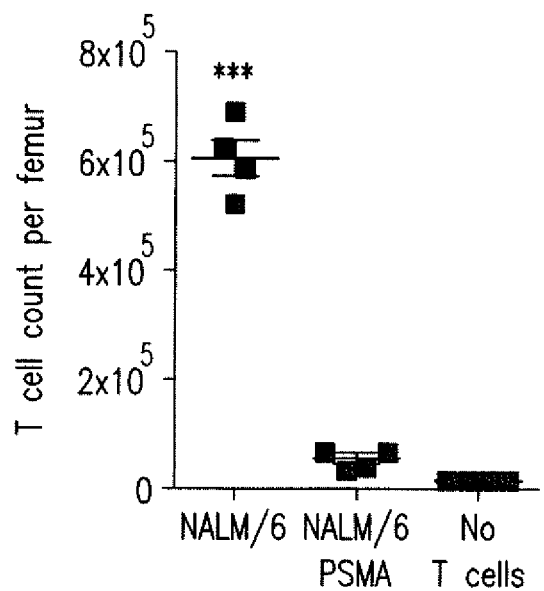
Figure 15D:
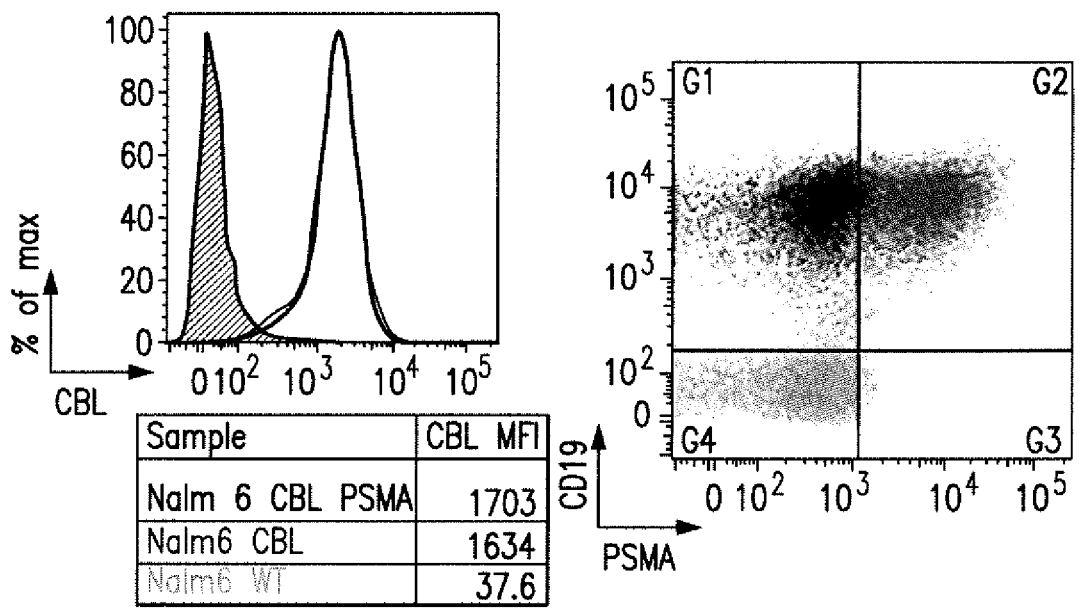

To evaluate the function of the PD-1 iCAR in vivo, NALM/6, a CD19$^+$ B cell leukemia cell line, with PSMA, was evaluated and therapeutic T cell responses were compared against NALM/6 and NALM/6-PSMA cells in a previously established xenograft NOD/SCID/$\gamma_c^-$ mouse model (Markley et al., Blood, 2010. 115(17): 3508-19; Brentjens et al., Clin. Cancer Res., 2007. 13(18:1): 5426-35) (FIG. 15D). Five days after systemic tumor infusion, the mice were treated with a single dose of 3×10$^5$ 19-28z/PD-1-iCARP-sorted double-positive T cells. Bioluminescent imaging (BLI) of tumor burden showed significant differences (3- to 10-fold reduction) in the eradication of NALM/6-PSMA (off-target) as opposed to NALM/6 (on-target) (FIGS. 6A and 6B). Although initially confined to bone marrow, NALM/6 leukemia eventually invades the spleen, the weight of which provides a late-stage index of disease burden. After treatment with 19-28z/PD-1-iCAR-P T cells, NALM/6-PSMA mice showed no significant difference in spleen weight from the control "no T cell" group, but the spleen weights of the mice with NALM/6 were 2.6-fold lower (FIG. 6C). Flow cytometric analyses confirmed the decreased number of NALM/6 cells in the spleen and bone marrow, in contrast to the NALM/6-PSMA group (FIGS. 6D and 6E). In parallel, greater persistence of T cells was found in the NALM/6 group than in the NALM/6-PSMA group (FIGS. 6D and 6F). These findings established that the PD-1-based iCAR selectively prevents the elimination of "off-target" NALM/6-PSMA cells in vivo while allowing the therapeutic response against "on-target" NALM/6 cells to proceed.

6. iCARs Function in a Temporary and Reversible Manner

Figure 7A:
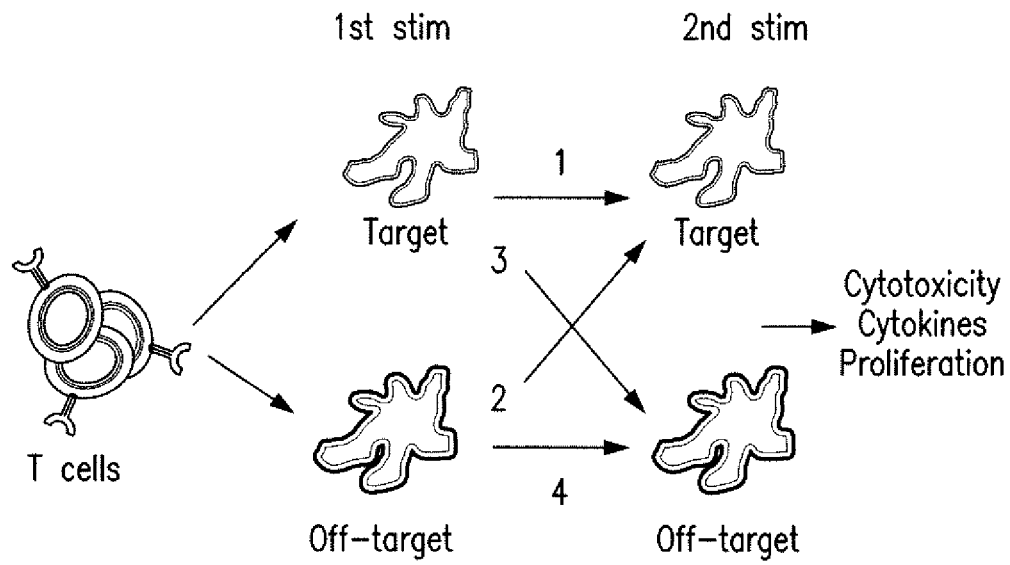
Figure 7B:
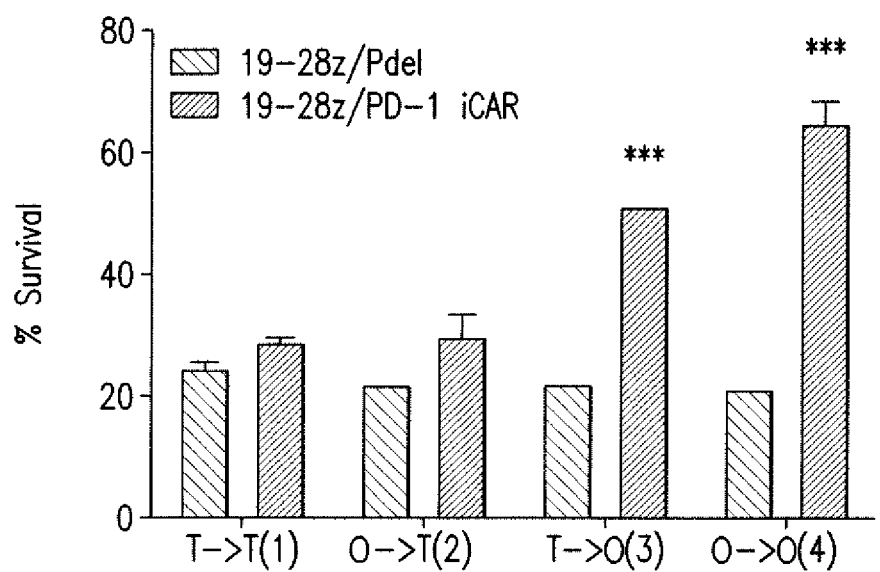
Figure 7C:
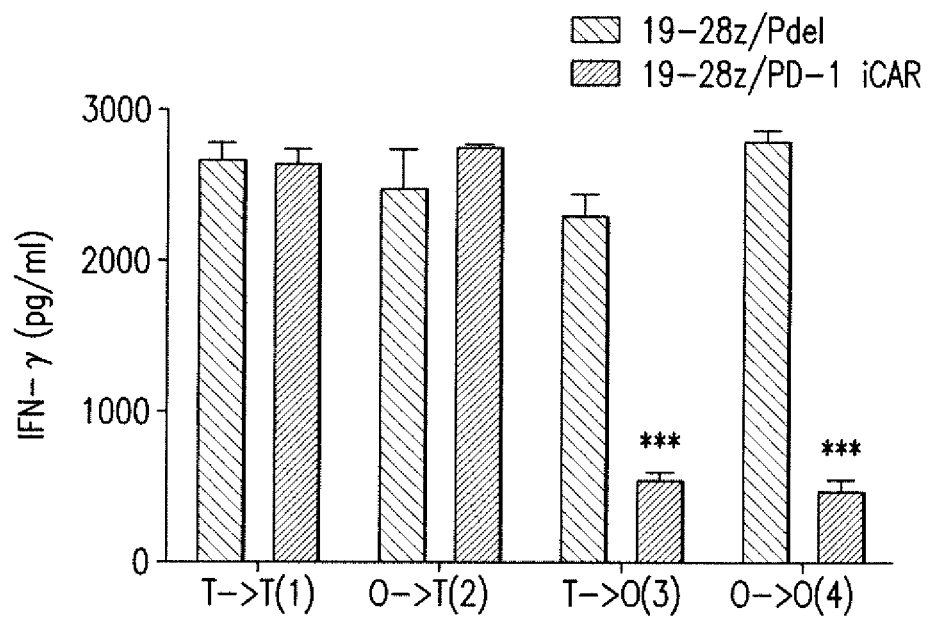
Figure 7D:
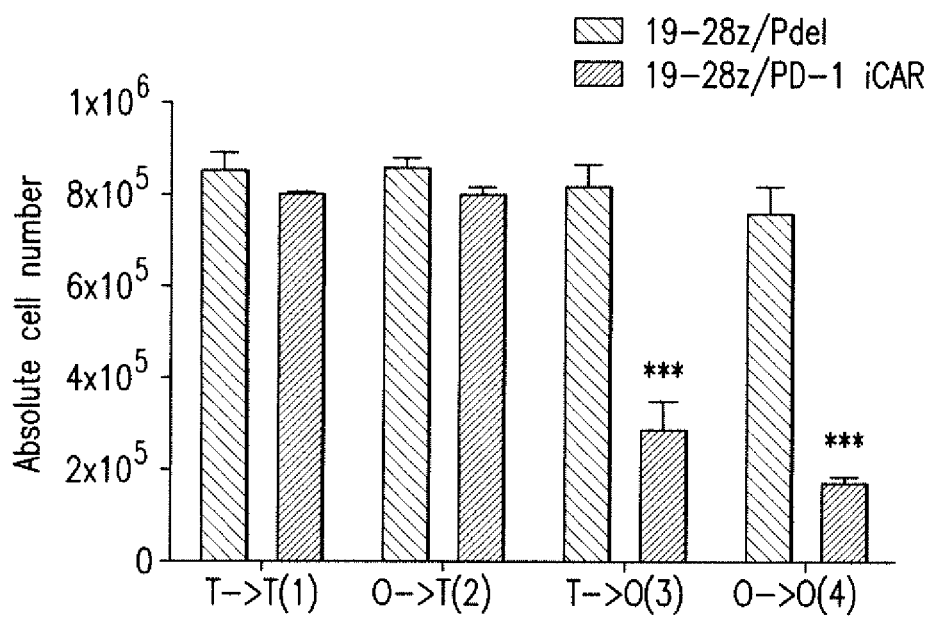
Figure 16F:
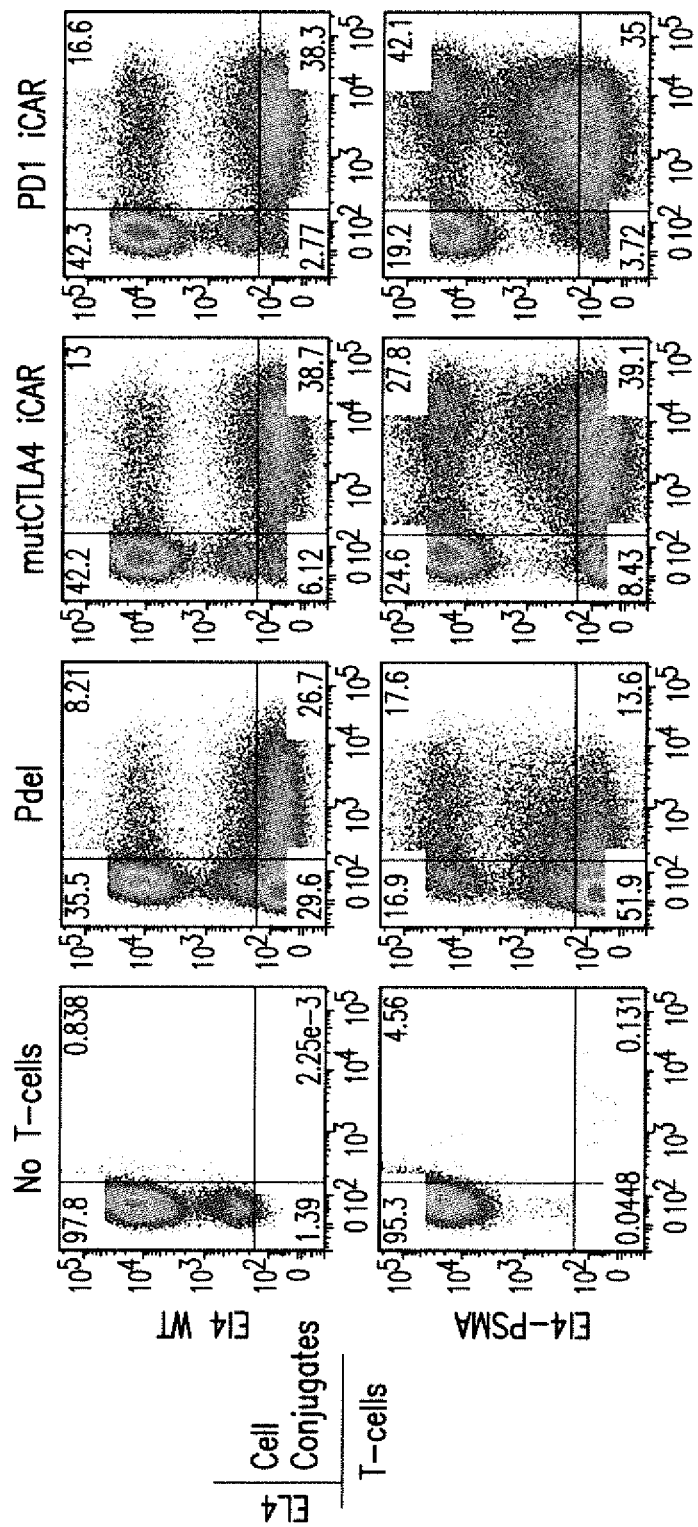
Figure 16G:
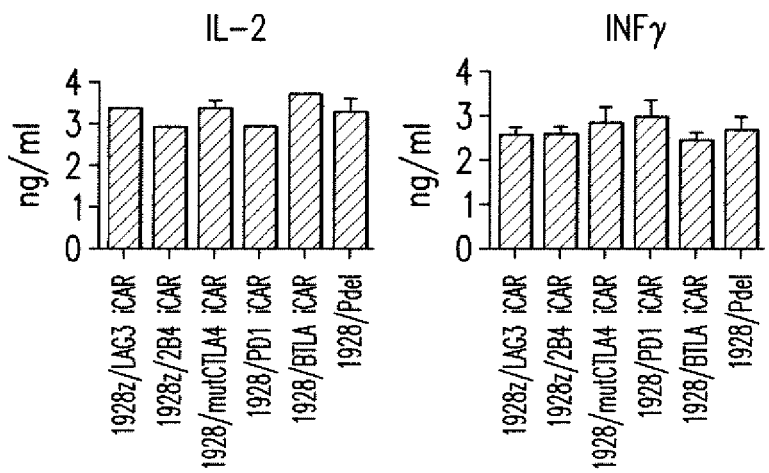
Figure 16H:
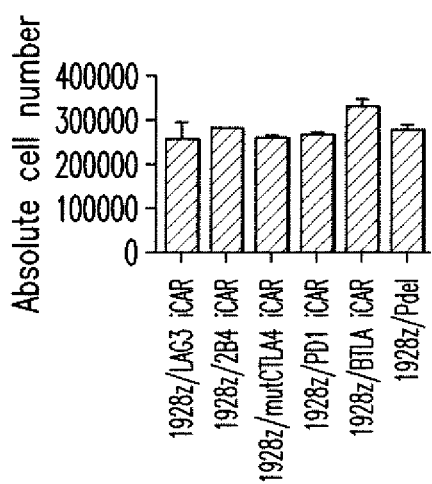
Figure 16I:
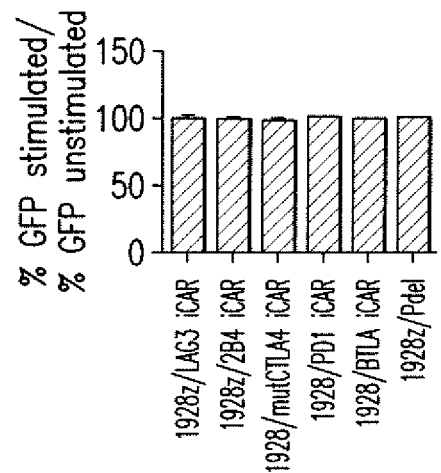

An attractive aspect for the clinical usefulness of iCARs is functional reversibility, that is, the reemergence of T cell functionality after previous contact with an inhibitory off-target tissue. Effective PSMA recognition by iCARs was demonstrated by conjugate formation of iCAR-expressing T-cells with EL4 cells expressing PSMA, but not with wild type EL4 cells (FIG. 16FA). Constitutive expression of the iCARs did not impair the T cells' proliferative capacity (post-CD3/CD28 bead or DC activation), cytokine secretion, or surface marker expression compared to control T cells (FIGS. 16A-E and 16G-I). To assess the temporal features of iCAR-medicated inhibition, sequential T cell stimulation by target and off-target cells were set up to analyze the potential for killing, cytokine secretion, and proliferation in four different sequences. 19-28z/Pdel or 19-28z/PD-1-iCAR-P T cells were exposed to either the target (CD19$^+$) or off-target (CD19$^+$PSMA$^+$) AAPCs as a first stimulation, followed by exposure to either AAPCs in a second stimulation (FIG. 7A). On the second stimulation, both T cell groups killed target cells equally well irrespective of the first stimulation target (FIG. 7B), supporting that the 19-28z/iCAR-P T cells exposed to off-target cells in the first stimulation killed target cells and proliferated during the second stimulation as well as the T cells that were exposed to target cells in both stimulations. Control T cells expressing the 19-28z/Pdel did not show reduced functionality under the same conditions. Additionally, T cells that were activated on the first stimulation could still be inhibited upon exposure to the iCAR ligand presented by the off-target AAPCs on the second stimulation, suggesting that iCARs could regulate an activated T cell. It was also observed that T cells exposed to off-target cells on both stimulations had greater inhibition of their killing capacity on the second exposure (FIGS. 7C and 7D).

Corroborating these functional findings, we found that the PD-1 iCAR, 19-28z/Pdel, and 19-28z/PD-1-iCAR-P double-positive T cells differentially phosphorylated the regulatory SHP-1 and SHP-2 phosphatases (FIGS. 17A-C). Exposure to CD19$^+$ target AAPCs showed lower SHP-1 and SHP-2 phosphorylation levels compared to the basal levels seen after exposure to AAPCs lacking CD19, consistent with previous studies demonstrating dephosphorylation and consequent blockade of the suppressive effects of SHP-1/2 upon T cell activation (39, 40). In contrast, after exposure to off-target AAPCs expressing CD19 and PSMA, SHP-1 and SHP-2 showed increased levels of phosphorylation, supporting that the PD-1 iCAR recruits the same biochemical pathways as the endogenous PD-1 molecule.

7. iCAR and CAR Dual-Expressing T Cells Discern Targets In Vitro and In Vivo

Figure 8A:
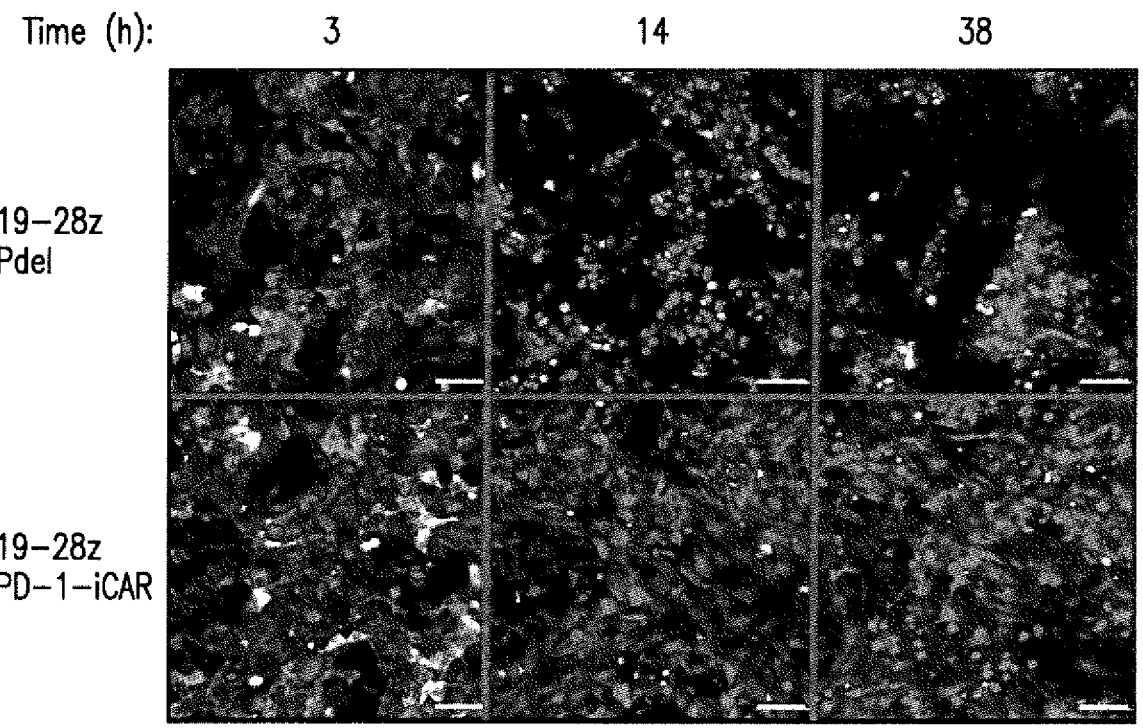
Figure 8B:
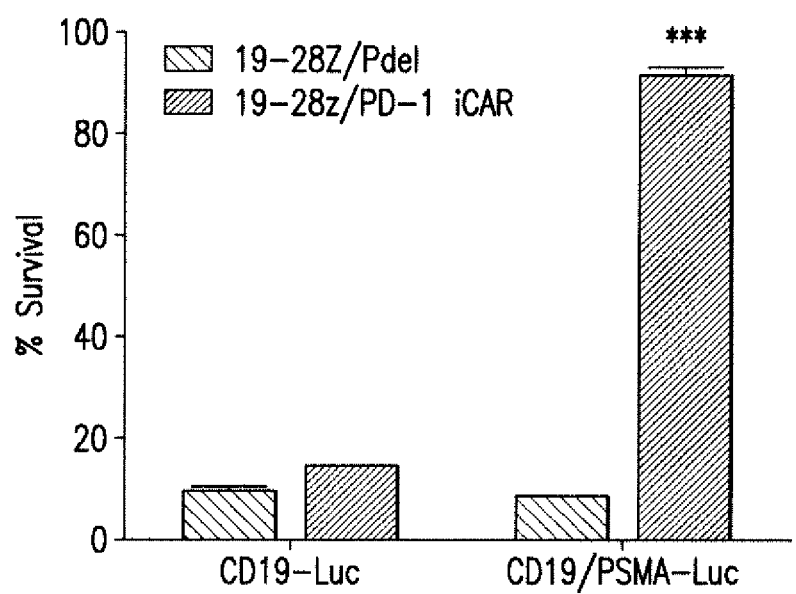

Whether T cells expressing the PD-1-based iCAR could distinguish between target cells in vitro and especially in vivo by protecting off-target cells in the presence of target cells within the same organism were assessed. This scenario was first addressed in an in vitro coculture system mixing GFP$^+$CD19$^+$ target AAPCs and mCherry$^+$CD19$^+$PSMA$^+$ off-target AAPCs at a 1:1 ratio. Time-lapse microscopy was performed to analyze the effect of 19-28z/Pdel or 19-28z/iCAR-P T cells. Both the target and the off-target cells were eliminated at a similar rate by 19-28z/Pdel T cells, but the 19-28z/iCAR-P T cells preferentially eliminated the target cells while sparing the off-target cells (FIG. 8A). Crisscross experiments with Click-beetle luciferase (CBL)-transduced versions of the AAPCs were used to quantify this selectivity. At 38 hours, the 19-28z/iCAR-P T cells eliminated most (85%) of the target AAPCs but few (10%) of the off-target cells, corroborating the results from the time-lapse microscopy (FIG. 8B).

To analyze whether the same selectivity could be attained in vivo, NOD/SCID/$\gamma_c^-$ mice were injected with a mixture of NALM/6 and NALM/6-PSMA tumor cells and these animals were treated with 19-28z- or 19-28z/iCAR-P-transduced T cells. Upon sacrifice, the mice treated with 19-28z T cells showed a three-fold reduction in the number of PSMA+ cells in the spleen and bone marrow compared to mice treated with 19-28z/iCAR-P T cells (FIGS. 8C and 8D). Accordingly, the iCAR treated group had a 3.3-fold increase in spleen weight and overall increased tumor burden (FIG. 8E). These experiments demonstrate that, in the presence of a mixture of target and off-target cells, an iCAR can selectively protect off-target cells without abrogating rejection of target cells, both in vivo and in vitro.

Discussion

In this Example, a genetic approach was taken to restrict the specificity of T cells and it was demonstrated that T cells can be engineered to have an endogenous regulatory targeting mechanism to deliver tumor-specific immunotherapy. An antigen recognition domain was successfully combined with the signaling domains of immune inhibitory receptors CTLA-4 and PD-1 to achieve antigen-specific suppression of T cell cytotoxicity, cytokine release, and proliferation. This proof-of-concept study demonstrates the potential for iCARs as a strategy to limit T cell function at off-target sites and thus divert immune responses away from unintended target tissues.

The crux of the iCAR strategy relies on three critical properties. The first is that basal expression of the iCAR does not inhibit T cell function in the absence of antigen. Endogenous CTLA-4 or PD-1 signaling requires the presence of the respective ligands to exert their effect. Likewise, expression of the iCARs described herein was not found to affect basal T cell functions. Other inhibitory receptors that are restricted to T cell subsets may act in concert to fine-tune the regulation of T cell responses (21, 22). Receptors such as LAG-3, 2B4, and BTLA and their combination (for example, as a single second generation iCAR with multiple combined cytoplasmic domains) warrant further investigation.

The second key property is the maintenance of T cell functionality despite previous engagement of the iCAR. It was found that iCAR-transduced T cells could still mount a response against a target antigen after a previous exposure to an inhibitory antigen. This reversibility is reminiscent of natural killer cell behavior, in which the phosphorylation state of signaling molecules rather than transcriptional changes control rapid functional responses, such as cytotoxicity (41). Anti-PD-1 and anti-CTLA-4 antibodies are able to reverse the impaired function of anergized or exhausted T cells, again arguing for the ability to temporally regulate T cell responses (22). Additionally, biochemical analyses of PD-1 and CTLA-4 effects on the TCR complex depend on phosphorylation states, downstream kinases, and motility rather than apoptosis (40, 42-44). Although both in vitro and in vivo results demonstrate inhibition in response to off-target cells with sustained therapeutic functionality, there is still the possibility that some of the cells may be anergized over time (42). Ultimately, a T cell infusion is stochastic, with some T cells promptly encountering their target and eliminating it, whereas other T cells will first encounter the inhibitory cells. It is conceivable that T cells that repeatedly encounter off-target cells will not expand—a satisfactory outcome for the iCAR strategy, which aims to allow for therapeutic responses to proceed while diminishing the immune attack against normal tissues. The overall expansion of the infused T cell population will integrate these different paths occurring at the clonal level, with some T cells undergoing expansion while others are suppressed, possibly resulting in the disappearance of all infused T cells over time. Under the experimental conditions, enough T cells persisted over 3 weeks to eliminate the targeted tumor. Under such a circumstance, a second or third T cell infusion could be infused if needed, which may be clinically advantageous as discussed elsewhere (9). The eventual induction of anergy and clonal elimination as a means to protect off-target tissues while allowing tumor elimination to proceed should be contrasted to suicide gene strategies where adverse reactivity must manifest itself before T cell elimination is triggered, which results in terminating therapeutic responses as well.

The iCAR mediated immune response is useful for control of Graft Versus Host Disease post donor lymphocyte infusion for the treatment of cancer and chronic infections (specifically allowing for the beneficial properties of DLI with limited toxicities). Additionally, iCARs are useful for control of on target-off tissue toxicity from engineered adoptive T-cells for the treatment of cancer and chronic infections. This raises the possibility of reviving promising therapeutics, which have unacceptable toxicity profiles such as unintended cardiac or lung recognition following adoptive T cell therapy). Thus, iCARs provide a novel strategy to establish safe and efficacious T-cell therapies in both autologous and allogeneic settings.

Third, the iCAR approach is antigen-specific and thus requires the ability to identify tissue-specific target antigens that are absent or down-regulated on the tumor but expressed by the off-target tissues. This question has not been as broadly investigated as the search for tumor antigens, although efforts, such as the Protein Atlas database, are under way to characterize the "surfaceome" of all human tissues (45). One strategy is to use broad classes of surface antigens that are down-regulated on tumor cells. One example is represented by human leukocyte antigen (HLA) molecules, which are found in virtually all cell types, but are down-regulated on tumors as a mechanism of tumor escape from T cell immune responses (46). Thus, allogeneic T cells expressing an iCAR against a host HLA molecule that is down-regulated on the tumor may selectively promote the GVT effect. The iCAR approach may be of particular interest in the setting of DLI as a means to protect GVHD target tissues without impairing GVT responses. Another class of antigens amiable to a similar strategy includes cell surface tumor suppressor antigens, such as OPCML, HYAL2, DCC, and SMAR1 (47-49). OPCML-v1, for example, is widely expressed in all normal adult and fetal tissues but is down-regulated in lymphomas and breast and prostate cancer. Cell surface carbohydrates, lipids, and post-translational modifications, such as mucin-type O-glycans (core 3 O-glycans) have also been found to be down-regulated by tumors (50). Another candidate target is E-cadherin, which is highly expressed in normal skin, liver, and gut—the primary targets of GVHD (51)—but down-regulated by tumor cells undergoing an epithelial to mesenchymal transition, indicating tumor progression and metastasis (52).

A major limitation of this study is the lack of availability of a robust clinically relevant human "normal tissue" model, especially one that allows utilization of human cells, human antigens, and human TCRs, CARs, and iCARs. It was attempted to bridge this gap by establishing iPS cells combined with DCs from the same donor to derive an alloreactivity reaction using human T cells, human target antigens, and human iCARs. Simply co-incubating HLA mismatched allogeneic T cells with iPS or iPS-fib cells did not produce alloreactivity. The use of isogenic DCs was critical to generating potent alloreactivity. the nature of this alloreactivity was not defined, and it is thus possible that the responses that were blocked have no bearing on the mechanisms involved in GVHD.

It was shown that the level of expression of the iCARs is critical. In settings of high expression level of activating receptor or antigen and/or low expression of iCAR or iCAR-targeted antigen, sufficient blockade could not be achieved. In most of the analyses, the iCAR reduced T cell function but did not abrogate it, rarely exceeding 90% inhibition in any assay. In applying the iCAR strategy in a clinical setting, the functionality of every iCAR will need to be optimized on the basis of receptor affinity, receptor expression level (that is, promoter strength), and selection of suitable target antigens based, in part, on their expression level. These will also need to be balanced against the activating receptor to achieve inhibition at off-target sites. In the case of CAR-targeted therapy, an optimized CAR/iCAR ratio could be achieved through careful vector design.

In conclusion, a proof of concept that antigen-specific inhibitory receptors can successfully redirect T cell proliferation, cytokine secretion, and cytotoxicity upon engagement of specific cell surface antigens, thus diverting T cell toxicity away from one tissue while retaining critical effector function against another expressing the same antigen, was provided. This was shown in responses mediated by either TCRs or CARs. This approach prevents, or at least reduces, damage to unintended target tissues and thus obviates the need to irreversibly eliminate therapeutic T cells after unacceptable toxicity has developed. It is a paradigm-shifting approach that takes advantage of the multifaceted functionality of cells as drugs by using synthetic receptors that guide and educate T cells to only perform beneficial functions. This dynamic safety switch may find useful applications in a range of autologous and allogeneic T cell therapies.

REFERENCES

1. J. N. Blattman, P. D. Greenberg, Cancer immunotherapy: A treatment for the masses. Science 305, 200-205 (2004).
2. N. P. Restifo, M. E. Dudley, S. A. Rosenberg, Adoptive immunotherapy for cancer: Harnessing the T cell response. Nat. Rev. Immunol. 12, 269-281 (2012).
3. M. Sadelain, R. Brentjens, I. Rivière, The promise and potential pitfalls of chimeric antigen receptors. Curr. Opin. Immunol. 21, 215-223 (2009).
4. C. J. Turtle, M. Hudecek, M. C. Jensen, S. R. Riddell, Engineered T cells for anti-cancer therapy. Curr. Opin. Immunol. 24, 633-639 (2012).
5. B. R. Blazar, W. J. Murphy, M. Abedi, Advances in graft-versus-host disease biology and therapy. Nat. Rev. Immunol. 12, 443-458 (2012).
6. T. M. Brusko, A. L. Putnam, J. A. Bluestone, Human regulatory T cells: Role in autoimmune disease and therapeutic opportunities. Immunol. Rev. 223, 371-390 (2008).
7. M. Kalos, B. L. Levine, D. L. Porter, S. Katz, S. A. Grupp, A. Bagg, C. H. June, T cells with chimeric antigen receptors have potent antitumor effects and can establish memory in patients with advanced leukemia. Sci. Transl. Med. 3, 95ra73 (2011).
8. R. J. Brentjens, I. Rivière, J. H. Park, M. L. Davila, X. Wang, J. Stefanski, C. Taylor, R. Yeh, S. Bartido, O. Borquez-Ojeda, M. Olszewska, Y. Bernal, H. Pegram, M. Przybylowski, D. Hollyman, Y. Usachenko, D. Pirraglia, J. Nosey, E. Santos, E. Halton, P. Maslak, D. Scheinberg, J. Jurcic, M. Heaney, G. Heller, M. Frattini, M. Sadelain, Safety and persistence of adoptively transferred autologous CD19-targeted T cells in patients with relapsed or chemotherapy refractory B-cell leukemias. Blood 118, 4817-4828 (2011).
9. R. J. Brentjens, M. L. Davila, I. Riviere, J. Park, X. Wang, L. G. Cowell, S. Bartido, J. Stefanski, C. Taylor, M. Olszewska, O. Borquez-Ojeda, J. Qu, T. Wasielewska, Q. He, Y. Bernal, I. V. Rijo, C. Hedvat, R. Kobos, K. Curran, P. Steinherz, J. Jurcic, T. Rosenblat, P. Maslak, M. Frattini, M. Sadelain, CD19-targeted T cells rapidly induce molecular remissions in adults with chemotherapy-refractory acute lymphoblastic leukemia. Sci. Transl. Med. 5, 177ra38 (2013).
10. R. A. Morgan, J. C. Yang, M. Kitano, M. E. Dudley, C. M. Laurencot, S. A. Rosenberg, Case report of a serious adverse event following the administration of T cells transduced with a chimeric antigen receptor recognizing ERBB2. Mol. Ther. 18, 843-851 (2010).
11. R. A. Morgan, N. Chinnasamy, D. Abate-Daga, A. Gros, P. F. Robbins, Z. Zheng, M. E. Dudley, S. A. Feldman, J. C. Yang, R. M. Sherry, G. Q. Phan, M. S. Hughes, U. S. Kammula, A. D. Miller, C. J. Hessman, A. A. Stewart, N. P. Restifo, M. M. Quezado, M. Alimchandani, A. Z. Rosenberg, A. Nath, T. Wang, B. Bielekova, S. C. Wuest, N. Akula, F. J. McMahon, S. Wilde, B. Mosetter, D. J. Schendel, C. M. Laurencot, S. A. Rosenberg, Cancer regression and neurological toxicity following anti-MAGE-A3 TCR gene therapy. J. Immunother. 36, 133-151 (2013).
12. B. J. Cameron, A. B. Gerry, J. Dukes, J. V. Harper, V. Kannan, F. C. Bianchi, F. Grand, J. E. Brewer, M. Gupta, G. Plesa, G. Bassi, A. Vuidepot, A. S. Powlesland, A. Legg, K. J. Adams, A. D. Bennett, N. J. Pumphrey, D. D. Williams, G. Binder-Scholl, I. Kulikovskaya, B. L. Levine, J. L. Riley, A. Varela-Rohena, E. A. Stadtmauer, A. P. Rapoport, G. P. Linette, C. H. June, N. J. Hassan, M. Kalos, B. K. Jakobsen, Identification of a Titin-derived HLA-A1-presented peptide as a cross-reactive target for engineered MAGE A3-directed T cells. Sci. Transl. Med. 5, 197ra103 (2013).
13. G. P. Linette, E. A. Stadtmauer, M. V. Maus, A. P. Rapoport, B. L. Levine, L. Emery, L. Litzky, A. Bagg, B. M. Carreno, P. J. Cimino, G. K. Binder-Scholl, D. P. Smethurst, A. B. Gerry, N. J. Pumphrey, A. D. Bennett, J. E. Brewer, J. Dukes, J. Harper, H. K. Tayton-Martin, B. K. Jakobsen, N. J. Hassan, M. Kalos, C. H. June, Cardiovascular toxicity and titin cross-reactivity of affinity-enhanced T cells in myeloma and melanoma. Blood 122, 863-871 (2013).
14. J. L. Ferrara, J. E. Levine, P. Reddy, E. Holler, Graft-versus-host disease. Lancet 373, 1550-1561 (2009).
15. E. Kotsiou, J. K. Davies, New ways to separate graft-versus-host disease and graft-versustumour effects after allogeneic haematopoietic stem cell transplantation. Br. J. Haematol. 160, 133-145 (2013).
16. G. Akpek, S. M. Lee, V. Anders, G. B. Vogelsang, A high-dose pulse steroid regimen for controlling active chronic graft-versus-host disease. Biol. Blood Marrow Transplant. 7, 495-502 (2001).
17. M. T. Lupo-Stanghellini, E. Provasi, A. Bondanza, F. Ciceri, C. Bordignon, C. Bonini, Clinical impact of suicide gene therapy in allogeneic hematopoietic stem cell transplantation. Hum. Gene Ther. 21, 241-250 (2010).
18. A. Di Stasi, S. K. Tey, G. Dotti, Y. Fujita, A. Kennedy-Nasser, C. Martinez, K. Straathof, E. Liu, A. G. Durett, B. Grilley, H. Liu, C. R. Cruz, B. Savoldo, A. P. Gee, J. Schindler, R. A. Krance, H. E. Heslop, D. M. Spencer, C. M. Rooney, M. K. Brenner, Inducible apoptosis as a safety switch for adoptive cell therapy. N. Engl. J. Med. 365, 1673-1683 (2011).
19. I. Vogler, S. Newrzela, S. Hartmann, N. Schneider, D. von Laer, U. Koehl, M. Grez, An improved bicistronic CD20/tCD34 vector for efficient purification and in vivo depletion of gene-modified T cells for adoptive immunotherapy. Mol. Ther. 18, 1330-1338 (2010).
20. E. Kieback, J. Charo, D. Sommenneyer, T. Blankenstein, W. Uckert, A safeguard eliminates T cell receptor gene-modified autoreactive T cells after adoptive transfer. Proc. Natl. Acad. Sci. U.S.A. 105, 623-628 (2008).
21. D. M. Pardon, The blockade of immune checkpoints in cancer Immunotherapy. Nat. Rev. Cancer 12, 252-264 (2012).
22. P. Sharma, K. Wagner, J. D. Wolchok, J. P. Allison, Novel cancer immunotherapy agents with survival benefit: Recent successes and next steps. Nat. Rev. Cancer 11, 805-812 (2011).
23. E. A. Tivol, F. Borriello, A. N. Schweitzer, W. P. Lynch, J. A. Bluestone, A. H. Sharpe, Loss of CTLA-4 leads to massive lymphoproliferation and fatahnultiorgan tissue destruction, revealing a critical negative regulatory role of CTLA-4. Immunity 3, 541-547 (1995).
24. H. Nishimura, M. Nose, H. Hiai, N. Minato, T. Honjo, Development of lupus-like autoimmune diseases by disruption of the PD-1 gene encoding an ITIM motif-carrying immunoreceptor. Immunity 11, 141-151 (1999).
25. J. Wang, T. Yoshida, F. Nakaki, H. Hiai, T. Okazaki, T. Honjo, Establishment of NOD-Pdcd1-/- mice as an efficient animal model of type I diabetes. Proc. Natl. Acad. Sci. U.S.A. 102, 11823-11828 (2005).
26. R. V. Parry, J. M. Chemnitz, K. A. Frauwirth, A. R. Lanfranco, I. Braunstein, S. V. Kobayashi, P. S. Linsley, C. B. Thompson, J. L. Riley, CTLA-4 and PD-1 receptors inhibit T-cell activation by distinct mechanisms. Mol. Cell. Biol. 25, 9543-9553 (2005).
27. S. L. Topalian, F. S. Hodi, J. R. Brahmer, S. N. Gettinger, D. C. Smith, D. F. McDermott, J. D. Powderly, R. D. Carvajal, J. A. Sosman, M. B. Atkins, P. D. Leming, D. R. Spigel, S. J. Antonia, L. Horn, C. G. Drake, D. M. Pardoll, L. Chen, W. H. Sharfman, R. A. Anders, J. M. Taube, T. L. McMiller, H. Xu, A. J. Konnan, M. Jure-Kunkel, S. Agrawal, D. McDonald, G. D. Kollia, A. Gupta, J. M. Wigginton, M. Sznol, Safety, activity, and immune correlates of anti-PD-1 antibody in cancer. N. Engl. J. Med. 366, 2443-2454 (2012).
28. F. S. Hodi, S. J. O'Day, D. F. McDermott, R. W. Weber, J. A. Sosman, J. B. Haanen, R. Gonzalez, C. Robert, D. Schadendorf, J. C. Hassel, W. Akerley, A. J. van den Eertwegh, J. Lutzky, P. Lorigan, J. M. Vaubel, G. P. Linette, D. Hogg, C. H. Ottensmeier, C. Lebbé, C. Peschel, I. Quirt, J. I. Clark, J. D. Wolchok, J. S. Weber, J. Tian, M. J. Yellin, G. M. Nichol, A. Hoos, W. J. Urba, Improved survival with ipilimumab in patients with metastatic melanoma. N. Engl. J. Med. 363, 711-723 (2010).
29. V. A. Pedicord, W. Montalvo, I. M. Leiner, J. P. Allison, Single dose of anti-CTLA-4 enhances CD8+ T-cell memory formation, function, and maintenance. Proc. Natl. Acad. Sci. U.S.A. 108, 266-271 (2011).
30. V. Velu, K. Titanji, B. Zhu, S. Husain, A. Pladevega, L. Lai, T. H. Vanderford, L. Chennareddi, G. Silvestri, G. J. Freeman, R. Ahmed, R. R. Amara, Enhancing SIV-specific immunity in vivo by PD-1 blockade. Nature 458, 206-210 (2009).
31. T. P. Gade, W. Hassen, E. Santos, G. Gunset, A. Saudemont, M. C. Gong, R. Brentjens, X. S. Zhong, M. Stephan, J. Stefanski, C. Lyddane, J. R. Osborne, I. M. Buchanan, S. J. Hall, W. D. Heston, I. Rivière, S. M. Larson, J. A. Koutcher, M. Sadelain, Targeted elimination of prostate cancer by genetically directed human T lymphocytes. Cancer Res. 65, 9080-9088 (2005).
32. M. Sadelain, R. Brentjens, 1. Rivière, The basic principles of chimeric antigen receptor design. Cancer Discov. 3, 388-398 (2013).
33. Y. Kinoshita, K. Kuratsukuri, S. Landas, K. Imaida, P. M. Rovito Jr., C. Y. Wang, G. P. Haas, Expression of prostate-specific membrane antigen in normal and malignant human tissues. World J. Surg. 30, 628-636 (2006).
34. J. Maher, R. J. Brentjens, G. Gunset, I. Riviere, M. Sadelain, Human T-lymphocyte cytotoxicity and proliferation directed by a single chimeric TCRz/CD28 receptor. Nat. Biotechnol. 20, 70-75 (2002).
35. W. A. left, M. G. Kirchhof, J. Madrenas, A molecular perspective of CTLA-4 function. Annu. Rev. Immunol. 24, 65-97 (2006).
36. X. Fu, L. Tao, A. Rivera, S. Williamson, X. T. Song, N. Ahmed, X. Zhang, A simple and sensitive method for measuring tumor-specific T cell cytotoxicity. PLOS One 5, e11867 (2010).
37. R. J. Brentjens, E. Santos, Y. Nikhamin, R. Yeh, M. Matsushita, K. La Perle, A. QuintásCardama, S. M. Larson, M. Sadelain, Genetically targeted T cells eradicate systemic acute lymphoblastic leukemia xenografts. Clin. Cancer Res. 13, 5426-5435 (2007).
38. J. C. Markley, M. Sadelain, IL-7 and IL-21 are superior to IL-2 and IL-15 in promoting human T cell-mediated rejection of systemic lymphoma in immunodeficient mice. Blood 115, 3508-3519 (2010).
39. J. M. Chemnitz, R. V. Parry, K. E. Nichols, C. H. June, J. L. Riley, SHP-1 and SHP-2 associate with immunoreceptor tyrosine-based switch motif of programmed death 1 upon primary human T cell stimulation, but only receptor ligation prevents T cell activation. J. Immunol. 173, 945-954 (2004).
40. T. Yokosuka, M. Takamatsu, W. Kobayashi-Imanishi, A. Hashimoto-Tane, M. Azuma, T. Saito, Programmed cell death 1 forms negative costimulatory microclusters that directly inhibit T cell receptor signaling by recruiting phosphatase SHP2. J. Exp. Med. 209, 1201-1217 (2012).
41. Y. T. Bryceson, E. O. Long, Line of attack: NK cell specificity and integration of signals. Curr. Opin. Immunol. 20, 344-352 (2008).
42. S. Amarnath, C. W. Mangus, J. C. Wang, F. Wei, A. He, V. Kapoor, J. E. Foley, P. R. Massey, T. C. Felizardo, J. L. Riley, B. L. Levine, C. H. June, J. A. Medin, D. H. Fowler, The PDL1-PD1 axis converts human TH1 cells into regulatory T cells. Sci. Transl. Med. 3, 111ra120 (2011).
43. K. S. Peggs, S. A. Quezada, J. P. Allison, Cell intrinsic mechanisms of T-cell inhibition and application to cancer therapy. Immunol. Rev. 224, 141-165 (2008).
44. C. E. Rudd, The reverse stop-signal model for CTLA4 function. Nat. Rev. Immunol. 8, 153-160 (2008).

45. M. Uhlen, P. Oksvold, L. Fagerberg, E. Lundberg, K. Jonasson, M. Forsberg, M. Zwahlen, C. Kampf, K. Wester, S. Hober, H. Wernerus, L. Bjorling, F. Ponten, Towards a knowledge-based Human Protein Atlas. Nat. Biotechnol. 28, 1248-1250 (2010).

46. M. Campoli, S. Ferrone, HLA antigen changes in malignant cells: Epigenetic mechanisms and biologic significance. Oncogene 27, 5869-5885 (2008).

47. Y. Cui, Y. Ying, A. van Hasselt, K. M. Ng, J. Yu, Q. Zhang, J. Jin, D. Liu, J. S. Rhim, S. Y. Rha, M. Loyo, A. T. Chan, G. Srivastava, G. S. Tsao, G. C. Sellar, J. J. Sung, D. Sidransky, Q. Tao, OPCML is a broad tumor suppressor for multiple carcinomas and lymphomas with frequently epigenetic inactivation. PLOS One 3, e2990 (2008).

48. K. Singh, D. Mogare, R. O. Giridharagopalan, R. Gogiraju, G. Pande, S. Chattopadhyay, p53 target gene SMAR1 is dysregulated in breast cancer: Its role in cancer cell migration and invasion. PLOS One 2, e660 (2007).

49. L. Meimei, L. Peiling, L. Baoxin, L. Changmin, Z. Rujin, H. Chunjie, Lost expression of DCC gene in ovarian cancer and its inhibition in ovarian cancer cells. Med. Oncol. 28, 282-289 (2011).

50. S. Tsuboi, S. Hatakeyama, C. Ohyama, M. Fukuda, Two opposing roles of O-glycans in tumor metastasis. Trends Mol. Med. 18, 224-232 (2012).

51. B. Tsuchiya, Y. Sato, T. Kameya, I. Okayasu, K. Mukai, Differential expression of N-cadherin and E-cadherin in normal human tissues. Arch. Histol. Cytol. 69, 135-145 (2006).

52. C. L. Chaffer, R. A. Weinberg, A perspective on cancer cellmetastasis. Science 331, 1559-1564 (2011).

53. M. T. Stephan, V. Ponomarev, R. J. Brentjens, A. H. Chang, K. V. Dobrenkov, G. Heller, M. Sadelain, T cell-encoded CD80 and 4-1BBL induce auto- and trans-costimulation, resulting in potent tumor rejection. Nat. Med. 13, 1440-1449 (2007).

54. D. N. Burshtyn, C. Davidson, Natural killer cell conjugate assay using two-color flow cytometry. Methods Mol. Biol. 612, 89-96 (2010).

55. M. Themeli, C. C. Kloss, G. Ciriello, V. D. Fedorov, F. Perna, M. Gonen, M. Sadelain, Generation of tumor-targeted human T lymphocytes from induced pluripotent stem cells for cancer therapy. Nat. Biotechnol. 31, 928-933 (2013).

56. J. Yuan, J. B. Latouche, J. L. Reagan, G. Heller, I. Riviere, M. Sadelain, J. W. Young, Langerhans cells derived from genetically modified human CD34+ hemopoietic progenitors are more potent than peptide-pulsed Langerhans cells for inducing antigen-specific CD8+ cytolytic T lymphocyte responses. J. Immunol. 174, 758-766 (2005).

Embodiments of the Invention

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Some of the subject matter of this application may be related to U.S. patent application Ser. No. 12/593,751, which is the U.S. national phase application, pursuant to 35 U.S.C. §371, of International Patent Application No.: PCT/US2008/004251, filed Mar. 8, 2010, which claims the benefit of U.S. Provisional Application Ser. No. 60/921,144, filed Mar. 30, 2007, the disclosures of which are hereby incorporated herein in their entireties by reference.

All patents and publications mentioned in this specification are herein incorporated by reference to the same extent as if each independent patent and publication was specifically and individually indicated to be incorporated by reference.

APPENDIX A

Nucleic acid sequence of "P-PD1tm-PD1". "P-PD1tm-PD1" is an iCAR including a PD-1 transmembrane domain, a PD-1 cytoplasmic domain, and a PSMA svFV

```
atggCTCTCCCAGTGACTGCCCTACTGCTTCCCCTAGCGCTTCTCCTGCATGCAGAGGT
GCAGCTGCAGcagtcaggacctgaactggtgaagcctgggacttcagtgaggatatcct
gcaagacttctggatacacattcactgaatataccatacactgggtgaagcagagccat
ggaaagagccttgagtggattggaaacatcaatcctaacaatggtggtaccacctacaa
tcagaagttcgaggacaaggccacattgactgtagacaagtcctccagtacagcctaca
tggagctccgcagcctaacatctgaggattctgcagtctattattgtgcagctggttgg
aactttgactactggggccaagggaccacGGTCACCgtctcctcaggtggaggTggAtc
aggTggaggtggAtctggTggAggTggatcTGACATTGTGATGACCCAGTCTCACAAAT
TCATGTCCACATCAGTAGGAGACAGGGTCAGCATCATCTGTAAGGCCAGTCAAGATGTG
GGTACTGCTGTAGACTGGTATCAACAGAAACCAGGACAATCTCCTAAACTACTGATTTA
TTGGGCATCCACTCGGCACACTGGAGTCCCTGATCGCTTCACAGGCAGTGGATCTGGGA
CAGACTTCACTCTCACCATTACTAATGTTCAGTCTGAAGACTTGGCAGATTATTTCTGT
CAGCAATATAACAGCTATCCCCTCACGTTCGGTGCTGGGACCATGCTGGACCTGAAACG
GgcggccgcAgagagaagggcagaagtgcccacagcccaccccagcccctcacccaggc
cagccggccagttccaaaccctggtggttggtgtcgtgggcggcctgctgggcagcctg
gtgctgctagtctgggtcctggccgtcatctgctcccgggccgcacgagggacaatagg
agccaggcgcaccggccagcccctgaaggaggaccccctcagccgtgcctgtgttctctg
tggactatggggagctggatttccagtggcgagagaagaccccggagccccccgtgccc
tgtgtccctgagcagacggagtatgccaccattgtctttcctagcggaatgggcacctc
atccccgcccgcaggggctcagccgacggccctcggagtgcccagccactgaggcctg
aggatggacactgctcttggcccctctga [SEQ ID NO: 16]
```

Amino acid sequence of "P-PD1tm-PD1"

```
MALPVTALLLPLALLLHAEVQLQQSGPELVKPGTSVRISCKTSGYTFTEYTIHWVKQSH
GKSLEWIGNINPNNGGTTYNQKFEDKATLTVDKSSSTAYMELRSLTSEDSAVYYCAAGW
NFDYWGQGTTVTVSSGGGGSGGGGSGGGGSDIVMTQSHKFMSTSVGDRVSIICKASQDV
```

APPENDIX A-continued

GTAVDWYQQKPGQSPKLLIYWASTRHTGVPDRFTGSGSGTDFTLTITNVQSEDLADYFC
QQYNSYPLTFGAGTMLDLKRAAAERRAEVPTAHPSPSPRPAGQFQTLVVGVVGGLLGSL
VLLVWVLAVICSRAARGTIGARRTGQPLKEDPSAVPVFSVDYGELDFQWREKTPEPPVP
CVPEQTEYATIVFPSGMGTSSPARRGSADGPRSAQPLRPEDGHCSWPL [SEQ ID
NO: 17]

Nucleic acid sequence of "P-CTLA-4tm-CTLA-4wt", "P-CTLA-4tm-CTLA-4wt" is an iCAR including a CTLA-4 transmembrane domain, a wild-type CTLA-4 cytoplasmic domain and a PSMA svFV.

atggCTCTCCCAGTGACTGCCCTACTGCTTCCCCTAGCGCTTCTCCTGCATGCAGAGGT
GCAGCTGCAGcagtcaggacctgaactggtgaagcctgggacttcagtgaggatatcct
gcaagacttctggatacacattcactgaatataccatacactgggtgaagcagagccat
ggaaagagccttgagtggattggaaacatcaatcctaacaatggtggtaccacctacaa
tcagaagttcgaggacaaggccacattgactgtagacaagtcctccagtacagcctaca
tggagctccgcagcctaacatctgaggattctgcagtctattattgtgcagctggttgg
aactttgactactgggccaagggaccacGGTCACCgtctcctcaggtggaggTggAtc
aggTggaggtggAtctggTggAggTggatcTGACATTGTGATGACCCAGTCTCACAAAT
TCATGTCCACATCAGTAGGAGACAGGGTCAGCATCATCTGTAAGGCCAGTCAAGATGTG
GGTACTGCTGTAGACTGGTATCAACAGAAACCAGGACAATCTCCTAAACTACTGATTTA
TTGGGCATCCACTCGGCACACTGGAGTCCCTGATCGCTTCACAGGCAGTGGATCTGGGA
CAGACTTCACTCTCACCATTACTAATGTTCAGTCTGAAGACTTGGCAGATTATTTCTGT
CAGCAATATAACAGCTATCCCCTCACGTTCGGTGCTGGGACCATGCTGGACCTGAAACG
GgcggccgcACTGGGCATAGGCAACGGAACCCAGATTTATGTAATTGATCCAGAACCGT
GCCCAGATTCTGACTTCCTCCTCTGGATCCTTGCAGCAGTTAGTTCGGGGTTGTTTTTT
TATAGCTTTCTCCTCACAGCTGTTTCTTTGAGCAAAATGCTAAAGAAAAGAAGCCCTCT
TACAACAGGGGTCTATGTGAAAATGCCCCCAACAGAGCCAGAATGTGAAAAGCAATTTC
AGCCTTATTTTATTCCCATCAATTGA [SEQ ID NO: 18]

Amino acid sequence of "P-CTLA-4tm-CTLA-4wt"

MALPVTALLLPLALLLHAEVQLQQSGPELVKPGTSVRISCKTSGYTFTEYTIHWVKQSH
GKSLEWIGNINPNNGGTTYNQKFEDKATLTVDKSSSTAYMELRSLTSEDSAVYYCAAGW
NFDYWGQGTTVTVSSGGGGSGGGGSGGGGSDIVMTQSHKFMSTSVGDRVSIICKASQDV
GTAVDWYQQKPGQSPKLLIYWASTRHTGVPDRFTGSGSGTDFTLTITNVQSEDLADYFC
QQYNSYPLTFGAGTMLDLKRAAALGIGNGTQIYVIDPEPCPDSDFLLWILAAVSSGLFF
YSFLLTAVSLSKMLKKRSPLTTGVYVKMPPTEPECEKQFQPYFIPIN [SEQ ID NO:
19]

Nucleic acid sequence of "P-CTLA-4tm-CTLA-4mut" "P-CTLA-4tm-CTLA-4mut" is an iCAR including a mutant CTLA-4 transmembrane domain (Y165G mutant), a CTLA-1 cytoplasmic domain and a PSMA target svFV. Another two mutant versions of CTLA-4: Y182G mutant and Y165G & Y182G mutant, were also made.

atggCTCTCCCAGTGACTGCCCTACTGCTTCCCCTAGCGCTTCTCCTGCATGCAGAGGT
GCAGCTGCAGcagtcaggacctgaactggtgaagcctgggacttcagtgaggatatcct
gcaagacttctggatacacattcactgaatataccatacactgggtgaagcagagccat
ggaaagagccttgagtggattggaaacatcaatcctaacaatggtggtaccacctacaa
tcagaagttcgaggacaaggccacattgactgtagacaagtcctccagtacagcctaca
tggagctccgcagcctaacatctgaggattctgcagtctattattgtgcagctggttgg
aactttgactactgggccaagggaccacGGTCACCgtctcctcaggtggaggTggAtc
aggTggaggtggAtctggTggAggTggatcTGACATTGTGATGACCCAGTCTCACAAAT
TCATGTCCACATCAGTAGGAGACAGGGTCAGCATCATCTGTAAGGCCAGTCAAGATGTG
GGTACTGCTGTAGACTGGTATCAACAGAAACCAGGACAATCTCCTAAACTACTGATTTA
TTGGGCATCCACTCGGCACACTGGAGTCCCTGATCGCTTCACAGGCAGTGGATCTGGGA
CAGACTTCACTCTCACCATTACTAATGTTCAGTCTGAAGACTTGGCAGATTATTTCTGT
CAGCAATATAACAGCTATCCCCTCACGTTCGGTGCTGGGACCATGCTGGACCTGAAACG
GgcggccgcACTGGGCATAGGCAACGGAACCCAGATTTATGTAATTGATCCAGAACCGT
GCCCAGATTCTGACTTCCTCCTCTGGATCCTTGCAGCAGTTAGTTCGGGGTTGTTTTTT
TATAGCTTTCTCCTCACAGCTGTTTCTTTGAGCAAAATGCTAAAGAAAAGAAGCCCTCT
TACAACAGGGGTCGGTGAAAATGCCCCCAACAGAGCCAGAATGTGAAAAGCAATTTC
AGCCTTATTTTATTCCCATCAATTGA [SEQ ID NO: 20]

Amino acid sequence of "P-CTLA-4tm-CTLA-4mut"

MALPVTALLLPLALLLHAEVQLQQSGPELVKPGTSVRISCKTSGYTFTEYTIHWVKQSH
GKSLEWIGNINPNNGGTTYNQKFEDKATLTVDKSSSTAYMELRSLTSEDSAVYYCAAGW
NFDYWGQGTTVTVSSGGGGSGGGGSGGGGSDIVMTQSHKFMSTSVGDRVSIICKASQDV
GTAVDWYQQKPGQSPKLLIYWASTRHTGVPDRFTGSGSGTDFTLTITNVQSEDLADYFC
QQYNSYPLTFGAGTMLDLKRAAALGIGNGTQIYVIDPEPCPDSDFLLWILAAVSSGLFF
YSFLLTAVSLSKMLKKRSPLTTGVGVKMPPTEPECEKQFQPYFIPIN [SEQ ID NO: 21]

Nucleic acid sequence of "P-LAG3tm-LAG3". "P-LAG3tm-LAG3" is an iCAR including a LAG3 transmembrane domain, a LAG3 cytoplasmic domain, and a PSMA svFV atggCTCTCCCAGTGACTGCCCTACTGCTTCCCCTAGCGCTTCTCCTGCATGCAGAGGT
GCAGCTGCAGcagtcaggacctgaactggtgaagcctgggacttcagtgaggatatcct
gcaagacttctggatacacattcactgaatataccatacactgggtgaagcagagccat APPENDIX A-continued

```
ggaaagagccttgagtggattggaaacatcaatcctaacaatggtggtaccacctacaa
tcagaagttcgaggacaaggccacattgactgtagacaagtcctccagtacagcctaca
tggagctccgcagcctaacatctgaggattctgcagtctattattgtgcagctggttgg
aactttgactactggggccaagggaccacGGTCACCgtctcctcaggtggaggTggAtc
aggTggaggtggAtctggTggAggTggatcTGACATTGTGATGACCCAGTCTCACAAAT
TCATGTCCACATCAGTAGGAGACAGGGTCAGCATCATCTGTAAGGCCAGTCAAGATGTG
GGTACTGCTGTAGACTGGTATCAACAGAAACCAGGACAATCTCCTAAACTACTGATTTA
TTGGGCATCCACTCGGCACACTGGAGTCCCTGATCGCTTCACAGGCAGTGGATCTGGGA
CAGACTTCACTCTCACCATTACTAATGTTCAGTCTGAAGACTTGGCAGATTATTTCTGT
CAGCAATATAACAGCTATCCCCTCACGTTCGGTGCTGGGACCATGCTGGACCTGAAACG
GgcggccgcACTTGGAGCAGCAGTGTACTTCACAGAGCTGTCTAGCCCAGGTGCCCAAC
GCTCTGGGAGAGCCCCAGGTGCCCTCCCAGCAGGCCACCTCCTGCTGTTTCTCATCCTT
GGTGTCCTTTCTCTGCTCCTTTTGGTGACTGGAGCCTTTGGCTTTCACCTTTGGAGAAG
ACAGTGGCGACCAAGACGATTTTCTGCCTTAGAGCAAGGGATTCACCCTCCGCAGGCTC
AGAGCAAGATAGAGGAGCTGGAGCAAGAACCGGAGCCGGAGCCGGAGCCGGAACCGGAG
CCCGAGCCCGAGCCCGAGCCGGAGCAGCTCTGA [SEQ ID NO: 22]
```

Amino acid sequence of "P-LAG3tm-LAG3"

```
MALPVTALLLPLALLLHAEVQLQQSGPELVKPGTSVRISCKTSGYTFTEYTIHWVKQSH
GKSLEWIGNINPNNGGTTYNQKFEDKATLTVDKSSSTAYMELRSLTSEDSAVYYCAAGW
NFDYWGQGTTVTVSSGGGGSGGGGSGGGGSDIVMTQSHKFMSTSVGDRVSIICKASQDV
GTAVDWYQQKPGQSPKLLIYWASTRHTGVPDRFTGSGSGTDFTLTITNVQSEDLADYFC
QQYNSYPLTFGAGTMLDLKRAAALGAAVYFTELSSPGAQRSGRAPGALPAGHLLLFLIL
GVLSLLLLVTGAFGFHLWRRQWRPRRFSALEQGTHPPQAQSKIEELEQEPEPEPEPEPE
PEPEPEPEQL [SEQ ID NO: 23]
```

Nucleic acid sequence of "P-BTLAtm-BTLA". "P-BTLAtm-BTLA" is an iCAR including a BTLA transmembrane domain, a BTLA cytoplasmic domain, and a PSMA svFV

```
atggCTCTCCCAGTGACTGCCCTACTGCTTCCCCTAGCGCTTCTCCTGCATGCAGAGGT
GCAGCTGCAGcagtcaggacctgaactggtgaagcctgggacttcagtgaggatatcct
gcaagacttctggatacacattcactgaatataccatacactgggtgaagcagagccat
ggaaagagccttgagtggattggaaacatcaatcctaacaatggtggtaccacctacaa
tcagaagttcgaggacaaggccacattgactgtagacaagtcctccagtacagcctaca
tggagctccgcagcctaacatctgaggattctgcagtctattattgtgcagctggttgg
aactttgactactggggccaagggaccacGGTCACCgtctcctcaggtggaggTggAtc
aggTggaggtggAtctggTggAggTggatcTGACATTGTGATGACCCAGTCTCACAAAT
TCATGTCCACATCAGTAGGAGACAGGGTCAGCATCATCTGTAAGGCCAGTCAAGATGTG
GGTACTGCTGTAGACTGGTATCAACAGAAACCAGGACAATCTCCTAAACTACTGATTTA
TTGGGCATCCACTCGGCACACTGGAGTCCCTGATCGCTTCACAGGCAGTGGATCTGGGA
CAGACTTCACTCTCACCATTACTAATGTTCAGTCTGAAGACTTGGCAGATTATTTCTGT
CAGCAATATAACAGCTATCCCCTCACGTTCGGTGCTGGGACCATGCTGGACCTGAAACG
GgcggccgcAGATGTAAAAAGTGCCTCAGAACGACCCTCCAAGGACGAAATGGCAAGCA
GACCCTGGCTCCTGTATAGTTTACTTCCTTTGGGGGATTGCCTCTACTCATCACTACC
TGTTTCTGCCTGTTCTGCTGCCTGAGAAGGCACCAAGGAAAGCAAAATGAACTCTCTGA
CACAGCAGGAAGGGAAATTAACCTGGTTGATGCTCACCTTAAGAGTGAGCAAACAGAAG
CAAGCACCAGGCAAAATTCCCAAGTACTGCTATCAGAAACTGGAATTTATGATAATGAC
CCTGACCTTTGTTTCAGGATGCAGGAAGGGTCTGAAGTTTATTCTAATCCATGCCTGGA
AGAAAACAAACCAGGCATTGTTTATGCTTCCCTGAACCATTCTGTCATTGGACCGAACT
CAAGACTGGCAAGAAATGTAAAAGAAGCACCAACAGAATATGCATCCATATGTGTGAGG
AGTTAA [SEQ ID NO: 24]
```

Amino acid sequence of "P-BTLAtm-BTLA"

```
MALPVTALLLPLALLLHAEVQLQQSGPELVKPGTSVRISCKTSGYTFTEYTTHWVKQSH
GKSLEWIGNINPNNGGTTYNQKFEDKATLTVDKSSSTAYMELRSLTSEDSAVYYCAAGW
NFDYWGQGTTVTVSSGGGGSGGGGSGGGGSDIVMTQSHKFMSTSVGDRVSIICKASQDV
GTAVDWYQQKPGQSPKLLIYWASTRHTGVPDRFTGSGSGTDFTLTITNVQSEDLADYFC
QQYNSYPLTFGAGTMLDLKRAAADVKSASERPSKDEMASRPWLLYSLLPLGGLPLLITT
CFCLFCCLRRHQGKQNELSDTAGREINLVDAHLKSEQTEASTRQNSQVLLSETGIYDND
PDLCFRMQEGSEVYSNPCLEENKPGIVYASLNHSVIGPNSRLARNVKEAPTEYASICVR
S [SEQ ID NO: 25]
```

Nucleic acid sequence of "P-2B4tm-2B4". "P-2B4tm-2B4" is an iCAR including an iCAR including a 2B4 transmembrane domain, a 2B4 cytoplasmic domain, and a PSMA svFV

```
atggCTCTCCCAGTGACTGCCCTACTGCTTCCCCTAGCGCTTCTCCTGCATGCAGAGGT
GCAGCTGCAGcagtcaggacctgaactggtgaagcctgggacttcagtgaggatatcct
gcaagacttctggatacacattcactgaatataccatacactgggtgaagcagagccat
ggaaagagccttgagtggattggaaacatcaatcctaacaatggtggtaccacctacaa
tcagaagttcgaggacaaggccacattgactgtagacaagtcctccagtacagcctaca
tggagctccgcagcctaacatctgaggattctgcagtctattattgtgcagctggttgg
aactttgactactggggccaagggaccacGGTCACCgtctcctcaggtggaggTggAtc
aggTggaggtggAtctggTggAggTggatcTGACATTGTGATGACCCAGTCTCACAAAT
TCATGTCCACATCAGTAGGAGACAGGGTCAGCATCATCTGTAAGGCCAGTCAAGATGTG
GGTACTGCTGTAGACTGGTATCAACAGAAACCAGGACAATCTCCTAAACTACTGATTTA
TTGGGCATCCACTCGGCACACTGGAGTCCCTGATCGCTTCACAGGCAGTGGATCTGGGA
```

APPENDIX A-continued

```
CAGACTTCACTCTCACCATTACTAATGTTCAGTCTGAAGACTTGGCAGATTATTTCTGT
CAGCAATATAACAGCTATCCCCTCACGTTCGGTGCTGGGACCATGCTGGACCTGAAACG
GgcggccgcACAGGACTGTCAGAATGCCCATCAGGAATTCAGATTTTGGCCGTTTTTGG
TGATCATCGTGATTCTAAGCGCACTGTTCCTTGGCACCCTTGCCTGCTTCTGTGTGTGG
AGGAGAAAGAGGAAGGAGAAGCAGTCAGAGACCAGTCCCAAGGAATTTTTGACAATTTA
CGAAGATGTCAAGGATCTGAAAACCAGGAGAAATCACGAGCAGGAGCAGACTTTTCCTG
GAGGGGGGAGCACCATCTACTCTATGATCCAGTCCCAGTCTTCTGCTCCCACGTCACAA
GAACCTGCATATACATTATATTCATTAATTCAGCCTTCCAGGAAGTCTGGATCCAGGAA
GAGGAACCACAGCCCTTCCTTCAATAGCACTATCTATGAAGTGATTGGAAAGAGTCAAC
CTAAAGCCCAGAACCCTGCTCGATTGAGCCGCAAAGAGCTGGAGAACTTTGATGTTTAT
TCCTAG [SEQ ID NO: 26]
```

Amino acid sequence of "P-2B4tm-2B4"

```
MALPVTALLLPLALLLHAEVQLQQSGPELVKPGTSVRISCKTSGYTFTEYTIHWVKQSH
GKSLEWIGNINPNNGGTTYNQKFEDKATLTVDKSSSTAYMELRSLTSEDSAVYYCAAGW
NFDYWGQGTTVTVSSGGGGSGGGGSGGGGSDIVMTQSHKFMSTSVGDRVSIICKASQDV
GTAVDWYQQKPGQSPKLLIYWASTRHTGVPDRFTGSGSGTDFTLTITNVQSEDLADYFC
QQYNSYPLTFGAGTMLDLKRAAAQDCQNAHQEFRFWPFLVIIVILSALFLGTLACFCVW
RRKRKEKQSETSPKEFLTIYEDVKDLKTRRNHEQEQTFPGGGSTIYSMIQSQSSAPTSQ
EPAYTLYSLIQPSRKSGSRKRNHSPSFNSTIYEVIGKSQPKAQNPARLSRKELENFDVY
S [SEQ ID NO: 27]
```

Nucleic acid sequence of "Full CTLA4 tail CD8 hindge and tm", which is an iCAR including CD8 hinge and trasmembrane domains, a CTLA-4 intracellular tail, and a PSMA svFV

```
atggCTCTCCCAGTGACTGCCCTACTGCTTCCCCTAGCGCTTCTCCTGCATGCAGAGGT
GCAGCTGCAGcagtcaggacctgaactggtgaagcctgggacttcagtgaggatatcct
gcaagacttctggatacacattcactgaatataccatacactgggtgaagcagagccat
ggaaagagccttgagtggattggaaacatcaatcctaacaatggtggtaccacctacaa
tcagaagttcgaggacaaggccacattgactgtagacaagtcctccagtacagcctaca
tggagctccgcagcctaacatctgaggattctgcagtctattattgtgcagctggttgg
aactttgactactggggccaagggaccacGGTCACCgtctcctcaggtggaggTggAtc
aggTggaggtggAtctggTggAggTggatcTGACATTGTGATGACCCAGTCTCACAAAT
TCATGTCCACATCAGTAGGAGACAGGGTCAGCATCATCTGTAAGGCCAGTCAAGATGTG
GGTACTGCTGTAGACTGGTATCAACAGAAACCAGGACAATCTCCTAAACTACTGATTTA
TTGGGCATCCACTCGGCACACTGGAGTCCCTGATCGCTTCACAGGCAGTGGATCTGGGA
CAGACTTCACTCTCACCATTACTAATGTTCAGTCTGAAGACTTGGCAGATTATTTCTGT
CAGCAATATAACAGCTATCCCCTCACGTTCGGTGCTGGGACCATGCTGGACCTGAAACG
GgcggccgcACCCACCACGACGCCAGCGCCGCGACCACCAACCCCGGCGCCCACGATCG
CGTCGCAGCCCctgtccctgcgcccagaggcgtgccggccagcggcgggggcgcagtg
cacacgaggggggctggacttcgcctgtgatatctacatctgggcgcccCtggccgggac
ttgtggggtccttctcctgtcactggttatcacccctttactgcaaccacagagcaccgg
cgGTTTCTTTGAGCAAAATGCTAAAGAAAAGAAGCCCTCTTACAACAGGGGTCGGTGTG
AAAATGCCCCCAACAGAGCCAGAATGTGAAAAGCAATTTCAGCCTTATTTTATTCCCAT
CAATTGA [SEQ ID NO: 28]
```

Amino acid sequence of "Full CTLA4 tail CD8 hindge and tm"

```
MALPVTALLLPLALLLHAEVQLQQSGPELVKPGTSVRISCKTSGYTFTEYTIHWVKQSH
GKSLEWIGNINPNNGGTTYNQKFEDKATLTVDKSSSTAYMELRSLTSEDSAVYYCAAGW
NFDYWGQGTTVTVSSGGGGSGGGGSGGGGSDIVMTQSHKFMSTSVGDRVSIICKASQDV
GTAVDWYQQKPGQSPKLLIYWASTRHTGVPDRFTGSGSGTDFTLTITNVQSEDLADYFC
QQYNSYPLTFGAGTMLDLKRAAAPTTTPAPRPPTPAPTIASQPLSLRPEACRPAAGGAV
HTRGLDFACDIYIWAPLAGTCGVLLLSLVITLYCNHRAPAVSLSKMLKKRSPLTTGVGV
KMPPTEPECEKQFQPYFIPIN [SEQ ID NO: 29]
```

Nucleic acid sequence of "P-CD8tm-PD1". "P-CD8tm-PD1" is an iCAR including a CD8 trasmembrane domain, a PD-1 cytoplasmic domain, and a PSMA svFV

```
atggCTCTCCCAGTGACTGCCCTACTGCTTCCCCTAGCGCTTCTCCTGCATGCAGAGGT
GCAGCTGCAGcagtcaggacctgaactggtgaagcctgggacttcagtgaggatatcct
gcaagacttctggatacacattcactgaatataccatacactgggtgaagcagagccat
ggaaagagccttgagtggattggaaacatcaatcctaacaatggtggtaccacctacaa
tcagaagttcgaggacaaggccacattgactgtagacaagtcctccagtacagcctaca
tggagctccgcagcctaacatctgaggattctgcagtctattattgtgcagctggttgg
aactttgactactggggccaagggaccacGGTCACCgtctcctcaggtggaggTggAtc
aggTggaggtggAtctggTggAggTggatcTGACATTGTGATGACCCAGTCTCACAAAT
TCATGTCCACATCAGTAGGAGACAGGGTCAGCATCATCTGTAAGGCCAGTCAAGATGTG
GGTACTGCTGTAGACTGGTATCAACAGAAACCAGGACAATCTCCTAAACTACTGATTTA
TTGGGCATCCACTCGGCACACTGGAGTCCCTGATCGCTTCACAGGCAGTGGATCTGGGA
CAGACTTCACTCTCACCATTACTAATGTTCAGTCTGAAGACTTGGCAGATTATTTCTGT
CAGCAATATAACAGCTATCCCCTCACGTTCGGTGCTGGGACCATGCTGGACCTGAAACG
GgcggccgcACCCACCACGACGCCAGCGCCGCGACCACCAACCCCGGCGCCCACGATCG
CGTCGCAGCCCctgtccctgcgcccagaggcgtgccggccagcggcgggggcgcagtg
cacacgaggggggctggacttcgcctgtgatatctacatctgggcgcccCtggccgggac
ttgtggggtccttctcctgtcactggttatcacccctttactgcaaccacagaatgcatt
gctcccggggccgcacgagggacaataggagccaggcgcaccggccagcccctgaaggag
```

APPENDIX A-continued

```
gacccctcagccgtgcctgtgttctctgtggactatggggagctggatttccagtggcg
agagaagaccccggagccccccgtgccctgtgtccctgagcagacggagtatgccacca
ttgtctttcctagcggaatgggcacctcatccccgcccgcaggggctcagccgacggc
cctcggagtgcccagccactgaggcctgaggatggacactgctcttggcccctctga
[SEQ ID NO: 30]
```

Amino acid sequence of "P-CD8tm-PD1"

```
MALPVTALLLPLALLLHAEVQLQQSGPELVKPGTSVRISCKTSGYTFTEYTIHWVKQSH
GKSLEWIGNINPNNGGTTYNQKFEDKATLTVDKSSSTAYMELRSLTSEDSAVYYCAAGW
NFDYWGQGTTVTVSSGGGGSGGGGSGGGGSDIVMTQSHKFMSTSVGDRVSIICKASQDV
GTAVDWYQQKPGQSPKLLIYWASTRHTGVPDRFTGSGSGTDFTLTITNVQSEDLADYFC
QQYNSYPLTFGAGTMLDLKRAAAPTTTPAPRPPTPAPTIASQPLSLRPEACRPAAGGAV
HTRGLDFACDIYTWAPLAGTCGVLLLSLVITLYCNHRMHCSRAARGTIGARRTGQPLKE
DPSAVPVFSVDYGELDFQWREKTPEPPVPCVPEQTEYATIVFPSGMGTSSPARRGSADG
PRSAQPLRPEDGHCSWPL [SEQ ID NO: 31]
```

Nucleic acid sequence of "P-CD8tm-CTLA4wt". "P-CD8tm-CTLA4wt" is an iCAR including a CD8 trasmembrane domains, a wild-type CTLA-4 cytoplasmic domain, and a PSMA svFV

```
atggCTCTCCCAGTGACTGCCCTACTGCTTCCCCTAGCGCTTCTCCTGCATGCAGAGGT
GCAGCTGCAGcagtcaggacctgaactggtgaagcctgggacttcagtgaggatatcct
gcaagacttctggatacacattcactgaatataccatacactgggtgaagcagagccat
ggaaagagccttgagtggattggaaacatcaatcctaacaatggtggtaccacctacaa
tcagaagttcgaggacaaggccacattgactgtagacaagtcctccagtacagcctaca
tggagctccgcagcctaacatctgaggattctgcagtctattattgtgcagctggttgg
aactttgactactggggccaagggaccacGGTCACCgtctcctcaggtggaggTggAtc
aggTggaggtgAtctggTggAggTggatcTGACATTGTGATGACCCAGTCTCACAAAT
TCATGTCCACATCAGTAGGAGACAGGGTCAGCATCATCTGTAAGGCCAGTCAAGATGTG
GGTACTGCTGTAGACTGGTATCAACAGAAACCAGGACAATCTCCTAAACTACTGATTTA
TTGGGCATCCACTCGGCACACTGGAGTCCCTGATCGCTTCACAGGCAGTGGATCTGGGA
CAGACTTCACTCTCACCATTACTAATGTTCAGTCTGAAGACTTGGCAGATTATTTCTGT
CAGCAATATAACAGCTATCCCCTCACGTTCGGTGCTGGGACCATGCTGGACCTGAAACG
GgcggccgcACCCACCACGACGCCAGCGCCGCGACCACCAACCCCGGCGCCCACGATCG
CGTCGCAGCCCctgtccctgcgcccagaggcgtgccggccagcggcggggggcgcagtg
cacacgaggggctggacttcgcctgtgatatctacatctgggcgcccCtggccgggac
ttgtggggtccttctcctgtcactggttatcacccttactgcaaccacagagcaccgg
cgATGCTAAAGAAAAGAAGCCCTCTTACAACAGGGGTCTATGTGAAAATGCCCCCAACA
GAGCCAGAATGTGAAAAGCAATTTCAGCCTTATTTTATTCCCATCAATTGA [SEQ ID
NO: 32]
```

Amino acid sequence of "P-CD8tm-CTLA4wt"

```
MALPVTALLLPLALLLHAEVQLQQSGPELVKPGTSVRISCKTSGYTFTEYTTHWVKQSH
GKSLEWIGNINPNNGGTTYNQKFEDKATLTVDKSSSTAYMELRSLTSEDSAVYYCAAGW
NFDYWGQGTTVTVSSGGGGSGGGGSGGGGSDIVMTQSHKFMSTSVGDRVSIICKASQDV
GTAVDWYQQKPGQSPKLLIYWASTRHTGVPDRFTGSGSGTDFTLTITNVQSEDLADYFC
QQYNSYPLTFGAGTMLDLKRAAAPTTTPAPRPPTPAPTIASQPLSLRPEACRPAAGGAV
HTRGLDFACDIYIWAPLAGTCGVLLLSLVITLYCNHRAPAMLKKRSPLTTGVYVKMPPT
EPECEKQFQPYFIPIN [SEQ ID NO: 33]
```

What is claimed is:

1. A T cell comprising:
   a) a chimeric antigen receptor (CAR) comprising an extracellular antigen-binding domain comprising a single chain variable fragment (scFv) that binds to a first antigen that is expressed at the surface of a tumor cell, and an intracellular signaling domain that is capable of activating the T cell and comprises a signaling domain of CD28, and
   b) an inhibitory chimeric antigen receptor (iCAR) comprising an extracellular antigen-binding domain comprising a single chain variable fragment (scFv) that binds to a second antigen that is not expressed on the tumor cell surface, and a signaling domain of an immunoinhibitory receptor selected from the group consisting of CTLA-4, PD-1, LAG-3, 2B4, and BTLA, wherein binding of the CAR to the first antigen induces cytotoxicity of the T cell, an binding of the iCAR to the second antigen reduces the cytotoxicity of the T cell induced by the CAR.

2. The T cell of claim 1, wherein said iCAR is recombinantly expressed.

3. The T cell of claim 1, wherein the iCAR is expressed from a vector.

4. The T cell of claim 1, wherein said CAR is recombinantly expressed.

5. The T cell of claim 1, wherein the CAR is expressed from a vector.

6. The T cell of claim 1, wherein the T cell is selected from the group consisting of effector T cells, and memory T cells..

7. The T cell of claim 1, wherein said T cell is autologous.

8. The T cell of claim 1, wherein said T cell is non-autologous..

9. The T cell of claim 1, wherein said first antigen selected from the group consisting of CD19, CD7, CD10, CD20, CD22, CD30, CD33, CD34, CD38, CD41, CD44, CD49f, CD56, CD74, CD123, CD133, CD138, CAIX, CEA, CD5, EGP-2, EGP-40, EpCAM, Erb-B2, Erb-B3, Erb-B4, FBP, Fetal acetylcholine receptor, folate receptor-a, GD2, GD3, HER-2, IL-13R-α2, κ-light chain, LeY, L1 cell adhesion molecule, Mesothelin, Muc-1, Muc-16, oncofetal antigen (h5T4), PSCA, PSMA, ROR1, TAG-72, and VEGF-R2.

10. The T cell of claim 1, wherein said iCAR further comprises a transmembrane domain selected from the group consisting of a CD4 polypeptide, a CD8 polypeptide, a CTLA-4 polypeptide, a PD-1 polypeptide, a LAG-3 polypeptide, a 2B4 polypeptide, and a BTLA polypeptide.

11. The T cell of claim 6, wherein said effector T cells are selected from the group consisting of helper T cells (CD4+ T cells), and cytotoxic T cells (CD8+ T cells).

12. The T cell of claim 1, wherein said first antigen is selected from the group consisting of CD19, PSMA, mesothelin, and CD56.

13. The T cell of claim 1, wherein the second antigen is selected from the group consisting of an Epithelial-mesenchymal transition (EMT) antigen, cytokeratin, human leukocyte antigens (HLAs), Opioid-binding protein/cell adhesion molecule (OPCML), HYAL2, Deleted in Colorectal Carcinoma (DCC), Scaffold/Matrix attachment region-binding protein 1 (SMAR1), CD33, CD38, and E-cadherin.

14. A pharmaceutical composition comprising a pharmaceutically acceptable excipient and an effective amount of T cells, wherein said T cell comprises:
  (a) a chimeric antigen receptor (CAR) comprising an extracellular antigen-binding domain comprising a single chain variable fragment (scFv) that binds to a first antigen that is expressed at the surface of a tumor cell, and an intracellular signaling domain that is capable of activating the T cell and comprises a signaling domain of CD28, and
  (b) an inhibitory chimeric antigen receptor (iCAR) comprising an extracellular antigen-binding domain comprising a single chain variable fragment (scFv) that binds to a second antigen that is not expressed on the tumor cell surface, and a signaling domain of an immunoinhibitory receptor selected from the group consisting of CTLA-4, PD-1, LAG-3, 2B4, and BTLA, wherein binding of the CAR to the first antigen induces cytotoxicity of the T cell, and binding of the iCAR to the second antigen reduces the cytotoxicity of the T cell induced by the CAR.

15. The pharmaceutical composition of claim 14, wherein the second antigen is selected from the group consisting of an Epithelial-mesenchymal transition (EMT) antigen, cytokeratin, human leukocyte antigens (HLAs), Opioid-binding protein/cell adhesion molecule (OPCML), HYAL2, Deleted in Colorectal Carcinoma (DCC), Scaffold/Matrix attachment region-binding protein 1 (SMAR1), CD33, CD38, and E-cadherin.

16. A kit comprising a T cell, wherein said T cells comprises:
  (a) a chimeric antigen receptor (CAR) comprising an extracellular antigen-binding domain comprising a single chain variable fragment (scFv) that binds to a first antigen that is expressed at the surface of a tumor cell, and an intracellular signaling domain that is capable of activating the T cell and comprises a signaling domain of CD28, and
  (b) an inhibitory chimeric antigen receptor (iCAR) comprising an extracellular antigen-binding domain comprising a single chain variable fragment (scFv) that binds to a second antigen that is not expressed on the tumor cell surface, and a signaling domain of an immunoinhibitory receptor selected from the group consisting of CTLA-4, PD-1, LAG-3, 2B4, and BTLA, wherein binding of the CAR to the first antigen induces cytotoxicity of the T cell, and binding of the iCAR to the second antigen reduces the cytotoxicity of the T cell induced by the CAR.

17. The kit of claim 16, wherein the kit further comprises written instructions for using said cell for the treatment of a subject having a neoplasm.

18. The kit of claim 16, wherein the second antigen is selected from the group consisting of an Epithelial-mesenchymal transition (EMT) antigen, cytokeratin, human leukocyte antigens (HLAs), Opioid-binding protein/cell adhesion molecule (OPCML), HYAL2, Deleted in Colorectal Carcinoma (DCC), Scaffold/Matrix attachment region-binding protein 1 (SMAR1), CD33, CD38, and E-cadherin.

* * * * *

UNITED STATES PATENT AND TRADEMARK OFFICE
CERTIFICATE OF CORRECTION

| | |
|---|---|
| PATENT NO. | : 11,267,901 B2 |
| APPLICATION NO. | : 14/851983 |
| DATED | : March 8, 2022 |
| INVENTOR(S) | : Victor D. Fedorov and Michel Sadelain |

It is certified that error appears in the above-identified patent and that said Letters Patent is hereby corrected as shown below:

On the Title Page

Item (56) Column 2, Line 27, "Mol. Cel. Biol." should read -- Mol. Cell. Biol. --; and Item (56) Column 2, Line 31, "Human THI Cells" should read -- Human TH1 Cells --.

In the Claims

In Claim 1, Column 123, Line 54, "an binding to the iCAR" should read -- and binding of the iCAR --;

In Claim 6, Column 123, Line 66, "memory T cells.." should read -- memory T cells. --;

In Claim 8, Column 124, Line 37, "T cell is autologous.." should read -- T cell is autologous. --;

In Claim 9, Column 124, Line 38, "first antigen selected" should read -- first antigen is selected --; and In Claim 9, Column 124, Line 44, "folate receptor-a" should read -- folate receptor-α --.

Signed and Sealed this
Twenty-eighth Day of February, 2023

*Katherine Kelly Vidal*

Katherine Kelly Vidal
*Director of the United States Patent and Trademark Office*